US011690341B2

(12) United States Patent
Knudsen et al.

(10) Patent No.: US 11,690,341 B2
(45) Date of Patent: Jul. 4, 2023

(54) CEREAL PLANTS WITH IMPROVED CELL WALL PROPERTIES

(71) Applicant: Carlsberg A/S, Copenhagen V (DK)

(72) Inventors: Søren Knudsen, Copenhagen V (DK); Sabrina Bodevin, Malmö (SE); Ole Olsen, Copenhagen S (DK); Hanne Thomsen, Copenhagen V (DK); Toni Wendt, Copenhagen V (DK); Jesper Harholt, Copenhagen V (DK); Finn Lok, Copenhagen V (DK)

(73) Assignee: Carlsberg A/S, Copenhagen V (DK)

(*) Notice: Subject to any disclaimer, the term of this patent is extended or adjusted under 35 U.S.C. 154(b) by 226 days.

(21) Appl. No.: 16/958,092

(22) PCT Filed: Dec. 21, 2018

(86) PCT No.: PCT/EP2018/086719
§ 371 (c)(1),
(2) Date: Jun. 25, 2020

(87) PCT Pub. No.: WO2019/129736
PCT Pub. Date: Jul. 4, 2019

(65) Prior Publication Data
US 2021/0062208 A1 Mar. 4, 2021

(30) Foreign Application Priority Data
Dec. 28, 2017 (EP) .................................... 17210954

(51) Int. Cl.
| C12N 15/82 | (2006.01) |
| A01H 6/46 | (2018.01) |
| C12C 1/18 | (2006.01) |
| A01H 5/10 | (2018.01) |
| C12C 1/027 | (2006.01) |
| C12C 1/16 | (2006.01) |
| C12N 9/10 | (2006.01) |

(52) U.S. Cl.
CPC ............. *A01H 6/4624* (2018.05); *A01H 5/10* (2013.01); *C12C 1/027* (2013.01); *C12C 1/16* (2013.01); *C12C 1/18* (2013.01); *C12N 9/1051* (2013.01); *C12N 15/8245* (2013.01); *C12Y 204/01012* (2013.01)

(58) Field of Classification Search
None
See application file for complete search history.

(56) References Cited

U.S. PATENT DOCUMENTS

2011/0318469 A1* 12/2011 Skadhauge ............... C12C 1/18
426/507

FOREIGN PATENT DOCUMENTS

| EP | 2402440 A1 | 1/2012 |
| GB | 1121394 A | 7/1968 |
| GB | 1121394 A | 2/1996 |
| JP | 2000515381 A | 11/2000 |
| JP | 2010193847 A | 9/2010 |
| JP | 2013526875 A | 6/2013 |
| WO | 2005087934 A2 | 9/2005 |
| WO | 2007014433 A1 | 2/2007 |
| WO | 2010063288 A2 | 6/2010 |
| WO | 2010075860 A2 | 7/2010 |
| WO | 2018001882 A1 | 1/2018 |
| WO | 2018001884 A1 | 1/2018 |

OTHER PUBLICATIONS

Hu et al, 2014, Journal of Cereal Science, 59:189-195.*
Jobling, 2015, Science Advances, 1:1-9.*
Wong et al, 2015, Mol Breeding, 35:1-12.*
Woonton et al., 2003, "The effect of post-harvest storage period on barley germination, malt quality and water uptake." Proceedings of the 10th Australian barley Technical Symposium. Canberra.*
Burton et al., "Evolution and development of cell walls in cereal grains", Frontiers in Plant Science, vol. 5 (2014).
Burton et al., "Over-expression of specific HvCsIF cellulose synthase-like genes in transgenic barley increases the levels of cell wall (1,3;1,4)-[beta]-d-glucans and alters their fine structure: Over-expression of CsIF genes in barley", Plant Biotechnology Journal, 9(2) (2011).
Database UniProt [Online] Feb. 17, 2016 (Feb. 17, 2016), "SubName: Full=CsIF6 {ECO:0000313|EMBL: AKJ66176.1};".
Dimitroff et al., "(1,3;1,4)-[beta]-Glucan Biosynthesis by the CSLF6 Enzyme: Position and Flexibility of Catalytic Residues Influence Product Fine Structure", Biochemistry, 55(13) (2016).
Hu et al., "A mutation of the cellulose-synthase-like gene in barley partially affects the [beta]-glucan content in grains", Journal of Cereal Science, vol. 59 (2014).
Jobling, S.A., "Membrane pore architecture of the CsIF6 protein controls (1-3,1-4)-ß-glucan structure", Science Advances, 1(5) (Jun. 2015).
Pedersen et al., "Versatile high resolution oligosaccharide microarrays for plant glycobiology and cell wall research", Journal of Biological Chemistry, 287(47), pp. 39429-39438 (2012).
Sun et al., "Engineering Herbicide-Resistant Rice Plants through CRISPR/Cas9-Mediated Homologous Recombination of Acetolactate Synthase", Letter to the editor, Molecular Plant, 9(4), pp. 628-631 (2016).
Taketa et al., "Functional characterization of barley betaglucanless mutants demonstrates a unique role for CsIF6 in (1,3;1,4)-[beta]-D-glucan biosynthesis", Journal of Experimental Botany, 63(1) (2011).
Wilson et al., "Determining the subcellular location of synthesis and assembly of the cell wall polysaccharide (1,3;1,4)-ß-D-glucan in grasses", The Plant cell, vol. 27; pp. 754-111 (2015).

* cited by examiner

Primary Examiner — Jason Deveau Rosen
(74) Attorney, Agent, or Firm — McNeill Baur PLLC

(57) ABSTRACT

The present invention relates to barley plant or a part thereof, wherein the kernels of said barley plant have a reduced (1,3;1,4)-β-glucan content. The barley plant may carry a mutation in the CsIF6 gene, wherein said mutated CsIF6 gene encodes a mutant CsIF6 polypeptide.

14 Claims, 8 Drawing Sheets

Specification includes a Sequence Listing.

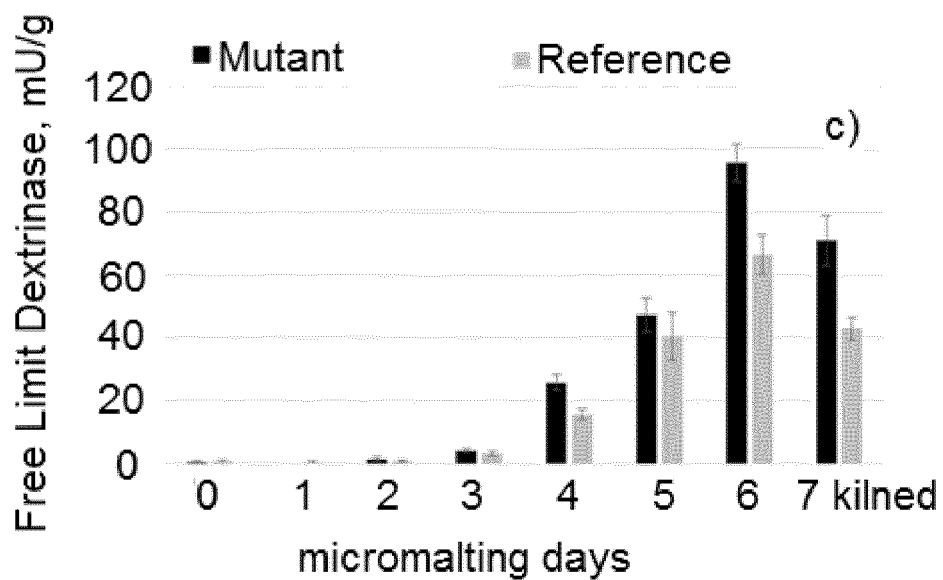
Figure 5 – Cont.

CEREAL PLANTS WITH IMPROVED CELL WALL PROPERTIES

CROSS-REFERENCE TO RELATED APPLICATIONS

This application is a national phase entry pursuant to 35 U.S.C. § 371 of International Application No. PCT/EP2018/086719 filed Dec. 21, 2018, which claims the benefit of priority to European Application No. 17210954.8 filed Dec. 28, 2017, the content of each of which is incorporated by reference herein in their entirety for all purposes.

The present application is filed with a Sequence Listing in electronic ASCII format. The Sequence Listing is provided as a file entitled "2020-06-25_01130-0014-00US_Seq_List_ST25.txt" created on Jun. 25, 2020, which is 36,864 bytes in size. The information in the electronic ASCII format of the sequence listing is incorporated herein by reference in its entirety.

TECHNICAL FIELD

The present invention relates to barley plants having improved cell wall properties. In particular, the invention relates to barley plants having cell wall properties useful for production of barley based beverages, e.g. beer. The invention further relates to methods for production of barley based beverages, as well as to products prepared from the barley plants of the invention.

BACKGROUND

In commercial malting processes, barley grains are germinated, or malted, under controlled conditions that allow partial mobilization of the starch and protein reserves of the starchy endosperm over a period of 4-6 d. The malting process is typically initiated by immersing the dry barley grain in water. This process is known as steeping where the objective is not only to clean the grain, but also to raise its moisture content to about 40-45% (w/w) so that the endosperm mobilization step that follows will occur more quickly. During steeping, the water is drained once to allow re-aeration of the grain. This step is known as the 'air rest' and is considered necessary, primarily because the submerged grain becomes starved of oxygen after about 16 h. After an 'air rest' of about 8 h, the grain is re-immersed in water to complete the steeping treatment over another 8-h period—or in a series of re-steeping steps. The two-step steeping process to increase the moisture content of the dry grain to 40%, or higher, takes about 32 h overall.

The steeped grain is spread for germination, during which enzymes secreted from aleurone and scutellar epithelial cells—together with some that pre-exist in the starchy endosperm cells—degrade cell walls, starch and protein. The maltster usually aims to induce high levels of enzymes that degrade cell wall polysaccharides in the barley grain, in particular the (1,3;1,4)-β-glucans and arabinoxylans. Incompletely degraded (1,3;1,4)-β-glucans can be especially troublesome for brewers, because these can be extracted from the malt in soluble forms that form highly viscous aqueous solutions that slow filtration processes in the brewery and contribute to undesirable haze in the final beer. It has further been shown that brewing with high (1,3;1,4)-β-glucans content negatively affects the level of malt extract. Thus, low levels of soluble (1,3;1,4)-β-glucan represent an important malting quality parameter, while high levels of (1,3;1,4)-β-glucanase enzymes remain important measures of malt quality. In addition, the maltster aims to rapidly induce synthesis of as many of the starch-degrading enzymes in the grains as possible as well. The starch-degrading enzymes—which include α- and β-amylases, starch debranching enzymes (e.g. limit dextrinase) and α-glucosidases—partially depolymerize the starch reserves of the grain to monosaccharides, oligosaccharides, and glucose. The depolymerization products of starch are subsequently used by yeast cells as a carbon source and are fermented into beer ethanol.

As noted above, the germination process typically takes about 5 days. Following the controlled germination steps, the wet malt is dried from about a moisture content of 40% to 4-to-5%. This drying process, termed kilning, is very energy consuming and represents a major cost for the industry. The entire process including kiln drying is typically 6-7 days.

In the brewery, the kiln-dried malt is milled to break open the grain, and the resulting content is extracted with hot water in a process known as mashing. The extracted material includes partially degraded starch, protein and cell wall molecules as described above, and these are further degraded by endogenous grain enzymes that were extracted from the malt. At this stage, some brewers add additional—and generally cheaper carbon sources (adjuncts)—to support the subsequent yeast fermentation process and to offset the higher costs of malt. Said adjuncts can be barley, rice, wheat or other cereal flours from un-germinated grain, but their addition may necessitate the concomitant addition of hydrolytic enzymes, because there are insufficient endogenous enzymes in the malt to degrade the components of the adjunct. The added enzymes are usually from unpurified and relatively cheap extracts of fungal and/or bacterial cultures. The addition of exogenous enzymes is not legal in some countries, particularly where beer must be produced under tightly regulated settings.

Further degradation of the starch, and other endosperm components extracted in hot water, proceed in a process known as saccharification. Following mashing, the extracts are filtered, often in a lauter tun, and cooled. The extract may be boiled in the presence of hops or hop extracts, and upon cooling yeast cultures are added for the fermentation of released sugars to ethanol. The beer so produced is usually matured and filtered before bottling. The beer may also be carbonated prior to bottling.

Barley is the most popular cereal used to produce beer. It is the large amount of starch contained in its kernels that made barley a very attractive raw material for the brewing industry. To ensure that the brewing potential of barley grain is fully utilized it is crucial to have an optimal degradation of the cell wall structures enclosing the starch granules. If simplifying its architecture, the barley kernel is largely constituted of a starchy endosperm surrounded by an aleurone layer. The barley kernel aleurone and endosperm cell walls are mainly composed of non-starch polysaccharides (NSP). The starchy endosperm consists of 75% of (1-3,1-4)-β-glucans (BGL) and 20% of arabinoxylan (AX), while the aleurone is composed of 71% of AX and 26% of BGL. Barley BGLs are unbranched, long linear chains of glucose residues linked through both β-(1-3) and β-(1-4)-linkages. Barley AX consists of a D-xylanopyranosyl molecular backbone linked by β-(1,4) bonds, randomly with connected L-arabinofuranose though α-(1-2) and α-(1-3) linkages.

SUMMARY

As outlined above, one of the time and energy consuming steps of beer production is malting. A rate limiting step in the malting procedure is the reduction of the levels of (1,3;1,4)-β-glucans in the germinating barley kernels to acceptable low levels. Accordingly, there is a need for the provision of materials and methods, which can reduce the time required for malting. In particular, there is a need for barley plants with low levels of (1,3;1,4)-β-glucans. However, barley plants with a complete absence of (1,3;1,4)-β-glucans have reduction in plant height, plant vigour and yield (approximately 70% of the control) (Taketa et al., 2012). In fact, Taketa et al. concludes that "as the agronomic characteristics are reduced, the utility of the bgl mutants in malting may not be good . . . ". Hu et al. (2014) describes a barley mutant m351 comprising very low levels of mixed-linkage (1-3,1-4) β-glucan (<1.6%). However the m351 mutant exhibited reduced grain hardness as shown by a more than four-fold increase in grain breakage rate compared to its parent, and sensitivity to salts resulting in weaker germination under 400 mM salt condition.

Accordingly, there is a need for barley plants with low levels of (1,3;1,4)-β-glucans, which at the same time have good agronomic characteristics and grain hardness.

Barley (1,3;1,4)-β-glucans comprises cellotriosyl (DP3) and cellotetraosyl (DP4) residues in ratios, which typically are in the range of 2.5 to 4. The DP3/DP4 ratio has an impact on the properties of (1,3;1,4)-β-glucans.

In one embodiment the invention provides barley plants having a low level of (1,3;1,4)-β-glucans with a DP3/DP4 ratio comparable to the DP3/DP4 ratio of wild type barley. Such barley plants may be agronomical sound and have barley grains with reduced tendency to breakage. One technical problem solved by the present invention is the provision of barley plants having a low level of (1,3;1,4)-β-glucans, wherein the barley plants at the same time have acceptable agronomical traits, an acceptable frequency of breakage of the grains (e.g. <2 times that of wild type plant without CslF6 mutation, but otherwise of the same genotype) and in addition a DP3/DP4 ratio similar to wild type barley.

In one embodiment the invention provides barley plants having a low level of (1,3;1,4)-β-glucans with a high or a low DP3/DP4 ratio. Such barley plants may have agronomical sound grains and they may have a higher level of insoluble (1,3;1,4)-β-glucans. Insoluble (1,3;1,4)-β-glucans can potentially be removed during brewing processes, and are thus in some embodiments preferable. Burton & Fincher 2014 has speculated that the solubility of the (1,3;1,4)-β-glucans molecules may be predicted from the DP3:DP4 ratio, and that high and low ratios may result in more insoluble aggregates.

Jobling et al. (2015) describes expression of CslF in an artificial system in Tobacco leaf and describe that a single amino acid (Ile757) in the fourth transmembrane domain of CslF controls the DP3:DP4 ratio, however neither modification of that domain nor the DP3:DP4 ratio are described to correlate with the amount of (1,3;1,4)-β-glucans.

One technical problem solved by the present invention is the provision of barley plants having a low level of (1,3;1,4)-β-glucans, wherein the barley plants at the same time have acceptable agronomical traits and in addition a useful DP3/DP4 ratio.

In one aspect the invention provides barley plants carrying a mutation of single amino acids in the transmembrane domains. The invention surprisingly demonstrates that such barley plants comprise a low level of (1,3;1,4)-β-glucans (typically in the range of 1.7 to 5%) are viable, are agronomical sound and have yields comparable with other barley cultivars. Such barley plants are particularly useful for methods of production of cereal based beverages with reduced germination time.

Furthermore, the present invention provides methods and tools for providing barley plants with fine-tuned (1,3;1,4)-β-glucan content. Thus, the barley plants of the invention not only have a low (1,3;1,4)-β-glucan content, but the DP3:DP4 ratio of the barley plants may also be controlled.

In one aspect the present invention provides a barley plant or a part thereof, wherein the kernels of said barley plant have a reduced (1,3;1,4)-β-glucan content, and wherein said barley plant carries a mutation in the CslF6 gene, wherein said mutated CslF6 gene encodes a mutant CslF6 polypeptide, wherein said mutant CslF6 is CslF6 of SEQ ID NO:1 or SEQ ID NO:3 except that mutant CslF6 comprises a substitution of one amino acid in a membrane localised domain of CslF6, wherein said substitution is substitution of a non-polar amino acid to a charged amino acid or substitution of a polar amino acid to a non-polar amino acid, wherein the membrane localised domains of CslF6 consists of amino acids 109 to 128, 137 to 158, 700 to 731, 741 to 758, 835 to 857, and 864 to 882 of SEQ ID NO:1 or SEQ ID NO:3.

It is also an aspect of the invention to provide plant products prepared from said barley plant as well as methods of preparing plant products from said barley plant. The barley plants of the present invention can advantageously be used to prepare plant products, for example wort, with a reduced viscosity compared to wort prepared from kernels of a barley plant carrying a wild type CslF6 gene, but otherwise of the same genotype of the barley plant of barley plants of the invention.

DETAILED DESCRIPTION

Definitions

Figure 1:
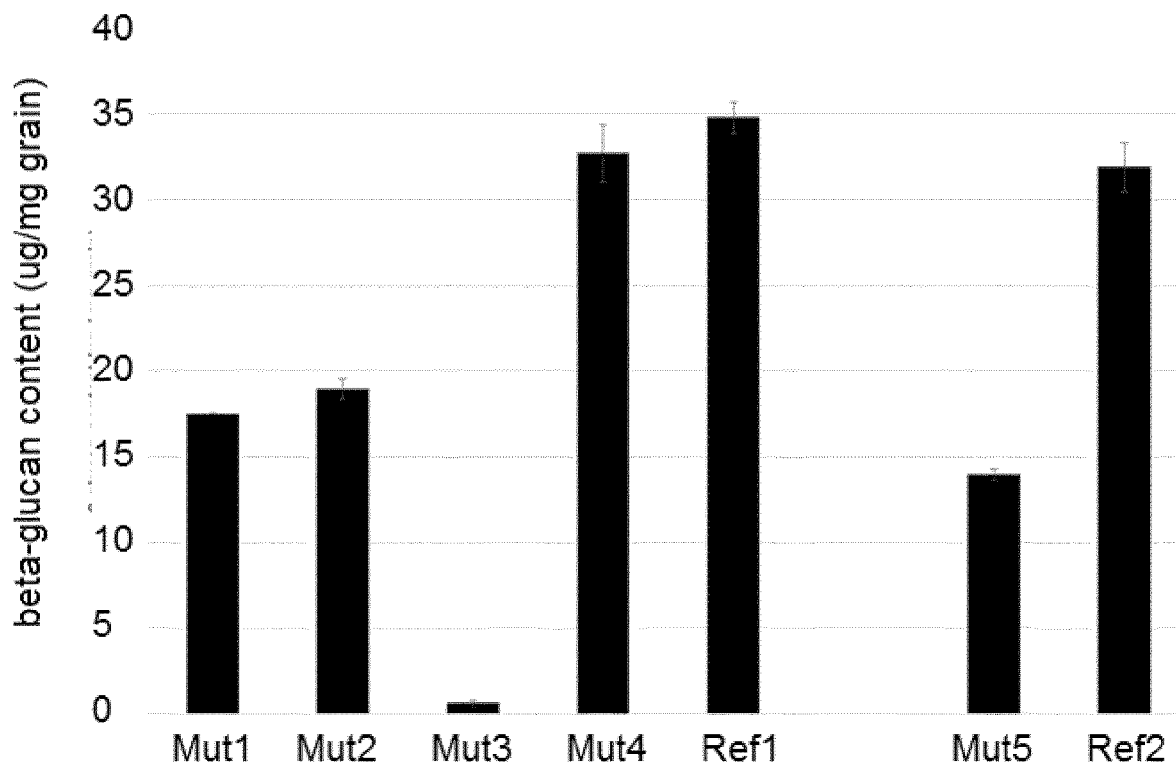
FIG. 1. (1,3;1,4)-β-glucan (abbreviated β-glucan or BGL) content of mutants identified either by the Digital Mutation Identification (DMI) method (Mut1, 2, 3 and 4 with corresponding reference 1) or by sequencing (Mut5 and corresponding reference). The bars represent +/−SD FIG. 2. DP3:DP4 ratio of mutants identified either by the DMI method (Mut1, 2, 3, 4 with corresponding reference 1) or by sequencing (Mut5 and corresponding reference).

As used herein, "a" can mean one or more, depending on the context in which it is used.

The term "adjunct" as used herein refers to carbon-rich raw material sources added during preparation of beer. The adjunct may be an ungerminated cereal grain, which may be milled together with the germinated grains prepared according to the invention. The adjunct may also be a syrup, sugar or the like.

The term "amino acid" as used herein refers to a proteinogenic amino acid. Preferably, the proteinogenic amino acids is one of the 20 amino acids encoded by the standard genetic code. The IUPAC one and three letter codes are used to name amino acids.

The term "amino acid corresponding to X" is used herein to describe amino acids of a given polypeptide (e.g. a mutant CslF6 polypeptide) in relation to amino acids of a reference polypeptide (e.g. CslF6 of SEQ ID NO:1). Following alignment between said polypeptide and the reference polypeptide, an amino acid is corresponding to X if it is in the same position as X in said alignment.

The term "amylose" refers to homopolymers of α-D-glucose. Amylose has a linear molecular structure, as its glucose units are almost exclusively linked by α-1-4-glycosidic bonds.

The term "amylopectin" refers to homopolymers of α-D-glucose. Amylopectin molecules contain frequent α-1-6-glycosidic linkages. These introduce branch points into the otherwise α-1-4-linked glucose chains resulting in clusters of parallel chains appearing in regular intervals along the molecule's axis.

The term "approximately" when used herein in relation to numerical values preferably means ±10%, more preferably ±5%, yet more preferably ±1%.

The term "barley" in reference to the process of making barley based beverages, such as beer, particularly when used to describe the malting process, means barley kernels.

In all other cases, unless otherwise specified, "barley" means the barley plant (*Hordeum vulgare*, L.), including any breeding line or cultivar or variety, whereas part of a barley plant may be any part of a barley plant, for example any tissue or cells.

The term "barley flour" as used herein refers to milled barley kernels.

A "cereal" plant, as defined herein, is a member of the Poaceae plant family, cultivated primarily for their starch-containing seeds or kernels. Cereal plants include, but are not limited to barley (*Hordeum*), wheat (*Triticum*), rice (*Oryza*), maize (*Zea*), rye (*Secale*), oat (*Avena*), sorghum (Sorghum), and Triticale, a rye-wheat hybrid.

The term "charged amino acid" as used herein refers to amino acids with electrically charged side chains. Preferably, the charged amino acid is selected from the group consisting of Arg, His, Lys, Asp and Glu. Negatively charged amino acids are preferably selected from the group consisting of Asp and Glu.

The term "chit" as used herein refers to the embryonic growing bud that is visible during the germination phase of a cereal grain.

The term "α-amylase"

The term "DP" as used herein refers to the degree of polymerization, and indicates the number of α-1,4-linked glucose units in amylopectin side chains. Thus, by way of example DP3 refers to amylopectin side chains consisting of a sequence of 3 α-1,4-linked glucose units. Similarly, DP4 refers to amylopectin side chains consisting of a sequence of 4 α-1,4-linked glucose units. The term "DP3:DP4 ratio" of (1,3;1,4)-β-glucans as used herein refers to the ratio of amylopectin side chains consisting of a sequence of 3 α-1,4-linked glucose units and of amylopectin side chains consisting of a sequence of 4 α-1,4-linked glucose units within said (1,3;1,4)-β-glucans. The DP3:DP4 ratio may be determined by digesting (1,3;1,4)-β-glucans with lichenase followed by quantification of released DP3 and DP4 oligomers e.g. by HPAEC-PAD. In particular, the DP3:DP4 ratio may be determined as described in Example 3.

By "encoding" or "encoded", in the context of a specified nucleic acid, is meant comprising the information for translation into the specified protein. A nucleic acid or polynucleotide encoding a protein may comprise non-translated sequences, e.g. introns, within translated regions of the nucleic acid, or may lack such intervening non-translated sequences, e.g. in cDNA. The information by which a protein is encoded is specified by the use of codons.

As used herein, "expression" in the context of nucleic acids is to be understood as the transcription and accumulation of mRNA. "Expression" used in the context of proteins refers to translation of mRNA into a polypeptide.

The term "gene" means the segment of DNA involved in producing a polypeptide chain; it includes regions preceding and following the coding region (promoter and terminator). Furthermore, plant genes generally consist of exons interrupted by introns.

The term "germinated grain" as used herein refers to a grain having developed a visible chit and a visible stem.

The term "initiation of germination" as used herein refers to the time point at which barley grains with a water content of less than 15% is contacted with sufficient water to initiate germination.

The term "β-glucanase" as used herein refers to enzymes with the potential to depolymerize cereal β-glucan. Accordingly, unless otherwise specified, the term "β-glucanase" refers to an endo- or exo-enzyme or mixture thereof characterized by (1,3;1,4)-β- and/or (1,4)-β-glucanase activity.

"(1,3;1,4)-β-glucan content" as used herein may be determined by any useful method. Preferably, the "(1,3;1,4)-β-glucan content" is determined as the sum of the content of Glc-β-(1→4)-Glc-β-(1→3)-Glc (DP3) and Glc-β-(1→4)-Glc-β-(1→4)-Glc-β-(1→3)-Glc (DP4) oligomers. The content of DP3 and DP4 oliogmers may e.g. be determined by lichenase digestion of (1,3;1,4)-β-glucans followed by quantification e.g. by High-performance anion exchange chromatography with pulsed amperometric detection (HPAEC-PAD). Preferably, (1,3;1,4)-β-glucan content is determined as described herein below in Example 3.

The term "(1,3;1,4)-β-glucan synthase" as used herein should be regarded as any protein which catalyses the synthesis of (1,3;1,4)-β-glucan and, optionally, catalyses the polymerisation of glucopyranosyl monomers. For example the (1,3;1,4)-β-glucan synthase may be a polypeptide encoded by a CslF gene or a functional homolog thereof.

The term "kernel" is defined to comprise the cereal caryopsis, also denoted internal seed. In addition, the kernel may comprise the lemma and palea. In most barley varieties, the lemma and palea adhere to the caryopsis and are a part of the kernel following threshing. However, naked barley varieties also occur. In these, the caryopsis is free of the lemma and palea and threshes out free as in wheat. The terms "kernel" and "grain" are used interchangeably herein.

The term "malting" as used herein refers to a controlled germination of cereal kernels (in particular barley kernels)

taking place under controlled environmental conditions. In some embodiments "malting" may further comprise a step of drying said germinated cereal kernels, e.g. by kiln drying.

The term "green malt" as used herein refers germinated cereal kernels, which have not been subjected to a step of kiln drying. In general, said cereal kernels have been germinated under controlled environmental conditions. In some embodiments the green malt is milled green malt.

The term "kiln dried malt" as used herein refers germinated cereal kernels, which have been dried by kiln drying. In general, said cereal kernels have been germinated under controlled environmental conditions. In some embodiments the kiln dried malt is milled kiln dried malt.

"Mashing" is the incubation of milled malt (e.g. green malt or kiln dried malt), and/or ungerminated cereal kernels in water. Mashing is preferably performed at specific temperature(s), and in a specific volume of water.

"Mutations" include deletions, insertions, substitutions, transversions, and point mutations in the coding and non-coding regions of a gene. Deletions may be of the entire gene, or of only a portion of the gene. Point mutations may concern changes of one base pair, and may for result in premature stop codons, frameshift mutations, mutation of a splice site or amino acid substitutions. A gene comprising a mutation may be referred to as a "mutant gene". If said mutant gene encodes a polypeptide with a sequence different to the wild type, said polypeptide may be referred to as a "mutant polypeptide".

The term "milled" refers to material (e.g. barley kernels or malt), which has been finely divided, e.g. by cutting, milling, grinding or crushing. The barley kernels can be milled while moist using e.g. a grinder or a wet mill. Milled barley kernels or milled malt is sufficiently finely divided to render the material useful for aqueous extracts. Milled barley kernels or milled malt cannot be regenerated into an intact plant by essentially biological methods.

The term "non-polar amino acid" as used herein refers to amino acids with a hydrophobic side chains. Preferably, the non-polar amino acid is selected from the group consisting of Ala, Val, Ile, Leu, Met, Phe, Tyr, Trp and Gly, more preferably from the group consisting of Ala, Val, Ile, Leu, Met, Phe, Trp and Gly.

By the term "plant product" is meant a product resulting from the processing of a plant or plant material. Said plant product may thus, for example, be green malt, kiln dried malt, wort, a fermented or non-fermented beverage, a food, or a feed product.

The term "polar amino acid" as used herein refers to amino acids with polar, uncharged side chains. Preferably, the polar amino acid is selected from the group consisting of Ser, Thr, Asn and Gln.

By the term "progeny" as used herein is meant a plant, which directly or indirectly is off-spring of a given plant. Thus, progeny is not confined to direct off-spring but also includes off-spring after numerous generations. In general, progeny of a barley plant carrying a specific mutation also carries that specific mutation. Thus, progeny of a barley plant carrying a specific mutation in the CslF6 gene also carry that specific mutation.

The term "sequence identity" as used herein refers to the % of identical amino acids or nucleotides between a candidate sequence and a reference sequence following alignment. Thus, a candidate sequence sharing 80% amino acid identity with a reference sequence requires that, following alignment, 80% of the amino acids in the candidate sequence are identical to the corresponding amino acids in the reference sequence. Identity according to the present invention is determined by aid of computer analysis, such as, without limitations, the Clustal Omega computer alignment program for alignment of polypeptide sequences (Sievers et al. (2011 Oct. 11) Molecular Systems Biology 7:539, PM ID: 21988835; Li et al. (2015 Apr. 6) Nucleic Acids Research 43 (W1):W580-4 PMID: 25845596; McWilliam et al., (2013 May 13) Nucleic Acids Research 41 (Web Server issue): W597-600 PMID: 23671338, and the default parameters suggested therein. The Clustal Omega software is available from EMBL-EBI at ebi.ac.uk. Using this program with its default settings, the mature (bioactive) part of a query and a reference polypeptide are aligned. The number of fully conserved residues are counted and divided by the length of the reference polypeptide. The MUSCLE or MAFFT algorithms may be used for alignment of nucleotide sequences. Sequence identities may be calculated in a similar way as indicated for amino acid sequences. Sequence identity as provided herein is thus calculated over the entire length of the reference sequence.

The term "starch" as used herein refers to a composition of one or both of the discrete macromolecules: amylose and amylopectin.

The term "steeping" as used herein refers to the process of increasing the water content of a cereal kernel.

The term "water content" of a grain as used herein refers to the % of $H_2O$ w/w in said grain.

The term "wild type CslF6" as used herein refers to a gene encoding a polypeptide of SEQ ID NO:1 or SEQ ID NO:3.

Enzyme activities of cereal grains as used herein refer to the activities measured in flour prepared from the specified grain type. For example, 10 U/g of α-amylase activity per gram cereal grain refers to said α-amylase activity (10 U) measured in an aqueous extract derived from 1 g of flour (dry matter) from said cereal. α-amylase activity is determined by K-CERA 01/12 (protocol and kit available from Megazyme, Ireland). β-amylase activity is determined by the K-BETA3 (protocol and kit available from Megazyme, Ireland). Limit-dextrinase activity is determined by the T-LDZ1000 (protocol and kit available from Megazyme, Ireland).

The volume of a gas as indicated herein refers to the volume of said gas at 1 atm and 20° C.

The volume of $O_2$ as indicated herein refers to the volume of $O_2$ at 1 atm and 20° C. In embodiments of the invention where $O_2$ is comprised in a mixture of gasses, then the total volume of the gas mixture may be determined, and the volume of $O_2$ may be calculated as the percentage of the total volume constituted by $O_2$. By way of example then atmospheric air comprises 21% $O_2$. Thus the volume of $O_2$ within atmospheric air as used herein is 21% of the total volume of atmospheric air.

By the term "wort" is meant a liquid extract of malt and/or cereal kernels, such as milled malt and/or milled cereal kernels and optionally additional adjuncts. Wort is in general obtained by mashing, optionally followed by "sparging", in a process of extracting residual sugars and other compounds from spent grains after mashing with hot water. Sparging is typically conducted in a lauter tun, a mash filter, or another apparatus to allow separation of the extracted water from spent grains. The wort obtained after mashing is generally referred to as "first wort", while the wort obtained after sparging is generally referred to as the "second wort". If not specified, the term wort may be first wort, second wort, or a combination of both. During conventional beer production, wort is boiled together with hops. Wort without hops, may also be referred to as "sweet wort", whereas wort boiled with hops may be referred to as "boiled wort" or simply as wort.

CslF6

The present invention provides a barley plant or a part thereof, wherein the kernels of said barley plant has a reduced (1,3;1,4)-β-glucan content, wherein said barley plant carries a mutation in the CslF6 gene and wherein said mutated CslF6 gene encodes a mutant CslF6 polypeptide.

The sequence of a wild type cellulose synthase-like CslF6 (CslF6) complete coding sequence from barley *Hordeum vulgare* cultivar Sloop is provided herein as SEQ ID NO:2.

The sequence of a wild type cellulose synthase-like CslF6 polypeptide sequence from barley *Hordeum vulgare* cultivar Sloop is provided herein as SEQ ID NO:1. A. In addition to the sequence provided herein as SEQ ID NO:1, wild type CslF6 polypeptide may also carry an A590T polymorphism (Taketa et al. (2012)). Accordingly, the wild type CslF6 polypeptide may also have the sequence provided herein as SEQ ID NO:3.

Despite significant research effort, the particular functions of individual Csl genes are largely unknown. The Csl genes have been sub-divided into eight groups designated CslA to CslH. In accordance with the present invention, it has been revealed that (1,3;1,4)-β-glucan synthases are encoded by members of the CslF gene family.

Barley Plant Carrying a Mutation in the CslF6 Gene

The present invention provides a barley plant or a part thereof, wherein the kernels of said barley plant has a reduced (1,3;1,4)-β-glucan content, wherein said barley plant carries a mutation in the CslF6 gene and wherein said mutated CslF6 gene encodes a mutant CslF6 polypeptide. The mutation in the CslF6 gene may be any of the mutations described herein, however in preferred embodiments of the invention the mutation is a point mutation in the coding region of the CslF6 gene.

The mutant CslF6 polypeptide encoded by said mutant CslF6 gene may be any mutant CslF6 polypeptide, however preferably said mutant CslF6 polypeptide contain one amino acid substitution.

In particular, the mutant CslF6 polypeptide may comprise a substitution of one amino acid in a membrane localised domain of CslF6. The mutant CslF6 polypeptide may preferably comprise one or more of the following substitutions in a membrane localised domain:
  substitution of a non-polar amino acid to a charged amino acid; and
  substitution of a polar amino acid to a non-polar amino acid.

As used herein the terms "substitution of amino acid XX for amino acid YY" or "substitution of amino acid XX to amino acid YY" refers to amino acid XX in a reference sequence (typically the CslF6 wild type sequence) being replaced by amino acid YY.

In one embodiment of the invention, the mutant CslF6 polypeptide may comprise a substitution of one amino acid in any one of the membrane localised domain of CslF6. The membrane localised domains of CslF6 are shown herein in Table 3.

In one embodiment, the mutant CslF6 polypeptide may comprise a substitution of a non-polar amino acid to a charged amino acid, in one or more of the following membrane localized domains of CslF6: amino acids 109 to 128, 137 to 158, 700 to 731, 741 to 758, 835 to 857, and 864 to 882 of SEQ ID NO:1 OR SEQ ID NO:3.

In one embodiment, the barley plant carries a mutation in the CslF6 gene resulting in a mutant CslF6 gene encoding a mutant CslF6 polypeptide comprising a substitution, wherein the substitution may be substitution of a non-polar amino acid to a charged amino acid, in one or more of the following membrane localized domains of CslF6: amino acids 109 to 128, 137 to 158, 700 to 731, 741 to 758, 835 to 857, and 864 to 882 of SEQ ID NO:1 or SEQ ID NO:3.

In one embodiment the mutant CslF6 polypeptide may be CslF6 of SEQ ID NO:1 or SEQ ID NO:3 except that mutant CslF6 comprises a substitution of one amino acid in the transmembrane domain consisting of amino acids 835 to 857 of CslF6, wherein said substitution is substitution of a non-polar amino acid to a charged amino acid. Said non-polar amino acid may for example be any one of amino acids 835 to 857, which are underlined in Table 3. For example said substitution may be a substitution of a non-polar amino acid to a negatively charged amino acid.

For example the mutant CslF6 polypeptide may be CslF6 of SEQ ID NO:1 or SEQ ID NO:3 except that mutant CslF6 comprises a substitution of amino acid 847 to a charged amino acid. For example said substitution may be a substitution of glycine (G) in position 847 to a negatively charged amino acid, e.g. Glu or Asp.

Preferably the mutant CslF6 polypeptide may be CslF6 of SEQ ID NO:1 or SEQ ID NO:3 except that mutant CslF6 comprises a substitution of amino acid 847, wherein said substitution is substitution of the glycine (G) in position 847 to a glutamic acid (E).

In one embodiment the mutant CslF6 polypeptide may be CslF6 of SEQ ID NO:1 or SEQ ID NO:3 except that mutant CslF6 comprises a substitution of one amino acid in the transmembrane domain consisting of amino acids 741 to 758 of CslF6, wherein said substitution is substitution of a non-polar amino acid to a charged amino acid. Said non-polar amino acid may for example be any one of amino acids 741 to 758, which are underlined in Table 3. For example said substitution may be a substitution of a non-polar amino acid to a negatively charged amino acid.

For example the mutant CslF6 polypeptide may be CslF6 of SEQ ID NO:1 or SEQ ID NO:3 except that mutant CslF6 comprises a substitution of amino acid 748 to a charged amino acid. For example said substitution may be a substitution of glycine (G) in position 748 to a negatively charged amino acid, e.g. Glu or Asp. Preferably the mutant CslF6 polypeptide may be CslF6 of SEQ ID NO:1 or SEQ ID NO:3 except that mutant CslF6 comprises a substitution of amino acid 748, wherein said substitution is substitution of the glycine (G) in position 748 to an aspartic acid (D). Thus, the barley plant may carry a mutated HvCslF6 gene encoding a mutant HvCslF6 protein comprising a Gly→Asp mutation of amino acid 748 of SEQ ID NO:1.

In one embodiment, the barley plant may carry a G→A mutation of nucleotide 2243 of the coding sequence of the HvCslF6 gene (SEQ ID NO 2).

In one embodiment, the mutant CslF6 polypeptide may comprise a substitution of one amino acid in any one of the membrane localised domain of CslF6. For example the substitution may be substitution of a polar amino acid to a non-polar amino acid, in one or more of the following membrane localized domains of CslF6: amino acids 109 to 128, 137 to 158, 700 to 731, 741 to 758, 835 to 857, and 864 to 882 of SEQ ID NO:1 or SEQ ID NO:3.

The mutant CslF6 polypeptide may be CslF6 of SEQ ID NO:1 or SEQ ID NO:3 except that mutant CslF6 comprises a substitution of one amino acid in the transmembrane domain consisting of amino acids 700 to 731 of CslF6, wherein said substitution is substitution of a polar amino acid to a non-polar amino acid. Said polar amino acid may for example be any one of amino acids 700 to 731, which is underlined in Table 3.

For example the mutant CslF6 polypeptide may be CslF6 of SEQ ID NO:1 or SEQ ID NO:3 except that mutant CslF6 comprises a substitution of amino acid 709 to a non-polar amino acid.

Preferably the mutant CslF6 polypeptide may be CslF6 of SEQ ID NO:1 or SEQ ID NO:3 except that mutant CslF6 comprises a substitution of amino acid 709, wherein said substitution is substitution of the threonine (T) in position 709 to a isoleucine (I).

For the purposes of this patent application seeds of barley plant (*Hordeum vulgare*) designated "Mutant 2" has been deposited with NCIMB Ltd. Ferguson Building, Craibstone Estate, Bucksburn, Aberdeen, AB21 9YA Scotland under the provisions of the Budapest Treaty. The Mutant 2 barley plant was deposited on 12 Nov. 2018 and has received the accession number NCIMB 43273.

In one embodiment, the barley plant of the invention is the barley plant (*Hordeum vulgare*) deposited on 12-10-2018 with NCIMB under the accession number NCIMB 43273 and referred to as "Mutant 2"; or progeny thereof. Thus, the barley plant of the invention may be barley plant Mutant 2 deposited with NCIMB on 12-10-2018 and having accession number NCIMB 43273, or any progeny barley plant thereof, wherein the barley plant carries a G→A mutation of nucleotide 2243 of the coding sequence of the HvCslF6 gene (SEQ ID NO 2) and/or wherein the HvCslF6 gene of said barley plant encodes a mutant HvCslF6 protein comprising a Gly→Asp mutation of amino acid 748 of SEQ ID NO:1.

Interestingly, a barley plant carrying a mutation in the CslF6 gene leading to a mutant CslF6 gene encoding a mutant CslF6 polypeptide carrying a mutation outside of the membrane localised amino acids (G732D) did not show any significant reduction in (1,3;1,4)-β-glucan content. In a barley plant comprising a mutation in the CslF6 gene leading to a premature stop codon (T676Stop) the levels of (1,3;1,4)-β-glucan were extremely low and such barley plants did not have good agronomic properties. Thus, such plants had significantly reduced fertility and plant growth.

Barley Plant

The barley plant according to the invention may be any plant of the species *Hordeum vulgare*, including any breeding line or cultivar or variety.

"Wild barley", *Hordeum vulgare* ssp. *spontaneum*, is considered the progenitor of today's cultivated forms of barley. Domesticated, but heterogeneous mixtures of barley are referred to as barley landraces. Today, most of the landraces have been displaced in advanced agricultures by pure line cultivars. Compared with landraces, modern barley cultivars have numerous improved properties (Nevo, 1992; Pelger et al., 1992).

Within the present invention, the term "barley plant" comprises any barley plant, such as barley landraces or modern barley cultivars. Thus, the invention relates to any barley plant comprising a mutation in the CslF6 gene.

However, preferred barley plants for use with the present invention are modern barley cultivars or pure lines. The barley cultivar to be used with the present invention may, for example, be selected from the group consisting of Paustian, Sebastian, Quench, Celeste, Lux, Prestige, Saloon, Neruda, Harrington, Klages, Manley, Schooner, Stirling, Clipper, Franklin, Alexis, Blenheim, Ariel, Lenka, Maresi, Steffi, Gimpel, Cheri, Krona, Camargue, Chariot, Derkado, Prisma, Union, Beka, Kym, Asahi 5, KOU A, Swan Hals, Kanto Nakate Gold, Hakata No. 2, Kirin-choku No. 1, Kanto late Variety Gold, Fuji Nijo, New Golden, Satukio Nijo, Seijo No. 17, Akagi Nijo, Azuma Golden, Amagi Nijpo, Nishino Gold, Misato golden, Haruna Nijo, Scarlett, Rosalina and Jersey preferably from the group consisting of Haruna Nijo, Sebastian, Quench, Celeste, Lux, Prestige, Saloon, Neruda and Power, preferably from the group consisting of Paustian, Harrington, Klages, Manley, Schooner, Stirling, Clipper, Franklin, Alexis, Blenheim, Ariel, Lenka, Maresi, Steffi, Gimbel, Cheri, Krona, Camargue, Chariot, Derkado, Prisma, Union, Beka, Kym, Asahi 5, KOU A, Swan Hals, Kanto Nakate Gold, Hakata No. 2, Kirin-choku No. 1, Kanto late Variety Gold, Fuji Nijo, New Golden, Satukio Nijo, Seijo No. 17, Akagi Nijo, Azuma Golden, Amagi Nijpo, Nishino Gold, Misato golden, Haruna Nijo, Scarlett and Jersey preferably from the group consisting of Paustian, Haruna Nijo, Sebastian, Tangent, Lux, Prestige, Saloon, Neruda, Power, Quench, NFC Tipple, Berke, Class, Vintage, Applaus, Bowie, Broadway, Champ, Chanson, Charles, Chimbon, Cosmopolitan, Crossway, Dragoon, Ellinor, Embrace, Etoile, Evergreen, Flair, Highway, KWS Beckie, KWS Cantton, KWS Coralie, KWS Fantex, KWS Irina, KWS Josie, KWS Kellie, LG Diablo, LG Figaro, LG Nabuco, LG Tomahawk, Laureate, Laurikka, Lauxana, Luther, Odyssey, Ovation, Prospect, RGT Elysium, RGT Observer, RGT Planet, Rotator, Sarbi, Scholar, Subway and Golden Promise.

The barley plant may be in any suitable form. For example, the barley plant according to the invention may be a viable barley plant, a dried plant, a homogenized plant, or a milled barley kernel. The plant may be a mature plant, an embryo, a kernel, a germinated kernel, a malted kernel (e.g. in the form of green malt or kiln dried malt), a milled malted kernel, a milled kernel or the like.

Parts of barley plants may be any suitable part of the plant, such as kernels, embryos, leaves, stems, roots, flowers, or fractions thereof. A fraction may, for example, be a section of a kernel, embryo, leaf, stem, root, or flower. Parts of barley plants may also be a fraction of a homogenate or a fraction of a milled barley plant or kernel.

In one embodiment of the invention, parts of barley plants may be cells of said barley plant, such as viable cells that may be propagated in vitro in tissue cultures. In other embodiments, however, the parts of barley plants may be viable cells that are not capable of maturing into an entire barley plant, i.e. cells that are not a reproductive material.

Characteristics of Barley Plants Carrying a Mutation in CslF6

The invention provides barley plants carrying a mutation in the CslF6 gene. One major advantage of such barley plants is that the kernels of said barley plant have a reduced (1,3;1,4)-β-glucan content.

One advantage provided by the barley plants carrying a mutation in the CslF6 gene and having reduced (1,3;1,4)-β-glucan content is that the lower content of (1,3;1,4)-β-glucan in the grain may be beneficial in the brewing process as it may help securing that the optimal amount of sugars are available for yeast fermentation at the end of mashing and therefore reduce the total cost of the raw material. Another advantage provided by the barley plants carrying a mutation in the CslF6 gene and having kernels with reduced (1,3;1,4)-β-glucan content is that the low (1,3;1,4)-β-glucan barley may improve industrial procedures such as filterability. Furthermore, such barley plants are particularly useful for energy saving malting processes. Whereas reduction in (1,3;1,4)-β-glucan may be beneficial, a too low levels of (1,3;1,4)-β-glucan may also be problematic and can result in poorer agronomic properties.

Thus, in one embodiment the barley plant carrying a mutation in the CslF6 gene may be a barley plant with kernels having (1,3;1,4)-β-glucan content in the range of 1 to 3% dry weight of total kernels.

The barley plants of the invention carrying a mutation in the CslF6 gene and having kernels with a reduced (1,3;1,4)-β-glucan content are further characterized by having good agronomical qualities, such as agronomical qualities comparable to the wild type.

The barley plant, may be a barley plant with kernels having a (1,3;1,4)-β-glucan content in the range of 1 to 5% dry weight of total kernels, for example 1 to 3% dry weight of total kernels, such as 1.3 to 4% dry weight of total kernels, for example 1.3 to 3% dry weight of total kernels, preferably 1.3 to 2% dry weight of total kernels.

In one embodiment, the barley plant may be a barley plant carrying a mutation in the CslF6 gene and encoding a mutant CslF6 polypeptide, wherein the CslF6 polypeptide is a CslF6 polypeptide of SEQ ID NO:1 or SEQ ID NO:3 except that mutant CslF6 comprises a substitution of one amino acid in one or more of the following membrane localized domains of CslF6: amino acids 109 to 128, 137 to 158, 700 to 731, 741 to 758, 835 to 857, and 864 to 882 of SEQ ID NO:1 or SEQ ID NO:3, wherein the substitution is a substitution of a non-polar amino acid to a charged amino acid or substitution of a polar amino acid to a non-polar amino acid and wherein the kernels of said barley plant may have a (1,3;1,4)-β-glucan content in the range of 1.0 to 3.0 dry weight of total kernels, for example a (1,3;1,4)-β-glucan content in the range of 1.0 to 3.0% dry weight of total kernels, such as a (1,3;1,4)-β-glucan content in the range of 1.0 to 2.5% dry weight of total kernels, preferably a (1,3;1,4)-β-glucan content in the range of 1.0 to 2.0% dry weight of total kernels, for example a (1,3;1,4)-β-glucan content in the range of 1.3 to 3.0% dry weight of total kernels, such as a (1,3;1,4)-β-glucan content in the range of 1.5 to 3.0% dry weight of total kernels, preferably a (1,3;1,4)-β-glucan content in the range of 1.7 to 3.0% dry weight of total kernels.

In one embodiment, the barley plant may be a barley plant carrying a mutation in the CslF6 gene and encoding a mutant CslF6 polypeptide, wherein the CslF6 polypeptide is a CslF6 polypeptide of SEQ ID NO:1 or SEQ ID NO:3 except that mutant CslF6 comprises a substitution of amino acid 847, wherein said substitution is substitution of a glycine (G) to a glutamic acid (E), and the kernels of said barley plant may have a (1,3;1,4)-β-glucan content in the range of 1.0 to 3.0 dry weight of total kernels, for example a (1,3;1,4)-β-glucan content in the range of 1.0 to 3.0% dry weight of total kernels, such as a (1,3;1,4)-β-glucan content in the range of 1.0 to 2.5% of the dry weight of total kernels, preferably a (1,3;1,4)-β-glucan content in the range of 1.0 to 2.0 of the dry weight of total kernels, for example a (1,3;1,4)-β-glucan content in the range of 1.3 to 3.0% dry weight of total kernels, such as a (1,3;1,4)-β-glucan content in the range of 1.5 to 3.0% dry weight of total kernels, preferably a (1,3;1,4)-β-glucan content in the range of 1.7 to 3.0% of the dry weight of total kernels.

In one embodiment, the barley plant may be a barley plant carrying a mutation in the CslF6 gene and encoding a mutant CslF6 polypeptide, wherein the CslF6 polypeptide is a CslF6 polypeptide of SEQ ID NO:1 or SEQ ID NO:3 except that mutant CslF6 comprises a substitution of amino acid 748, wherein said substitution is substitution of a glycine (G) for an aspartic acid (D), and the kernels of said barley plant may have a (1,3;1,4)-β-glucan content in the range of 1.0 to 3.0 dry weight of total kernels, for example a (1,3;1,4)-β-glucan content in the range of 1.0 to 3.0% dry weight of total kernels, such as a (1,3;1,4)-β-glucan content in the range of 1.0 to 2.5% dry weight of total kernels, preferably a (1,3;1,4)-β-glucan content in the range of 1.0 to 2.0%, for example a (1,3;1,4)-β-glucan content in the range of 1.3 to 3.0% dry weight of total kernels, such as a (1,3;1,4)-β-glucan content in the range of 1.5 to 3.0% dry weight of total kernels, preferably a (1,3;1,4)-β-glucan content in the range of 1.7 to 3.0% dry weight of total kernels.

In one embodiment, the barley plant may be a barley plant carrying a mutation in the CslF6 gene and encoding a mutant CslF6 polypeptide, wherein the CslF6 polypeptide is a CslF6 polypeptide of SEQ ID NO:1 or SEQ ID NO:3 except that mutant CslF6 comprises a substitution of amino acid 709, wherein said substitution is substitution of a threonine (T) for an isoleucine (I), and the kernels of said barley plant may have a (1,3;1,4)-β-glucan content in the range of 1.0 to 3.0 dry weight of total kernels, for example a (1,3;1,4)-β-glucan content in the range of 1.0 to 3.0% dry weight of total kernels, such as a (1,3;1,4)-β-glucan content in the range of 1.0 to 2.5% dry weight of total kernels, preferably a (1,3;1,4)-β-glucan content in the range of 1.0 to 2.0% dry weight of total kernels, such as a (1,3;1,4)-β-glucan content in the range of 1.0 to 1.7 dry weight of total kernels, for example a (1,3;1,4)-β-glucan content in the range of 1.2 to 3.0% dry weight of total kernels, such as a (1,3;1,4)-β-glucan content in the range of 1.5 to 3.0% dry weight of total kernels, preferably a (1,3;1,4)-β-glucan content in the range of 1.3 to 3.0% dry weight of total kernels.

In one embodiment the barley plant may have a (1,3;1,4)-β-glucan content in the kernels, which is reduced to at the most 70%, preferably at the most 60%, such as at the most 55% of the (1,3;1,4)-β-glucan content in the kernels of a barley comprising a wild type CslF6 gene, but otherwise of the same genotype.

The barley plant, may be a barley plant having a (1,3;1,4)-β-glucan content in the kernels reduced to at least 30% and at most 60%, preferably at least 40% and at most 60%, for example at least 40% and at most 55% of the (1,3;1,4)-β-glucan content in the kernels of a barley comprising a wild type CslF6 gene, but otherwise of the same genotype.

In one embodiment, the barley plant, may be a barley plant having a (1,3;1,4)-β-glucan content in the kernels reduced to at least 30% and at most 60%, preferably at least 40% and at most 60%, for example at least 40% and at most 55% of the (1,3;1,4)-β-glucan content in the kernels of a barley plant of cv. Paustian.

In one embodiment, the barley plant may be a barley plant carrying a mutation in the CslF6 gene and encoding a mutant CslF6 polypeptide, wherein the CslF6 polypeptide is a CslF6 polypeptide of SEQ ID NO:1 or SEQ ID NO:3 except that mutant CslF6 comprises a substitution of amino acid 847, wherein said substitution is substitution of a glycine (G) to a glutamic acid (E), and the kernels of said barley plant may have a (1,3;1,4)-β-glucan content reduced to at least 30% and at most 60%, such as at least 40% and at most 60% of the (1,3;1,4)-β-glucan content in the kernels of a barley comprising a wild type CslF6 gene, but otherwise of the same genotype.

In one embodiment, the barley plant may be a barley plant carrying a mutation in the CslF6 gene and encoding a mutant CslF6 polypeptide, wherein the CslF6 polypeptide is a CslF6 polypeptide of SEQ ID NO:1 OR SEQ ID NO:3 except that mutant CslF6 comprises a substitution of amino acid 748, wherein said substitution is substitution of a glycine (G) for an aspartic acid (D), and the kernels of said barley plant may have a (1,3;1,4)-β-glucan content reduced to at least 30% and at most 60%, such as at least 40% and at most 60% of the (1,3;1,4)-β-glucan content in the kernels of a barley comprising a wild type CslF6 gene, but otherwise of the same genotype.

In one embodiment, the barley plant may be a barley plant carrying a mutation in the CslF6 gene and encoding a mutant CslF6 polypeptide, wherein the CslF6 polypeptide is a CslF6 polypeptide of SEQ ID NO:1 OR SEQ ID NO:3 except that mutant CslF6 comprises a substitution of amino acid 709, wherein said substitution is substitution of a threonine (T) to an isoleucine (I), and the kernels of said barley plant may have a (1,3;1,4)-β-glucan content reduced to at least 30% and at most 60%, such as at least 40% and at most 60% of the (1,3;1,4)-β-glucan content in the kernels of a barley comprising a wild type CslF6 gene, but otherwise of the same genotype.

The barley plants of the invention carrying a mutation in the CslF6 gene and encoding a mutated CslF6 polypeptide, and having kernels with a reduced (1,3;1,4)-β-glucan content may further be characterized by kernels with a given DP3:DP4 ratio, such as a DP3:DP4 ratio lower than the DP3:DP4 ratio of a wild type plant or higher than the DP3:DP4 ratio of a wild type plant or similar to the DP3:DP4 ratio of a wild type plant.

Dependent on various factors different DP3:DP4 may be desirable.

Wild type barley plants are usually characterized by a DP3:DP4 ratio in the range of 2.5 to 4.

In one embodiment, the barley plants of the invention comprise (1,3;1,4)-β-glucan in the kernels having a DP3:DP4 ratio of at the most 2.5, such as at the most 2.2, for example in the range of 1.0 to 2.2.

In one embodiment, the barley plant may be a barley plant carrying a mutation in the CslF6 gene and encoding a mutant CslF6 polypeptide, wherein the CslF6 polypeptide is a CslF6 polypeptide of SEQ ID NO:1 OR SEQ ID NO:3 except that mutant CslF6 comprises a substitution of amino acid 847, wherein said substitution is substitution of a glycine (G) to a glutamic acid (E), and the kernels of said barley plant may have a DP3:DP4 ratio of at the most 2.5, such as at the most 2.2, for example in the range of 1.0 to 2.2.

In one embodiment, the kernels of said barley plant may have a DP3:DP4 ratio in the range of 2.5 to 4.

In one embodiment, the barley plant may be a barley plant carrying a mutation in the CslF6 gene and encoding a mutant CslF6 polypeptide, wherein the CslF6 polypeptide is a CslF6 polypeptide of SEQ ID NO:1 OR SEQ ID NO:3 except that mutant CslF6 comprises a substitution of amino acid 748, wherein said substitution is substitution of a Glycine (G) to an aspartic acid (D), and the kernels of said barley plant may have a DP3:DP4 ratio in the range of 2.5 to 4.

In one embodiment, the kernels of said barley plant may have a DP3:DP4 ratio of at least 3.5, such as of at least 4.0, for example at least 4.5, such as in the range of 4 to 6.

In one embodiment, the barley plant may be a barley plant carrying a mutation in the CslF6 gene and encoding a mutant CslF6 polypeptide, wherein the CslF6 polypeptide is a CslF6 polypeptide of SEQ ID NO:1 OR SEQ ID NO:3 except that mutant CslF6 comprises a substitution of amino acid 709, wherein said substitution is substitution of a threonine (T) to an isoleucine (I), and the kernels of said barley plant may have a DP3:DP4 ratio of at least 3.5, such as of at least 4.0, for example at least 4.5, such as in the range of 4 to 6.

(1,3;1,4)-β-glucan is a cell wall component and reduction in (1,3;1,4)-β-glucan level may influence barley plants. For example, reductions in (1,3;1,4)-β-glucan level and/or changes in the DP3/DP4 ratio of (1,3;1,4)-β-glucans may result in fragile barley grains having a high percentage of broken grains.

In one embodiment it is preferred that the barley plants of the invention have kernels of an acceptable grain hardness. Thus, in one embodiment the barley plants may have kernels with a frequency of broken grain of less than 5%, such as less than 3% when determined as described in Example 6 herein below.

In particular it is preferred that the frequency of broken grains after threshing of grains of the barley plants of the invention is at the most 3 times higher, more preferably at the most 2 times higher than the frequency of a broken grains after threshing of grains of a barley plant not carrying a mutation in the CslF6 gene, but otherwise identical. For example, barley plants carrying a mutation in the CslF6 gene encoding a mutant HvCslF6 protein comprising a mutation (e.g. a Gly→Asp) of amino acid 748 of SEQ ID NO:1 or SEQ ID NO:3 have a frequency of broken grains after threshing of grains, which is at the most 3 times higher, more preferably at the most 2 times higher than the frequency of a broken grains after threshing of grains of a barley plant not carrying said mutation, but otherwise identical. The frequency of broken grains is preferably determined as described in Example 6 herein below.

Barley Plants Comprising More than One Mutation

In addition to the mutations described herein the barley plants may also comprise one or more further mutations. Accordingly, the barley plant may comprise one or more of following mutations.

In addition to one or more of the mutations described above, the barley plant may also comprise a mutation in the gene encoding LOX-1 resulting in a total loss of functional LOX-1. Said mutation may for example be any of the mutations described in international patent application WO 2005/087934. For example the barley plant may comprise a gene encoding LOX-1 comprising a premature stop codon, said codon corresponding to base nos. 3572-3574 of SEQ ID NO:2 of WO 2005/087934 or a splice site mutation, said mutation corresponding to base no. 2311 of SEQ ID NO: 6 of SEQ ID NO:2 of WO 2005/087934.

In addition to one or more of the mutations described above, the barley plant may also comprise a mutation in the gene encoding LOX-2 resulting in a total loss of functional LOX-2. Said mutation may for example be any of the mutations described in international patent application WO 2010/075860. For example the barley plant may comprise a gene encoding LOX-2 comprising a mutation at nucleotide position 2689 of SEQ ID NO:1 of WO 2010/075860, leading to formation of a premature stop codon.

In addition to one or more of the mutations described above, the barley plant may also comprise a mutation in the gene encoding MMT resulting in a total loss of functional MMT. Said mutation may for example be any of the mutations described in international patent application WO 2010/063288. For example the barley plant may comprise a gene encoding MMT comprising a G→A mutation of base no. 3076 of SEQ ID NO:3 of WO 2010/063288 or a gene encoding MMT comprising a G→A mutation of base no. 1462 of SEQ ID NO:16 WO 2010/063288.

In addition to one or more of the mutations described above, the barley plant may also comprise any of the mutations leading to increased alpha-amylase activity described in co-pending application entitled "Barley with increased hydrolytic enzyme activity" assigned to the same applicant and with the same filing date as the present application.

Plant Products

The invention also provides plant products prepared from a barley plant having a reduced (1,3;1,4)-β-glucan content and carrying a mutation in the CslF6 gene, or a progeny thereof, wherein said mutated CslF6 gene encodes a mutant CslF6 polypeptide, e.g. any of the barley plants described herein.

The plant product may be any product prepared from a barley plant, for example a food, a feed or a beverage. Thus the plant product may be any of the beverages described herein below in the section "Beverage and method of production thereof". The plant product may also be an aqueous extract of the barley plant and/or malt prepared from kernels of said barley plant, for example the plant product may be wort. Said aqueous extract may for example be prepared as described herein below in the section "Aqueous extract and methods of production thereof".

In one embodiment the plant product may be malt, e.g. a green malt or a kiln dried malt, such as any of the malts described herein below in the section "Green malt, kiln dried malt and methods of production thereof" or a malt based product, such as malt based beverages. Although the primary use of malt is for beverage production, it can also be utilized in other industrial processes, for example as an enzyme source in the baking industry, or in the food industry as a flavouring and colouring agent, e.g. in the form of malt or malt flour or indirectly as a malt syrup, etc. Thus, the plant product according to the invention may be any of the aforementioned products.

In one embodiment of the invention, the plant product is barley flour, i.e. barley flour prepared from grains of a barley plant according to the invention.

In another aspect, the plant products according to the invention comprise, or even consist of syrup, such as a barley syrup, or a barley malt syrup. The plant product may also be an extract of barley or malt. Thus, the plant product may be wort.

Green Malt, Kiln Dried Malt and Methods of Production Thereof

The invention also provides malt prepared from a barley plant carrying a mutation in the CslF6 gene, for example any of the barley plants described herein. Said malt may be green malt or kiln dried malt prepared from barley grains from a barley plant carrying a mutation in the CslF6 gene, or progeny thereof. Said mutation may be any of the mutations in the CslF6 gene described herein above.

Green malt may be prepared by malting, i.e. by germination of cereal grains under controlled environmental conditions. Typically, said germination may comprise a step of steeping barley kernels followed by a step of germination. Steeping and germination may also be performed simultaneously or partly simultaneously. In some embodiments, the production of malt may comprise a step of drying the germinated grains. Said drying step may preferably be kiln drying of the germinated kernels at elevated temperatures. Thus, kiln dried malt may be prepared by subjecting green malt to a step of kiln drying.

Thus, in one embodiment a method of malting may comprise the steps of:
(a) providing kernels of a barley plant, notably a barley plant, carrying a mutation in the CslF6 gene;
(b) steeping said barley kernels;
(b) germinating said barley kernel; and
(c) drying said germinated barley kernels, preferably by kiln drying.

Germinated barley grains may be prepared by a method comprising the steps of
(a) providing kernels of a barley plant, notably a barley plant, carrying a mutation in the CslF6 gene;
(b) steeping said barley kernels;
(b) germinating said barley kernel.

The steps of steeping and germinating may be performed at sequentially, simultaneously or partly simultaneously.

In one preferred embodiment steeping and germination is performed simultaneously in a germination process, which comprises incubating barley grains in an aqueous solution typically under aeration for at the most 72 h.

Steeping may be performed by any conventional method known to the skilled person. One non-limiting example involves steeping at a temperature in the range of 10 to 25° C. with alternating dry and wet conditions. During steeping, for example, the barley kernels may be incubated wet for in the range of 30 min to 3 h followed by incubation dry for in the range of 30 min to 3 h and optionally repeating said incubation scheme in the range of 2 to 5 times. The final water content after steeping may, for example, be in the range of 40 to 50%, for example in the range of 40-45%.

The barley plants provided by the invention are characterized by carrying a mutation in the CslF6 gene and so encoding a mutated CslF6 polypeptide. One major advantage of such barley plants is that the kernels have a reduced (1,3;1,4)-β-glucan content and an adequate DP3:DP4 ratio. Grains of these barley plants with reduced (1,3;1,4)-β-glucan content may be advantageously germinated in a short germination process. Examples of useful short germination processes are described in international patent application PCT/EP2017/065498, which is incorporated by reference herein. One example of a useful short germination process is a germination process comprising a step where the barley grains are incubated in an aqueous solution typically under aeration, wherein the entire germination process is performed for at the most 72 h. In fact, during germination (1,3;1,4)-β-glucans are usually at least partly hydrolysed by enzymes, such as β-glucanase. The hydrolytic enzymes specific for (1,3;1,4)-β-glucans are usually present in a minor amount at the beginning of the germination process. The presence of the hydrolytic enzymes specific for (1,3;1,4)-β-glucans increases as the germination process continues. A germination process performed for at the most 72 h in general does not provide for sufficient time for hydrolysing the (1,3;1,4)-β-glucans to the desired low level, if the (1,3;1,4)-β-glucan content is high from the onset. However, the barley plants of the invention already have a low level of (1,3;1,4)-β-glucans from the onset, and thus the hydrolysis of (1,3;1,4)-β-glucans during germination is less critical.

As described above the germination may comprise a step of incubating grains of a barley plant carrying a mutation in the CslF6 gene in an aqueous solution under aeration. The barley grains may be incubated in said aqueous solution for sufficient time to allow germination of the majority of said barley grains. The barley grains may also be incubated in said aqueous solution for sufficient time in order to obtain a water content of at least 35%, preferably of at least 37%, for example in the range of 35 to 60%. Typically, the barley grains are incubated in the aqueous solution for at least 20 h, such as at least 24 h. Typically, the grains are incubated in said aqueous solution for at the most 72 h, such as for at the most 60 h, for example for at the most 48 h. Thus, in some embodiments the barley grains are incubated in said aqueous solution for in the range of 20 to 72 h, such as for in the range of 20 to 60 h, for example for in the range of 20 to 48 h, for example for in the range of 20 to 30 h, such as for in the range of 22 to 26 h.

It may be preferred that the barley grains are completely covered by said aqueous solution during the entire incubation.

Said barley grains are frequently incubated in said aqueous solution, while $O_2$ is passed through the aqueous solution. Said $O_2$ may be added to said aqueous solution as pure $O_2$. Frequently, however, said $O_2$ is comprised within a gas mixture. In one embodiment said $O_2$ is comprised within atmospheric air.

In general, at least 2 L, preferably at least 3 L, more preferably at least 4 L, yet more preferably at least 5 L, even more preferably at least 6 L $O_2$ passes through said aqueous solution per kg barley grains per h. The weight of said barley grains is the dry weight. For example, in the range of 2 to 100 L, for example in the range of 2 to 75 L, such as in the range of 2 to 50 L, for example in the range of 4 to 100 L, for example in the range of 4 to 75 L, such as in the range of 4 to 50 L, for example in the range of 6 to 100 L, for example in the range of 6 to 75 L, such as in the range of 6 to 50 L $O_2$ passes through said aqueous solution/barley grain mixture per kg barley grains (dry weight) per h.

As noted above, it is frequently atmospheric air that is passed through the aqueous solution. Thus, the method may comprise passing at least 10 L, preferably at least 15 L, more preferably at least 20 L, yet more preferably at least 25 L, even more preferably at least 30 L atmospheric air through said aqueous solution per kg barley grains per h. The weight of said barley grains is the dry weight. For example, in the range of 10 to 500 L, for example in the range of 10 to 375 L, such as in the range of 10 to 250 L, for example in the range of 20 to 500 L, for example in the range of 20 to 375 L, such as in the range of 20 to 250 L, for example in the range of 30 to 500 L, for example in the range of 30 to 375 L, such as in the range of 30 to 250 L atmospheric air is passed through said aqueous solution per kg barley grains (dry weight) per h.

In some embodiments the step of germination comprises
a. at least one step of incubating said kernels in an aqueous solution, wherein at least 2 L $O_2$ per kg dry weight barley kernels is passed through said aqueous solution per h; and
b. at least one step of incubating said barley kernels in air.

In some embodiments, after incubation of the barley grains in said aqueous solution, then the barley grains have a water content of at least 20%, preferably of at least 30%, for example in the range of 30 to 60%, such as in the range of 30 to 50%, for example in the range of 30 to 60%, such as in the range of 30 to 50%.

During said step of incubating said barley kernels in air, at least 2 L $O_2$ per kg dry weight barley kernels may be passed through said barley kernels per h. For example, the same amount of $O_2$ may be lead through the barley kernels during incubation in air as during incubation in said aqueous solution as described above.

The germinated barley kernels prepared by this method are also referred to as green malt herein.

The water content of barley grains may be determined by determining the weight of the barley grains, followed by drying said barley grains and determining the weight of the dried barley grains. The difference in weight of the wet and dry barley grains is considered to be water, and the water content is provided as the weight of the water divided by the total weight of the barley grains (wet barley grains). The water content provided in % is thus a w/w %.

The barley grain may be incubated at any useful temperature, however it may be preferred that incubation is performed at a temperature sufficiently high to allow fast increase in water content.

In particular, in embodiments of the invention wherein the barley grains are incubated at a temperature in the range of 20 to 30° C., then said barley grains may be incubated for in the range of 20 to 48 h.

Germination of grains may also be performed by any conventional method known to the skilled person. One non-limiting example involves germination at a temperature in the range of 10 to 25° C., optionally with changing temperature in the range of 1 to 4 days.

As mentioned above in some embodiments of the invention, the germinated barley grains (i.e. the green malt) may be kiln dried. In some embodiments it is preferred that the green malt is not kiln dried. In particular, it is preferred, that when green malt is prepared by a germination comprising a step of incubating said barley grains in an aqueous solution under aeration, then the green malt is not kiln dried.

If the green malt is kiln dried, this may be done at conventional temperatures, such as at least 75° C., for example in the range of 80 to 90° C., such as in the range of 80 to 85° C. Thus, the malt may, for example be produced by any of the methods described by Hough et al. (1982). However, any other suitable method for producing malt may also be used with the present invention, such as methods for production of specialty malts, including, but not limited to, methods of roasting the malt.

Kiln dried malt and green malt may be further processed, for example by milling. Thus, the plant product according to the invention may be any kind of malt, such as unprocessed malt or milled malt, such as flour. Thus, the plant product may for example be milled, kiln dried malt or milled green malt. Milled malt and flour thereof comprise chemical components of the malt and dead cells that lack the capacity to re-germinate.

In some embodiments the barley is hulled barley, and the method comprises a step of removing at least part of said hull prior to incubating said kernels in an aqueous solution. Hulled cereal grains may be treated to remove hull by subjecting the cereal grains to physical treatment removing hull. Said physical treatment may for example be selected from the group consisting of polishing, sanding, peeling and smoothening. Preferably, the physical treatment results in a loss of the hull. Loss of the hull may be determined as an overall weight loss. Thus, the physical treatment preferably leads to a loss of in the range of 1 to 4%, such as in a loss of in the range of 1.5 to 3.0% of the total weight of the cereal grains.

Aqueous Extract and Methods of Production Thereof

The invention provides barley based beverages as well as methods of preparing the same, wherein the barley plant carries a mutation in the CslF6 gene, or progeny thereof. The invention also provides aqueous extracts of kernels of barley plants carrying a mutation in the CslF6 gene. Said aqueous extract may for example be prepared from green malt or kiln dried malt.

Frequently, methods for preparing a beverage comprise a step of preparing an aqueous extract of kernels of the barley plants of the invention and/or of malts prepared from barley plants of the invention.

The aqueous extract may, in general, be prepared by incubating barley flour, flour of green malt and/or flour of kiln dried malt in water or in an aqueous solution. Said aqueous solution is also referred to as "mashing solution" herein. In particular, the aqueous extract may be prepared by mashing.

The present invention also provides a method of producing an aqueous extract, said method comprising the steps of:
a. providing kernels of a barley plant, wherein said barley plant have reduced (1,3;1,4)-β-glucan content and carries a mutation in the CslF6 gene, as described herein;
b. subjecting the barley kernels to a step of germination thereby obtaining germinated kernels, wherein said step of germination comprises incubating said kernels in an aqueous solution at the most 72 h;
c. finely dividing said germinated kernels, while said germinated kernels have a water content of at least 20%, with the proviso that said barley kernels do not have a water content below 20 at any time between steps b) and c);
d. preparing an aqueous extract of said milled germinated kernels, thereby producing an aqueous extract of the barley.

The germination step is described in detail in the section above "Green malt, kiln dried malt and method of production thereof".

In general said mashing solution may be water, such as tap water to which one or more additional agents may be added. The additional agents may be present in the aqueous solution from the onset or they may be added during the process of preparing an aqueous extract. Said additional agents may be enzymes. Thus, the mashing solution may comprise one or more enzymes. Said enzymes may be added to the aqueous solution from the onset, or subsequently, during the process.

Said enzymes may, for example, be one or more hydrolytic enzymes. Suitable enzymes include lipases, starch degrading enzymes (e.g. amylases), glucanases [preferably (1-4)- and/or (1,3;1,4)-β-glucanases], and/or xylanases (such as arabinoxylanases), and/or proteases, or enzyme mixtures comprising one or more of the aforementioned enzymes, e.g. Cereflo, Ultraflo, or Ondea Pro (Novozymes). For example, the aqueous solution may comprise one or more hydrolytic enzymes selected from the group consisting of α-amylase, β-amylase, limit dextrinase, pullulanase, β-glucanase (e.g. endo-(1,3;1,4)-β-glucanase or endo-1,4-β-glucanase), xylanase (e.g. endo- or exo-1,4-xylanase, an arabinofuranosidase or a ferulic acid esterase), glucoamylase and protease.

In one embodiment no or only limited amounts of β-glucanase is added to said mashing solution.

Said additional agents, preferably of food grade quality, may also be a salt, for example $CaCl_2$, or an acid, for example $H_3PO_4$.

The aqueous extract is generally prepared by incubation of the barley flour, flour of green malt and/or flour of kiln dried malt in the mashing solution at one or more predetermined temperature(s). Said predetermined temperature may also be referred to as "mashing temperature" herein. Said mashing temperatures may for example be conventional temperatures used for mashing. The mashing temperature is in general either kept constant (isothermal mashing), or gradually increased, for example increased in a sequential manner. In either case, soluble substances in the barley grains and/or malt are liberated into said mashing solution thereby forming an aqueous extract.

The mashing temperature(s) are typically temperature(s) in the range of 30 to 90° C., such as in the range of 40 to 85° C., for example in the range of 50 to 85° C. The mashing temperatures may be chosen according to the barley type used. In particular, a relatively low mashing-in temperature may be used, e.g. a temperature in the range of 50 to 60° C. Frequently, incubation with the mashing solution includes a final step of heating to a higher temperature, e.g. to a temperature in the range of 75 to 80° C.

Subsequent to incubation in the aqueous solution in e.g. a mashing vessel, the aqueous solution may be transferred to another container, e.g. a lauter tun and incubated for additional time at elevated temperature.

Non-limiting examples of useful mashing protocols can be found in the literature of brewing, e.g. in Hough et al. (supra).

Mashing (i.e. incubation of the barley flour, flour of green malt and/or flour of kiln dried malt in mashing solution) can occur in the presence of adjuncts, which is understood to comprise any carbohydrate source other than malt or germinated barley grains, such as, but not limited to, barley, barley syrups, or maize, or rice—either as whole kernels or processed products like grits, syrups or starch. All of the aforementioned adjuncts may be used principally as an additional source of extract (syrups are typically dosed during wort heating). The requirements for processing of the adjunct in the brewery depend on the state and type of adjunct used.

After incubation in the mashing solution, the aqueous extract may typically be separated, e.g. through filtration into the aqueous extract and residual non-dissolved solid particles, the latter also denoted "spent grain". Filtering may for example be performed in a lauter tun. Alternatively, the filtering may be filtering through a mash filter. The aqueous extract thus obtained may also be denoted "first wort". Additional liquid, such as water may be added to the spent grains during a process also denoted sparging. After sparging and filtration, a "second wort" may be obtained. Further worts may be prepared by repeating the procedure. Thus, the aqueous extract may be wort, e.g. a first wort, a second wort, a further wort or a combination thereof.

Figure 4:
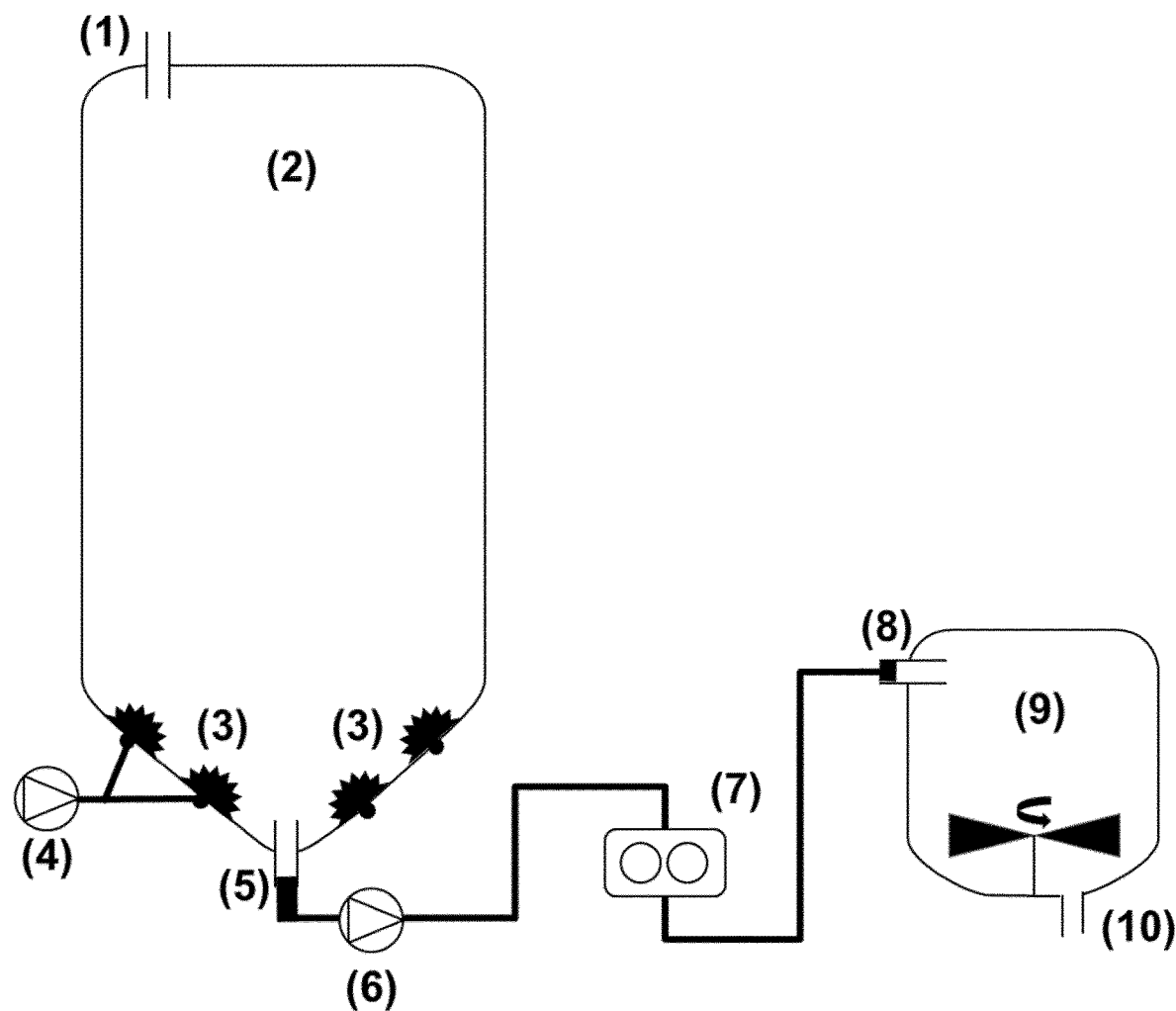
FIG. 4 shows an example of equipment useful for preparing green malt. The equipment comprises a tank (2) in which grains can be immersed in an aqueous solution and aerated continuously. The equipment comprises an inlet for cereal grains (1), a tank, e.g. a steeping tank (2); inlets for gas, e.g. sinter stones (3); a pump e.g. an air pump (4); an outlet for cereal grains (5); a grain pump (6); an equipment for finely dividing cereal grains e.g. a mill (7); an inlet (8); a vessel, e.g. a mashing vessel (9), and; an outlet (10).

The method of preparing an aqueous extract may in one embodiment be performed using any of the apparatuses described in international patent application PCT/EP2017/065498, for example any of the apparatuses described on p. 20-22 therein. A non-limiting example of a useful apparatus is provided herein in FIG. 4.

Incompletely degraded (1,3;1,4)-β-glucans can be especially troublesome for brewers, because these can be extracted from the malt in soluble forms that form highly viscous aqueous solutions that slow filtration processes in the brewery. Interestingly, the barley plants of the invention contain a low level of (1,3;1,4)-β-glucans and thus, wort prepared from such barley plants in general has low viscosity. In one embodiment, the invention provides wort prepared from a barley plant carrying a mutation in the CslF6 gene, said wort having a lower viscosity compared to wort prepared from a barley plant carrying a wild type CslF6 gene, but otherwise of the same genotype of the barley plant disclosed herein. Said wort is in general prepared by extraction of barley grains and/or malt.

In one embodiment, the invention provides a wort, wherein said wort is prepared from a barley plant carrying any of the mutations in the CslF6 gene described herein, wherein said wort has a viscosity in the range of 0.5 to 1.0 mPa*s lower, such as in the range of 0.5 to 0.8 mPa*s lower than the viscosity of wort prepared in the same manner from a barley plant carrying a wild type CslF6 gene, but otherwise of the same genotype. In one embodiment, the invention provides a wort, wherein said wort is prepared from a barley plant carrying any of the mutations in the CslF6 gene described herein and said wort has a viscosity in the range of 1.7 to 2.5 mPa*s, such as in the range of 1.8 to 2.5 mPa*s, for example of 2.0 to 2.5 mPa*s, such as of 2.1 to 2.5 mPa*s, for example 1.8 to 2.2 mPa*s, such as of about 2 mPa*s, for example of about 2.1 mPa*s, such as of about 2.2 mPa*s. In particular, the barley plant may carry a mutated HvCslF6 gene encoding a mutant HvCslF6 protein comprising a mutation (e.g. a Gly→Asp) of amino acid 748 of SEQ ID NO:1.

In one embodiment, the invention provides a wort, wherein said wort is prepared from malt obtained from a barley plant carrying any of the mutations in the CslF6 gene described herein, wherein said wort has a viscosity of at the most 2.2 mPa*s.

The viscosity of a wort prepared from standard malt prepared by steeping for 1-2 days and germination for 5-7 days followed by kiln drying is of about 2 mPa*s.

Beverage and Method of Production Thereof

The present invention also provides barley based beverages and methods of producing such beverages, wherein the barley plant has reduced (1,3;1,4)-β-glucan content and carries a mutation in the CslF6 gene, or progeny thereof. The invention also provides barley based beverages, prepared from barley plants carrying a mutation in the CslF6 gene, or progeny thereof.

Said beverage may be an alcoholic barley based beverages or non-alcoholic barley based beverages. Alcoholic barley based beverages may for example be beer or a distilled alcohol.

Said beer may be any kind of beer, for example lager or ale. Thus, the beer may for example be selected from the group consisting of altbier, Amber ale, Barley wine, Berliner Weisse, Bière de Garde, Bitter, Blonde Ale, Bock, Brown ale, California Common, Cream Ale, Dortmunder Export, Doppelbock, Dunkel, Dunkelweizen, Eisbock, Fruit lambic, Golden Ale, Gose, Gueuze, Hefeweizen, Helles, India pale ale, Kölsch, Lambic, Light ale, Maibock, Malt liquor, Mild, Marzenbier, Old ale, Oud bruin, Pale ale, Pilsener, Porter, Red ale, Roggenbier, Saison, Scotch ale, Steam beer, Stout, Schwarzbier, lager, Witbier, Weissbier and Weizenbock.

Said distilled alcohol may be any kind of distilled alcohol. In particular the distilled alcohol may be based on a barley, e.g. a barley malt. Non-limiting examples of such distilled alcohol include whiskey and vodka.

The beverage may be a non-alcoholic beverage, such as a non-alcoholic barley based beverage, e.g. non-alcoholic beer or non-alcoholic malt beverages, such as maltina.

The beverage may for example be prepared by a method comprising the steps of:
(i) Providing kernels of a barley plant according to the invention and/or green malt and/or kiln dried malt prepared from kernels of a barley plant according to the invention
(ii) Preparing an aqueous extract of said kernels and/or said malt, e.g. as described herein above in the section preparing aqueous extract
(iii) processing said aqueous extract into a beverage.

The aqueous extract may be boiled with or without hops where after it may be referred to as boiled wort. First, second and further worts may be combined, and thereafter subjected to boiling. The aqueous extract may be boiled for any suitable amount of time, e.g. in the range of 60 min to 120 min.

Step (iii) may comprise
a. heating said aqueous extract optionally in the presence of hops or hops extract;
b. cooling the aqueous extract;
c. fermenting said aqueous extract with yeast, thereby producing a fermented beverage.

Step (iii) may in particular comprise fermentation of said aqueous extract, e.g. by fermentation of wort. Thus, the beverage may be prepared by fermentation of the aqueous extract with yeast.

Once the aqueous extract has been prepared it may be processed into beer by any method including conventional brewing methods. Non-limited descriptions of examples of suitable methods for brewing can be found, for example, in publications by Hough et al. (1982). Numerous, regularly updated methods for analyses of barley and beer products are available, for example, but not limited to, American Association of Cereal Chemists (1995), American Society of Brewing Chemists (1992), European Brewery Convention (1998), and Institute of Brewing (1997). It is recognized that many specific procedures are employed for a given brewery, with the most significant variations relating to local consumer preferences. Any such method of producing beer may be used with the present invention.

The first step of producing beer from the aqueous extract preferably involves boiling said aqueous extract as described herein above, followed by a subsequent phase of cooling and optionally whirlpool rest. One or more additional compounds may be added to the aqueous extract, e.g. one or more of the additional compounds described below in the section "Additional compounds". After being cooled, the aqueous extract may be transferred to fermentation tanks containing yeast, e.g. brewing yeast, such as *S. pastorianus* or *S. cerevisiae*. The aqueous extract may be fermented for any suitable time period, in general in the range of 1 to 20 days, such as 1 to 10 days. The fermentation is performed at any useful temperature e.g. at a temperature in the range of 10 to 20° C. The methods may also comprise addition of one or more enzymes, e.g. one or more enzymes may be added to the wort prior to or during fermentation. In particular, said enzyme may be a proline-specific endoprotease. A non-limiting examples of a proline-specific endoprotease is "Brewer's Clarex" available from DSM. In other embodiments, no exogenous enzymes are added during the methods.

During the several-day-long fermentation process, sugar is converted to alcohol and $CO_2$ concomitantly with the development of some flavour substances. The fermentation may be terminated at any desirable time, e.g. once no further drop in % P is observed.

Subsequently, the beer may be further processed, for example chilled. It may also be filtered and/or lagered—a process that develops a pleasant aroma and a less yeast-like flavour. Additives may also be added. Furthermore, $CO_2$ may be added. Finally, the beer may be pasteurized and/or filtered, before it is packaged (e.g. transferred to containers or kegs, bottled or canned). The beer may also be pasteurized by standard methods.

Additional Compounds

The methods of the invention may comprise the step of adding one or more additional compounds. Said additional compounds may for example be a flavor compound, a preservative, a functional ingredient, a color, a sweetener, a pH regulating agent or a salt. The pH regulating agent may for example be a buffer or an acid, such as phosphoric acid.

Functional ingredients may be any ingredient added to obtain a given function. Preferably a functional ingredient renders the beverage healthier. Non-limiting examples of functional ingredients includes vitamins or minerals.

The preservative may be any food grade preservative, for example it may be benzoic acid, sorbic acid, sorbates (e.g. potassium sorbate), sulphites and/or salts thereof.

The additional compound may also be $CO_2$. In particular, $CO_2$ may be added to obtain a carbonated beverage.

The flavour compound to be used with the present invention may be any useful flavour compound. The flavour compound may for example be selected from the group consisting of aromas, plant extracts, plant concentrates, plant parts and herbal infusions. In particular the flavor compounds may be hops.

Method of Preparing a Barley Plant Carrying a Mutation in CslF6

Barley plants carrying a mutation in CslF6, e.g. any of the specific mutations described herein may be prepared in any useful manner.

For example, such barley plants can be prepared by a method comprising the steps of:
  subjecting a plurality of barley plants or barley kernels to random mutagenesis, e.g. by irradiation or chemical treatment, e.g. treatment with sodium azide;
  identifying barley plants or barley kernels carrying a mutation in CslF6.

Such methods may also include one or more steps of reproducing said barley plants/barley kernels in order to obtain multiple barley plants/kernels each carrying random mutations.

In particular, barley plants carrying a particular mutation in CslF6 may be prepared and identified essentially as described in international patent application PCT/EP2017/065516 using primers and probes designed to identify a mutation in the CslF6 gene. Examples of primers and probes useful for identication of a barley plant carrying a mutation in the CslF6 gene resulting in said gene encoding mutant CslF6 protein carrying one of the mutations G847E or G748D are provided in Table 2. The skilled persons will based on common general knowledge and/or the guidance provided in international patent application PCT/EP2017/065516, which is incorporated herein by reference be able to design useful primers and probes for identification of other mutants.

Barley plants carrying a mutation in the CslF6 gene may also be prepared using various site directed mutatgenesis methods, which for example can be designed based on the sequence of the CslF6 gene provided herein. In one embodiment, the barley plant is prepared using any one of CRISPR, a TALEN, a zinc finger, meganuclease, and a DNA-cutting antibiotic as described in WO 2017/138986. In one embodiment, the barley plant is prepared using CRISPR/cas9 technique, e.g. using RNA-guided Cas9 nuclease. This may be done as described in Lawrenson et al., Genome Biology (2015) 16:258; DOI 10.1186/s13059-015-0826-7 except that the single guide RNA sequence is designed based on the genes sequences provided herein. In one embodiment, the barley plant is prepared using a combination of both TALEN and CRISPR/cas9 techniques, e.g. using RNA-guided Cas9 nuclease. This may be done as described in Holme et al., Plant Mol Biol (2017) 95:111-121; DOI: 10.1007/s11103-017-0640-6 except that the TALEN and single guide RNA sequence are designed based on the genes sequences provided herein.

In one embodiment, the cereal plant is prepared using homology directed repair, a combination of a DNA cutting nuclease and a donor DNA fragment. This may be done as described in Sun et al., Molecular Plant (2016) 9:628-631; DOI: 10.1016/j.molp.2016.01.001 except that the DNA cutting nuclease is designed based on the genes sequences provided herein and the donor DNA fragment is designed based on the coding sequence of the mutated cereal variant provided herein.

In one embodiment of the invention, the objective is to provide agronomical useful barley plants carrying a mutation in the CslF6 gene. In addition to the mutation in the CslF6 gene, there are additional factors which also may be considered in the art of generating a commercial barley variety useful for malting and/or brewing and/or as base for beverages, for example kernel yield and size, and other parameters that relate to malting performance or brewing performance. Since many—if not all—relevant traits have been shown to be under genetic control, the present invention also provides modern, homozygous, high-yielding malting cultivars, which may be prepared from crosses with the barley plants that are disclosed in the present publication. The skilled barley breeder will be able to select and develop barley plants, which—following crossings with other barley plants—will result in superior cultivars. Alternatively, the breeder may utilize plants of the present invention for further mutagenesis to generate new cultivars carrying additional mutations in addition to the mutation of the CslF6 gene.

The invention also comprise barley plants carrying a mutation in the CslF6 gene prepared from plant breeding method, including methods of selfing, backcrossing, crossing to populations, and the like. Backcrossing methods can be used with the present invention to introduce into another cultivar the mutation of the CslF6 gene.

In one embodiment, the invention relates to progeny of the barley plant deposited on 12-11-2018 with NCIMB under the accession number NCIMB 43273 and referred to as "Mutant 2". Said progeny may be prepared by any useful method, including but not limited to selfing, backcrossing, or crossing to other populations. In particular, said progeny may also carry a G→A mutation of nucleotide 2243 of the coding sequence of the HvCslF6 gene (SEQ ID NO 2).

A way to accelerate the process of plant breeding comprises the initial multiplication of generated mutants by application of tissue culture and regeneration techniques. Thus, another aspect of the present invention is to provide cells, which upon growth and differentiation produce barley plants carrying the mutation of the CslF6 gene. For example, breeding may involve traditional crossings, preparing fertile anther-derived plants or using microspore culture.

In one embodiment the barley plant of the invention has not exclusively been obtained by means of an essentially biological process. Progeny of a barley plant obtained by a technical process is herein considered as not being exclusively obtained by means of an essentially biological process, because the parent plant is obtained by a technical process.

In one embodiment the barley plant carries a mutation in the CslF6 gene, wherein said mutation has been induced by chemical and/or physical agents.

In one embodiment the barley plant has been prepared by a method involving a step of induced mutagenesis or said plant is progeny of a plant prepared by a method involving a step of induced mutagenesis. Thus, the barley plant may be a barley plant prepared by a method comprising the following steps or progeny of a plant prepared by a method comprising the following steps:
  Mutagenizing barley plants or parts thereof, for example with a chemical mutagenizing agent such as $NaN_3$
  Selecting barley plants carrying any of the aforementioned mutations in the CslF6 gene.

In one embodiment, said mutation of the CslF6 gene resulting in a mutant CslF6 gene encoding a mutant CslF6 polypeptide, wherein said mutant CslF6 polypeptide is CslF6 of SEQ ID NO:1 OR SEQ ID NO:3 except that mutant CslF6 comprises a substitution of amino acid 847 to a charged amino acid, e.g. to glutamic acid. In particular said mutant CslF6 gene may carry a G→A mutation of nucleotide 2243 of the coding sequence of the HvCslF6 gene (SEQ ID NO:2).

Items

The invention may further be defined by the following items:

1. A barley plant or a part thereof, wherein the kernels of said barley plant have a reduced (1,3;1,4)-β-glucan content, and wherein said barley plant carries a mutation in the CslF6 gene, wherein said mutated CslF6 gene encodes a mutant CslF6 polypeptide, wherein said mutant CslF6 is CslF6 of SEQ ID NO:1 except that mutant CslF6 comprises a substitution of one amino acid in a membrane localised domain of CslF6, wherein said substitution is substitution of a non-polar amino acid for a charged amino acid or substitution of a polar amino acid for a non-polar amino acid, wherein the membrane localised domains of CslF6 consists of amino acids 109 to 128, 137 to 158, 700 to 731, 741 to 758, 835 to 857, and 864 to 882 of SEQ ID NO:1 OR SEQ ID NO:3.
2. A barley plant or a part thereof, wherein the kernels of said barley plant have a reduced (1,3;1,4)-β-glucan content, and wherein said barley plant carries a mutation in the CslF6 gene, wherein said mutated CslF6 gene encodes a mutant CslF6 polypeptide, wherein said mutant CslF6 is CslF6 of SEQ ID NO:1 except that mutant CslF6 comprises at least one substitution of an amino acid in a membrane localised domain of CslF6, wherein said substitution is substitution of a non-polar amino acid to a charged amino acid or substitution of a polar amino acid to a non-polar amino acid, wherein the membrane localised domain is selected from the group consisting of the membrane localised domains of CslF6 consisting of amino acids 835 to 857 or of amino acids 700 to 731 or of amino acids 741 to 758 of SEQ ID NO:1 OR SEQ ID NO:3.
3. The barley plant according to any one of the preceding items, wherein said barley plant have a (1,3;1,4)-β-glucan content in the range of 1 to 5% dry weight of total kernels, for example 1.3 to 3% dry weight of total kernels, preferably 1.3 to 2% dry weight of total kernels.
4. The barley plant according to any one of any one of the preceding items, wherein kernels of said barley plant have a (1,3;1,4)-β-glucan content of at least 30% and at most 60%, preferably at least 40% and at most 60% of the (1,3;1,4)-β-glucan content of a barley plant carrying a wild type CslF6 gene, but otherwise of the same genotype.
5. The barley plant according to any one of the preceding items, wherein kernels of said barley plant have a (1,3;1,4)-β-glucan content of at least 30% and at most 60%, preferably at least 40% and at most 60% of the (1,3;1,4)-β-glucan content of a barley plant carrying a wild type CslF6 gene, but otherwise of the same genotype.
6. The barley plant according to any one of the preceding items, wherein the barley plant comprises grains having a frequency of broken grains after threshing, which is at the most 3 times higher than the frequency of a broken grains after threshing of grains of a barley plant not carrying the mutation in the CslF6 gene, but otherwise of the same genotype.
7. The barley plant according to any one of the preceding items, wherein the barley plant comprises grains having a frequency of broken grains after threshing, which is at the most 2 times higher than the frequency of a broken grains after threshing of grains of a barley plant not carrying the mutation in the CslF6 gene, but otherwise of the same genotype.
8. The barley plant according to any one of the preceding items, wherein said substitution is substitution of a non-polar amino acid to a charged amino acid.
9. The barley plant according to any one of the preceding items, wherein said mutant CslF6 polypeptide is CslF6 of SEQ ID NO:1 OR SEQ ID NO:3 except that mutant CslF6 comprises a substitution of one amino acid in the transmembrane domain consisting of amino acids 835 to 857 of CslF6, wherein said substitution is substitution of a non-polar amino acid to a charged amino acid.
10. The barley plant according to any one of the preceding items, wherein said mutant CslF6 polypeptide is CslF6 of SEQ ID NO:1 OR SEQ ID NO:3 except that mutant CslF6 comprises a substitution of amino acid 847 to a charged amino acid.
11. The barley plant according to any one of the preceding items, wherein said mutant CslF6 polypeptide is CslF6 of SEQ ID NO:1 OR SEQ ID NO:3 except that mutant CslF6 comprises a substitution of amino acid 847, wherein said substitution is substitution of a glycine (G) to a glutamic acid (E).
12. The barley plant according to any one of the preceding items, wherein said barley plant carries a mutation in the CslF6 gene, wherein said mutated CslF6 gene encodes a mutant CslF6 polypeptide of SEQ ID NO:27.
13. The barley plant according to any one of the preceding items, wherein said barley plant carries a G→A mutation of nucleotide 2243 of the coding sequence of the HvCslF6 gene.
14. The barley plant according to item 13, wherein the coding sequence of the HvCslF6 gene is SEQ ID NO 2.
15. The barley plant according to any one of the preceding items, wherein the barley plant is Mutant 2 deposited with NCIMB under the accession number NCIMB 43273, or progeny thereof.
16. A barley plant or progeny thereof or parts thereof, wherein the genome of said plant, comprises the CslF6 gene of barley plant Mutant 2 deposited with NCIMB under the accession number NCIMB 43273.
17. The barley plant according to any one of the preceding items, wherein the kernels of said barley plant have a β-glucan content in the range of 1.7 to 5.0 dry weight of total kernels.
18. The barley plant according to any one of the preceding items, wherein the kernels of said barley plant have a DP3:DP4 ratio of at the most 2.5, such as at the most 2.1, for example in the range of 1.0 to 2.1.
19. The barley plant according to any one of the preceding items, wherein said mutant CslF6 polypeptide is CslF6 of SEQ ID NO:1 OR SEQ ID NO:3 except that mutant CslF6 comprises a substitution of one amino acid in the transmembrane domain consisting of amino acids 741 to 758 of CslF6, wherein said substitution is substitution of a non-polar amino acid to a charged amino acid.
20. The barley plant according to any one of items 1 to 8 and 19, wherein said mutant CslF6 polypeptide is CslF6 of SEQ ID NO:1 OR SEQ ID NO:3 except that mutant CslF6 comprises a substitution of amino acid 748 to a charged amino acid.
21. The barley plant according to any one of items 1 to 8 and 19 to 20, wherein said mutant CslF6 polypeptide is CslF6 of SEQ ID NO:1 OR SEQ ID NO:3 except that mutant CslF6 comprises a substitution of amino acid 748, wherein said substitution is substitution of a glycine (G) for an aspartic acid (D).
22. The barley plant according to any one of items 1 to 8 and 19 to 21, wherein the kernels of said barley plant have a β-glucan content in the range of 1.7 to 3 dry weight of total kernels.
23. The barley plant according to any one of items 1 to 8 and 19 to 22, wherein the kernels of said barley plant have a DP3:DP4 ratio in the range of 2.5 to 4.
24. The barley plant according to any one of items 1 to 8, wherein said mutant CslF6 polypeptide is CslF6 of SEQ ID NO:1 OR SEQ ID NO:3 except that mutant CslF6 comprises a substitution of one amino acid in the transmembrane domain consisting of amino acids 700 to 731 of CslF6, wherein said substitution is substitution of a polar amino acid to a non-polar amino acid.
25. The barley plant according to any one of items 1 to 8 and 24, wherein said mutant CslF6 polypeptide is CslF6 of SEQ ID NO:1 OR SEQ ID NO:3 except that mutant CslF6 comprises a substitution of one amino acid in the membrane localised domain consisting of amino acids 700 to 711 of CslF6, wherein said substitution is substitution of a polar amino acid to a non-polar amino acid.
26. The barley plant according to any one of items 1 to 8 and 24 to 25, wherein said mutant CslF6 polypeptide is CslF6 of SEQ ID NO:1 OR SEQ ID NO:3 except that mutant CslF6 comprises a substitution of amino acid 709 to a non-polar amino acid.
27. The barley plant according to any one of items 1 to 8 and 24 to 26, wherein said mutant CslF6 polypeptide is CslF6 of SEQ ID NO:1 OR SEQ ID NO:3 except that mutant CslF6 comprises a substitution of amino acid 709, wherein said substitution is substitution of a threonine (T) to an isoleucine (I).
28. The barley plant according to any one of items 1 to 8 and 24 to 27, wherein the kernels of said barley plant have a β-glucan content in the range of 1.3 to 3 dry weight of total kernels.
29. The barley plant according to any one of items 1 to 8 and 24 to 28, wherein the kernels of said barley plant have a DP3:DP4 ratio of at least 3.5, such as of at least 4.0, for example at least 4.5, such as in the range of 4 to 6.
30. The barley plant according to any one of the preceding items or progeny thereof, wherein said barley plant has not exclusively been prepared by an essentially biological method.
31. The barley plant according to any one of the preceding items or progeny thereof, wherein the barley plant is prepared by a method comprising the following steps:
   Mutagenizing barley plants or parts thereof, for example with a chemical mutagenizing agent
   Selecting barley plants carrying any of the aforementioned mutations in the CslF6 gene.
32. A plant product comprising the barley plant according to any one of the preceding items or a part thereof.
33. The plant product according item 32, wherein the plant product is green malt or kiln dried malt prepared from kernels of said barley plant.
34. The plant product according item 32, wherein the plant product is wort prepared from kernels of said barley plant and/or from green malt or kiln dried malt comprising processed kernel(s) of said barley plant.
35. The plant product according to any one of items 32 to 34, wherein the plant product is wort, and wherein said wort has a viscosity of at the most 2.5 mPa*s, preferably of at the most 2.2 mPa*s.
36. The plant product according to item 32, wherein the plant product is a beverage prepared from said barley plant of parts thereof.
37. The beverage according to item 32, wherein said beverage is prepared from kernels of said barley plant and/or from malt comprising processed kernel(s) of said barley plant.
38. The beverage according to any one of items 36 to 37, wherein the beverage is beer.
39. A method of preparing green malt, said method comprising the steps of
   a. providing kernels of a barley plant according to any one of items 1 to 31;
   b. steeping said kernels;
   c. germinating the steeped kernels under predetermined conditions.
40. A method of preparing kiln dried malt, said method comprising the steps of
   a. providing kernels of a barley plant according to any one of items 1 to 31;
   b. steeping said kernels;
   c. germinating the steeped kernels under predetermined conditions;
   d. drying said germinated kernels.
41. A method of producing a beverage, said method comprising the steps of:
   a. Providing kernels of a barley plant according to any one of items 1 to 31 and/or malt according to items 33
   b. Preparing an aqueous extract of said kernels and/or said malt
   c. processing said aqueous extract into a beverage.
42. A method of producing an aqueous extract, said method comprising the steps of:
   a. providing kernels of a barley plant according to any one of items 1 to 31;
   b. subjecting the barley kernels to a step of germination thereby obtaining germinated kernels, wherein said step of germination comprises incubating said kernels in an aqueous solution for at the most 72 h;
   c. finely dividing said germinated kernels, while said germinated kernels have a water content of at least 20%, with the proviso that said barley kernels do not have a water content below 20% at any time between steps b) and c);
   d. preparing an aqueous extract of said milled germinated kernels, thereby producing an aqueous extract of the barley.
43. A method of producing an aqueous extract, said method comprising the steps of:
   a. providing kernels of a barley plant according to any one of items 1 to 31;
   b. subjecting the barley kernels to a step of germination thereby obtaining germinated kernels, wherein said step of germination comprises incubating said kernels in an aqueous solution for at the most 72 h;
   c. finely dividing said germinated kernels, while said germinated kernels have a water content of at least 20%, with the proviso that said barley kernels do not have a water content below 20% at any time following germination and until finely dividing the germinated kernels;
d. preparing an aqueous extract of said milled germinated kernels, thereby producing an aqueous extract of the barley.
44. The method according to any one of items 42 and 43, wherein said step of germination (b) comprises incubating said kernels in an aqueous solution until the kernels have a water content of at least 30%, wherein at least 2 L O$_2$ per kg dry weight barley grains is passed through said aqueous solution per h.
45. The method according to any one of items 42 to 44, wherein the kernels of the barley are submerged in the aqueous solution during the entire step of germination.
46. The method according to any one of items 42 to 45, wherein the step of germination comprises
    a. at least one step of incubating said kernels in an aqueous solution, wherein at least 2 L O$_2$ per kg dry weight barley kernels is passed through said aqueous solution per h; and
    b. at least one step of incubating said barley kernels in air.
47. The method according to any one of items 42 to 46, wherein at least 3 L, more preferably at least 4 L, yet more preferably at least 5 L, even more preferably at least 6 L O$_2$ per kg dry weight of barley kernels is passed through said aqueous solution per h.
48. The method according to any one of items 42 to 47, wherein said O$_2$ is comprised within a gas mixture, wherein the gas mixture is atmospheric air.
49. The method according to any one of items 42 to 48, wherein the entire step of germination does not exceed 72 h, more preferably does not exceed 60 h, even more preferably does not exceed 54 h.
50. The method according to any one of items 42 to 49, wherein the barley is hulled barley, and the method comprises a step of removing at least part of said hull prior to incubating said kernels in an aqueous solution.
51. A method for producing a beverage, said method comprising the steps of:
    a. preparing an aqueous extract by the method according to any one of items 42 to 50;
    b. processing said extract into a beverage.
52. The method according to item 51, wherein step b. comprises the steps of:
    i. heating said aqueous extract optionally in the presence of hops or hops extract;
    ii. cooling the aqueous extract;
    iii. fermenting said aqueous extract with yeast, thereby producing a fermented beverage.
53. The method according to any one of items 51 to 52, wherein the beverage is beer.
54. A method of preparing a barley plant with a β-glucan content in the range of 1 to 5% dry weight of total kernels, the method comprising the steps of
    a. providing barley kernels; and
    b. randomly mutagenising said barley kernels, thereby introducing a mutation in the in the CslF6 gene, wherein said mutated CslF6 gene encodes a mutant CslF6 polypeptide, wherein said mutant CslF6 is CslF6 of SEQ ID NO:1 OR SEQ ID NO:3 except that mutant CslF6 comprises a substitution of one amino acid in a transmembrane domain of CslF6, wherein said substitution is substitution of a non-polar amino acid for a charged amino acid or substitution of a polar amino acid for a non-polar amino acid, wherein the transmembrane domains of CslF6 consists of amino acids 109 to 128, 137 to 158, 700 to 731, 741 to 758, 835 to 857, and 864 to 882; and
    c. selecting barley kernels or progeny thereof carrying a mutated CslF6 gene.
55. The method according to item 54, wherein the barley plant or the mutation is as defined in any one of items 1 to 31.
56. The barley plant according to any one of items 1 to 31, wherein the barley plant comprises a mutation in one or more additional genes, for example one or more of the following mutations:
    a. a mutation in the gene encoding LOX-1 resulting in a total loss of functional LOX-1
    b. a mutation in the gene encoding LOX-2 resulting in a total loss of functional LOX-2
    c. a mutation in the gene encoding MMT resulting in a total loss of functional MMT.

```
Sequences
>SEQ ID NO: 1, Cellulose synthase-like CsIF6
sequence (based on GenBank number NCBI:
EU267181.1)
MAPAVAGGGRVRSNEPVAAAAAAPAASGKPCVCGFQVCACTGSAAVASAA

SSLDMDIVAMGQIGAVNDESWVGVELGEDGETDESGAAVDDRPVFRTEKI

KGVLLHPYRVLIFVRLIAFTLFVIWRISHKNPDAMWLWVTSICGEFWFGF

SWLLDQLPKLNPINRVPDLAVLRQRFDRPDGTSTLPGLDIFVTTADPIKE

PILSTANSVLSILAADYPVDRNTCYVSDDSGMLLTYEALAESSKFATLWV

PFCRKHGIEPRGPESYFELKSHPYMGRAQDEFVNDRRRVRKEYDEFKARI

NSLEHDIKQRNDGYNAAIAHSQGVPRPTWMADGTQWEGTWVDASENHRRG

DHAGIVLVLLNHPSHRRQTGPPASADNPLDLSGVDVRLPMLVYVSREKRP

GHDHQKKAGAMNALTRASALLSNSPFILNLDCDHYINNSQALRAGICFMV

GRDSDTVAFVQFPQRFEGVDPTDLYANHNRIFFDGTLRALDGMQGPIYVG

TGCLFRRITVYGFDPPRINVGGPCFPRLAGLFAKTKYEKPGLEMTTAKAK

AAPVPAKGKHGFLPLPKKTYGKSDAFVDTIPRASHPSPYAAAAEGIVADE

ATIVEAVNVTAAAFEKKTGWGKEIGWVYDTVTEDVVTGYRMHIKGWRSRY

CSIYPHAFIGTAPINLTERLFQVLRWSTGSLEIFFSKNNPLFGSTYLHPL

QRVAYINITTYPFTAIFLIFYTTVPALSFVTGHFIVQRPTTMFYVYLGIV

LSTLLVIAVLEVKWAGVTVFEWFRNGQFWMTASCSAYLAAVCQVLTKVIF

RRDISFKLTSKLPSGDEKKDPYADLYVVRWTPLMITPIIIIFVNIIGSAV

AFAKVLDGEWTHWLKVAGGVFFNFWVLFHLYPFAKGILGKHGKTPVVVLV

WWAFTFVITAVLYINIPHMHTSGGKHTTVHGHHGKKLVDTGLYGWLH

>SEQ ID NO: 2, Hordeum vulgare cellulose synthase-
like CsIF6 (CsIF6), complete cds(based on GenBank
number NCBI: EU267181.1)
ATGGCGCCAGCGGTGGCCGGAGGGGGCCGCGTGCGGAGCAATGAGCCGGT

TGCTGCTGCTGCCGCCGCGCCGGCGGCCAGCGGCAAGCCCTGCGTGTGCG

GCTTCCAGGTTTGCGCCTGCACGGGGTCGGCCGCGGTGGCCTCCGCCGCC

TCGTCGCTGGACATGGACATCGTGGCCATGGGGCAGATCGGCGCCGTCAA

CGACGAGAGCTGGGTGGGCGTGGAGCTCGGCGAAGATGGCGAGACCGACG

AAAGCGGTGCCGCCGTTGACGACCGCCCCGTATTCCGCACCGAGAAGATC
```

```
AAGGGTGTCCTCCTCCACCCCTACCGGGTGCTGATTTTCGTTCGTCTGAT
CGCCTTCACGCTGTTCGTGATCTGGCTATCTCCCACAAGAACCCAGACG
CGATGTGGCTGTGGGTGACATCCATCTGCGGCGAGTTCTGGTTCGGTTTC
TCGTGGCTGCTAGATCAGCTGCCCAAGCTGAACCCCATCAACCGCGTGCC
GGACCTGGCGGTGCTGCGGCAGCGCTTCGACCGCCCCGACGGCACCTCCA
CGCTCCCGGGGCTGGACATCTTCGTCACCACGGCCGACCCCATCAAGGAG
CCCATCCTCTCCACCGCCAACTCGGTGCTCTCCATCCTGGCCGCCGACTA
CCCCGTGGACCGCAACACATGCTACGTCTCCGACGACAGTGGCATGCTGC
TCACCTACGAGGCCCTGGCAGAGTCCTCCAAGTTCGCCACGCTCTGGGTG
CCCTTCTGCCGCAAGCACGGGATCGAGCCCAGGGGTCCGGAGAGCTACTT
CGAGCTCAAGTCACACCCTTACATGGGGAGAGCCCAGGACGAGTTCGTCA
ACGACCGCCGCCGCGTTCGCAAGGAGTACGACGAGTTCAAGGCCAGGATC
AACAGCCTGGAGCATGACATCAAGCAGCGCAACGACGGGTACAACGCCGC
CATTGCCCACAGCCAAGGCGTGCCCCGGCCCACCTGGATGGCGGACGGCA
CCCAGTGGGAGGGCACATGGGTCGACGCCTCCGAGAACCACCGCAGGGGC
GACCACGCCGGCATCGTACTGGTGCTGCTGAACCACCCGAGCCACCGCCG
GCAGACGGGCCCGCCGGCGAGCGCTGACAACCCACTGGACTTGAGCGGCG
TGGATGTGCGTCTCCCCATGCTGGTGTACGTGTCCCGTGAGAAGCGCCCC
GGGCACGACCACCAGAAGAAGGCCGGTGCCATGAACGCGCTTACCCGCGC
CTCGGCGCTGCTCTCCAACTCCCCCTTCATCCTCAACCTCGACTGCGATC
ATTACATCAACAACTCCCAGGCCCTTCGCGCCGGCATCTGCTTCATGGTG
GGACGGGACAGCGACACGGTTGCCTTCGTCCAGTTCCCGCAGCGCTTCGA
GGGCGTCGACCCCACCGACCTCTACGCCAACCACAACCGCATCTTCTTCG
ACGGCACCCTCCGTGCCCTGGACGGCATGCAGGGCCCCATCTACGTCGGC
ACTGGGTGTCTCTTCCGCCGCATCACCGTCTACGCTTCGACCCGCCGAG
GATCAACGTCGGCGGTCCCTGCTTCCCCAGGCTCGCCGGGCTCTTCGCCA
AGACCAAGTACGAGAAGCCCGGGCTCGAGATGACCACGGCCAAGGCCAAG
GCCGCGCCCGTGCCCGCCAAGGGTAAGCACGGCTTCTTGCCACTGCCCAA
GAAGACGTACGGCAAGTCGGACGCCTTCGTGGACACCATCCCGCGCGCGT
CGCACCCGTCGCCCTACGCCGCGGCGGCTGAGGGGATCGTGGCCGACGAG
GCGACCATCGTCGAGGCGGTGAACGTGACGGCCGCCGCGTTCGAGAAGAA
GACCGGCTGGGGCAAAGAGATCGGCTGGGTGTACGACACCGTCACGGAGG
ACGTGGTCACCGGCTACCGGATGCATATCAAGGGGTGGCGGTCACGCTAC
TGCTCCATCTACCCACACGCCTTCATCGGCACCGCCCCCATCAACCTCAC
GGAGAGGCTCTTCCAGGTGCTCCGCTGGTCCACGGGATCCCTCGAGATCT
TCTTCTCCAAGAACAACCCGCTCTTCGGCAGCACATACCTCCACCCGCTG
CAGCGCGTCGCCTACATCAACATCACCACTTACCCCTTCACCGCCATCTT
CCTCATCTTCTACACCACCGTGCCGGCGCTATCCTTCGTCACCGGCCACT
TCATCGTGCAGCGCCCGACCACCATGTTCTACGTCTACCTGGGCATCGTG
CTATCCACGCTGCTCGTCATCGCCGTGCTGGAGGTCAAGTGGGCCGGGGT
CACAGTCTTCGAGTGGTTCAGGAACGGCCAGTTCTGGATGACAGCAAGTT

GCTCCGCCTACCTCGCCGCCGTCTGCCAGGTGCTGACCAAGGTGATATTC
CGGCGGGACATCTCCTTCAAGCTCACATCCAAGCTACCCTCGGGAGACGA
GAAGAAGGACCCCTACGCCGACCTCTACGTGGTGCGCTGGACGCCGCTCA
TGATTACACCCATCATCATCATCTTCGTCAACATCATCGGATCCGCCGTG
GCCTTCGCCAAGGTTCTCGACGGCGAGTGGACGCACTGGCTCAAGGTCGC
CGGCGGCGTCTTCTTCAACTTCTGGGTGCTCTTCCACCTCTACCCCTTCG
CCAAGGGCATCCTGGGGAAGCACGGAAAGACGCCAGTCGTGGTGCTCGTC
TGGTGGGCATTCACCTTCGTCATCACCGCCGTGCTCTACATCAACATCCC
CCACATGCATACCTCGGGAGGCAAGCACACAACGGTGCATGGTCACCATG
GCAAGAAGTTGGTCGACACAGGGCTCTATGGCTGGCTCCATTGA

>SEQ ID NO: 3, Cellulose synthase-like CsIF6
sequence (containing A590T polymorphism)
MAPAVAGGGRVRSNEPVAAAAAAPAASGKPCVCGFQVCACTGSAAVASAA
SSLDMDIVAMGQIGAVNDESWVGVELGEDGETDESGAAVDDRPVFRTEKI
KGVLLHPYRVLIFVRLIAFTLFVIWRISHKNPDAMWLWVTSICGEFWFGF
SWLLDQLPKLNPINRVPDLAVLRQRFDRPDGTSTLPGLDIFVTTADPIKE
PILSTANSVLSILAADYPVDRNTCYVSDDSGMLLTYEALAESSKFATLWV
PFCRKHGIEPRGPESYFELKSHPYMGRAQDEFVNDRRRVRKEYDEFKARI
NSLEHDIKQRNDGYNAAIAHSQGVPRPTWMADGTQWEGTWVDASENHRRG
DHAGIVLVLLNHPSHRRQTGPPASADNPLDLSGVDVRLPMLVYVSREKRP
GHDHQKKAGAMNALTRASALLSNSPFILNLDCDHYINNSQALRAGICFMV
GRDSDTVAFVQFPQRFEGVDPTDLYANHNRIFFDGTLRALDGMQGPIYVG
TGCLFRRITVYGFDPPRINVGGPCFPRLAGLFAKTKYEKPGLEMTTAKAK
AAPVPAKGKHGFLPLPKKTYGKSDAFVDTIPRASHPSPYTAAAEGIVADE
ATIVEAVNVTAAAFEKKTGWGKEIGWVYDTVTEDVVTGYRMHIKGWRSRY
CSIYPHAFIGTAPINLTERLFQVLRWSTGSLEIFFSKNNPLFGSTYLHPL
QRVAYINITTYPFTAIFLIFYTTVPALSFVTGHFIVQRPTTMFYVYLGIV
LSTLLVIAVLEVKWAGVTVFEWFRNGQFWMTASCSAYLAAVCQVLTKVIF
RRDISFKLTSKLPSGDEKKDPYADLYVVRWTPLMITPIIIIFVNIIGSAV
AFAKVLDGEWTHWLKVAGGVFFNFWVLFHLYPFAKGILGKHGKTPVVVLV
WWAFTFVITAVLYINIPHMHTSGGKHTTVHGHHGKKLVDTGLYGWLH >SEQ ID NO: 27, Cell Wall mutant 2 (CW3a) based on
SEQ ID NO: 1, Cellulose synthase-like CsIF6
sequence (based on GenBank number NCBI: EU267181.1)
MAPAVAGGGRVRSNEPVAAAAAAPAASGKPCVCGFQVCACTGSAAVASAA
SSLDMDIVAMGQIGAVNDESWVGVELGEDGETDESGAAVDDRPVFRTEKI
KGVLLHPYRVLIFVRLIAFTLFVIWRISHKNPDAMWLWVTSICGEFWFGF
SWLLDQLPKLNPINRVPDLAVLRQRFDRPDGTSTLPGLDIFVTTADPIKE
PILSTANSVLSILAADYPVDRNTCYVSDDSGMLLTYEALAESSKFATLWV
PFCRKHGIEPRGPESYFELKSHPYMGRAQDEFVNDRRRVRKEYDEFKARI
NSLEHDIKQRNDGYNAAIAHSQGVPRPTWMADGTQWEGTWVDASENHRRG
```

-continued

DHAGIVLVLLNHPSHRRQTGPPASADNPLDLSGVDVRLPMLVYVSREKRP

GHDHQKKAGAMNALTRASALLSNSPFILNLDCDHYINNSQALRAGICFMV

GRDSDTVAFVQFPQRFEGVDPTDLYANHNRIFFDGTLRALDGMQGPIYVG

TGCLFRRITVYGFDPPRINVGGPCFPRLAGLFAKTKYEKPGLEMTTAKAK

AAPVPAKGKHGFLPLPKKTYGKSDAFVDTIPRASHPSPYAAAAEGIVADE

ATIVEAVNVTAAAFEKKTGWGKEIGWVYDTVTEDVVTGYRMHIKGWRSRY

CSIYPHAFIGTAPINLTERLFQVLRWSTGSLEIFFSKNNPLFGSTYLHPL

QRVAYINITTYPPFTAIFLIFYTTVPALSFVTGHFIVQRPTTMFYVYLDIV

LSTLLVIAVLEVKWAGVTVFEWFRNGQFWMTASCSAYLAAVCQVLTKVIF

RRDISFKLTSKLPSGDEKKDPYADLYVVRWTPLMITPIIIIFVNIIGSAV

AFAKVLDGEWTHWLKVAGGVFFNFWVLFHLYPFAKGILGKHGKTPVVVLV

WWAFTFVITAVLYINIPHMHTSGGKHTTVHGHHGKKLVDTGLYGWLH

EXAMPLES

Example 1

Design of Digital Mutant Identification Probes

The coding sequence of HvCslF6 gene was collected from the National Center for Biotechnology Information (NCBI) under the accession number AB621332. This sequence was used for a BLAST search on: webblast.ipk-gatersleben.de. The HvCslF6 gene and transcript sequences were retrieved under the accession number: MLOC_57200 using: plants.ensembl.org. The digital mutant identification probes were designed based on the coding DNA and protein sequence of MLOC_57200.2.

Example 2

Screening for Barley Mutants with Specific Mutations in the Gene for Cellulose Synthase-Like CslF6.

Altogether 5 mutants with a specific mutation, leading to the substitution of an amino acid residue in cellulose synthase-like CslF6 (HvCslF6), were identified (Table 1).

TABLE 1

Identified mutants.

| Mutant No. | Nucleotide change in coding sequence (SEQ ID NO: 2) | Amino acid change in protein (SEQ ID NO: 1) |
|---|---|---|
| Mutant 1 | G→A (2540) | Gly→Glu (847) |
| Mutant 2 | G→A (2243) | Gly→Asp (748) |
| Mutant 3 | G→A (2028) | Trp→Stop (676) |
| Mutant 4 | G→A (2195) | Gly→Asp (732) |
| Mutant 5 | C→T (2126) | Thr→Ile (709) |

Mutant 1, mutant 2, mutant 3 and mutant 4 were identified using a ddPCR screening method essentially as described in international patent application PCT/EP2017/065516. More specifically, a pool of randomly mutagenized barley grains was prepared, followed by preparation of an ordered library as described in international patent application PCT/EP2017/065516 in WS1 and WS2 on p. 66-69 as well as in Examples 1 to 2. The mutant 1, mutant 2, mutant 3 and mutant 4 were identified and selected as described in international patent application PCT/EP2017/065516 in WS3 and WS4 on p. 67-72 as well as in Examples 3 to 15 using the primers and probes specified in Table 2 below. In particular, the screening was performed essentially as described in international patent application PCT/EP2017/065516 in WS3 and in Examples 3 to 7 using the primers and probes specified in Table 2 below. Individual barley grains carrying the gene mutation were identified essentially as described in international patent application PCT/EP2017/065516 in WS4 (p. 69-72) and in Examples 8 to 15 using the primers and probes specified in Table 2 below. Primers and probes were designed specifically for the identification of specific mutants at the HvCslF6-locus, are described in Table 2.

TABLE 2

Primers and probes designed for the specific mutants.

| Mutant | Target-specific forward primer | Target-specific reverse primer | Mutant-specific detection probe labelled with 6-carboxy-fluorescein (FAM) | Reference-specific detection probe labelled with hexachloro-fluorescein (HEX) |
|---|---|---|---|---|
| Mut1 | TACACCCATCATCATCATCT (SEQ ID NO: 4) | CGAGAACCTTGGCGA (SEQ ID NO: 5) | ATCATCGAATCCGCCG (SEQ ID NO: 6) | CATCATCGGATCCGCC (SEQ ID NO: 7) |
| Mut2 | CCGACCACCATGTTCT (SEQ ID NO: 8) | GGCGATGACGAGCAG (SEQ ID NO: 9) | CTACCTGGACATCGTGC (SEQ ID NO: 10) | CTACCTGGGCATCGTG (SEQ ID NO: 11) |
| Mut3 | ACTGCTCCATCTACCCAC (SEQ ID NO: 12) | GTATGTGCTGCCGAAGAG (SEQ ID NO: 13) | TGCTCCGCTGATCCA (SEQ ID NO: 14) | TCCGCTGGTCCACG (SEQ ID NO: 15) |
| Mut4 | CACCACCGTGCCG (SEQ ID NO: 16) | CATGGTGGTCGGGC (SEQ ID NO: 17) | CGTCACCGACCACTTC (SEQ ID NO: 18) | TCACCGGCCACTTCA (SEQ ID NO: 19) |

Mutant 5 was identified using a direct sequencing approach of 6000 mutagenized M3 barley mutants using specific primers (forward primer 5'-ACTGCTCCATC-TACCCACAC-3'; reverse primer 5'-GATGACGAAGGT-GAATGCCC-3') to amplify parts of the HvCslF6 locus.

Mutant 1, mutant 2, mutant 3, mutant 4 and mutant 5 are herein also referred to as Mut1, Mut2, Mut3, Mut4 and Mut5, respectively.

To visualise the location of the mutations, the program Swissprot (swissmodel.expasy.org/) was used to model the CslF6 protein. First the entire protein sequence is uploaded in the "model building feature" and then a model is calculated based on available data. For the CslF6 protein sequence it is recognized as having embedded in the sequence a structure resembling "Cellulose Synthase Subunit A". The program then utilizes the recognized sequence (polypeptide position 109-883) to build a model. At this stage the SwissProt program does not recognize that the protein is membrane bound, although the helixes are ordered to one side in the model. The literature indicates that the ClsF6 protein is membrane bound. Thus to further test this, QMEANBrane feature in SwissProt was used. This modeling program utilizes a PDB-file covering position 109-883 generated during the first modeling and then a new structure is build modeling the membrane and selected part of CslF6 protein together.

Figure 3:
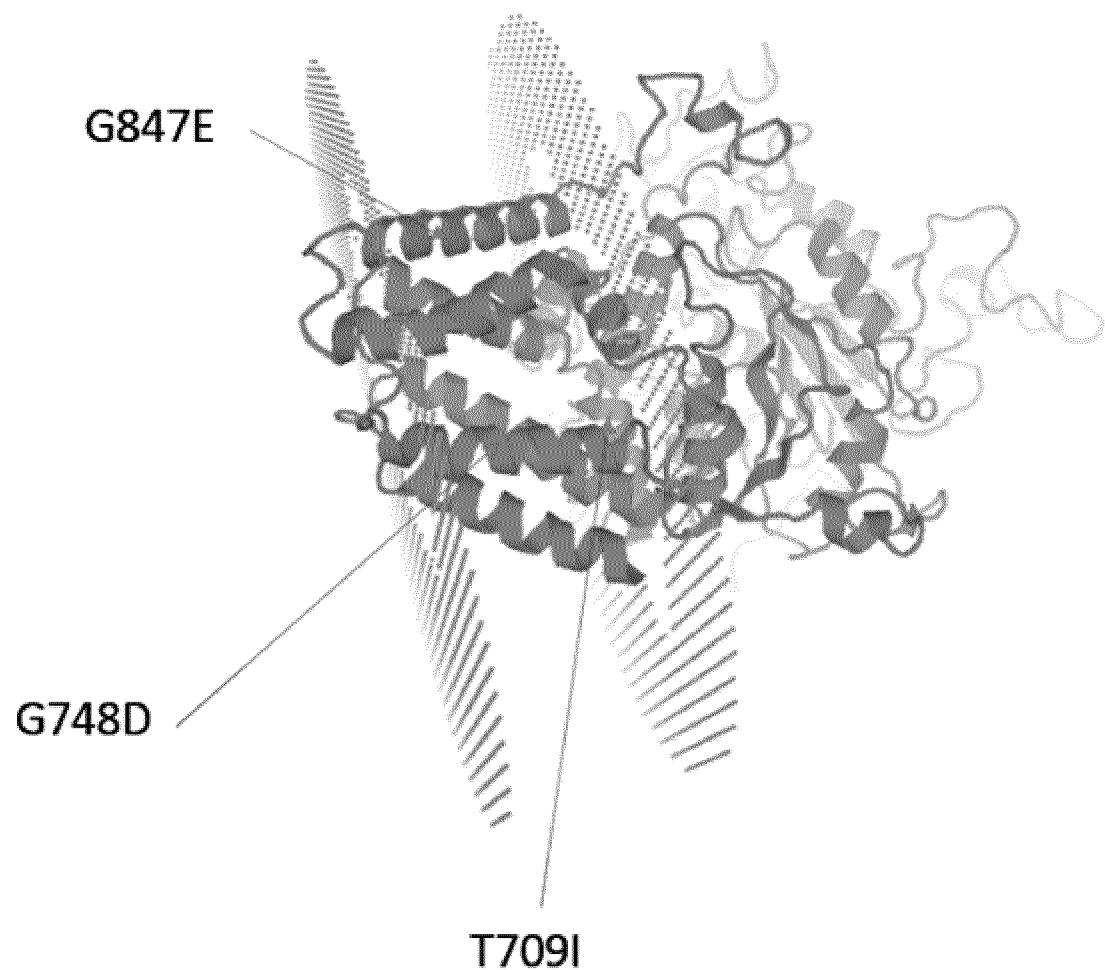
FIG. 3. Model of CslF6 protein embedded in plasma membrane. The indicated mutations represent the DMI mutants.

The two dotted grey planes resample the bi-layered membrane. The three mutations directing lower (1,3;1,4)-β-glucans content all reside in helix structures embedded in the membrane (T709I, G748D, G847E) whereas the mutation not affecting the (1,3;1,4)-β-glucans content (G732D) is located in a linker sequence facing the exterior and connecting two transmembrane domains (FIG. 3). The membrane localised amino acids in CslF6 are indicated in Table 3.

Example 3

(1,3;1,4)-β-Glucans Content and DP3:DP4 Ratio of Mature Mutant Grains

The mutants identified as described in Example 1 were grown to maturity and homozygous grains were planted in rows. At maturity the plants were harvested and grains used for propagation in small plots of few square meters. The mutants 1, 2, 4 and 5 all performed well in the field giving yields similar to the references. Accordingly, these mutants have acceptable agronomical traits. The reference was cv. Paustian for mutants 1, 2, 3 and 4, and cv. Quench for mutant 5.) Mutant 3 exhibited highly reduced fertility and was therefore not included in the yield trials.

TABLE 4 shows average yield of at least four plots of 7.5 m2. The barley was propagated at Nr Aaby in 2017.

| Mutant No | Mutant | Yield (kg) | SD |
|---|---|---|---|
| Mut1 | CW2 | 6.0 | 0.2 |
| Mut2 | CW3 | 6.2 | 0.3 |
| Mut5 | CW4 | 5.9 | 0.2 |
|  | Paustian | 6.2 | 0.2 |
| Mut4 | CW7 | 6.0 | 0.5 |
|  | Quench | 6.1 | 0.2 |

The harvested grains were analysed for total (1,3;1,4)-β-glucans content and the DP3:DP4 ratio determined. Ten ml barley grains were milled on a Retch cyclone mill. All samples were analysed in triplicates. Twenty mg of flour was weight out in 2 ml Eppendorf tubes, heated for 2 hours at

TABLE 3

Localization of membrane localized amino acid sequences in the CsIF6 protein

| AA position in SEQ ID NO: 1 or SEQ ID NO: 3 | AA sequence | Functionality |
|---|---|---|
| 109-128 | RVLIFVRLIAFTLFVIWRIS | Membrane spanning (SEQ ID NO: 20) |
| 137-158 | LWVTSICGEFWFGFSWLLDQLP | Membrane spanning (SEQ ID NO: 21) |
| 700-711 | LQRVAYINITTY | Part of membrane spanning (SEQ ID NO: 22) |
| 712-714 | PTF | Helix linker in membrane giving kink |
| 715-731 | AIFLIFYTTVPALSFVT | Part of membrane spanning (SEQ ID NO: 23) |
| 741-758 | TMFYVYLGIVLSTLLVIA | Membrane spanning (SEQ ID NO: 24) |
| 835-857 | ITPIIIIFVNIIGSAVAFAKVLD | Membrane spanning (SEQ ID NO: 25) |
| 864-882 | LKVAGGVFFNFWVLFHLYPF | Membrane spanning (SEQ ID NO: 26) |

100 degree C. in an oven followed by cooling to room temperature. In total 500 µl 50% aqueous methanol was added and the sample was shaken at 1400 rpm for 1 hour. Following centrifugation at 16000 g for 10 minutes, the supernatant was discarded and the sample dried overnight. Then 400 µl of 20 mM NaHPO4 at pH 6.5 with 1 U/ml lichenase (Megazyme, International, Ireland) was added per 10 mg flour and incubated at 50 degree C. for 2.5 hours. The sample was centrifuged at 16000 g for 10 minutes and the supernatant was filtered through 0.45 µm filters and the released Glc-β-(1→4)-Glc-β-(1→3)-Glc (DP3) and Glc-β-(1→4)-Glc-β-(1→4)-Glc-β-(1→3)-Glc (DP4) oligomers were quantified by High-performance anion exchange chromatography with pulsed amperometric detection (HPAEC-PAD). The Glc-β-(1→4)-Glc-β-(1→3)-Glc (DP3) and Glc-β-(1→4)-Glc-β-(1→4)-Glc-β-(1→3)-Glc (DP4) oligomers were quantified with HPAEC-PAD using a Dionex ICS 5000+DC system equipped with a 4 µm SA-10 column with 2×250 mm dimensions and a pre-column. Run conditions were 0.4 ml/min, column temperature 40° C., isocratic 100 mM NaOH eluent for 15 min. Standard for quantification were produced by 1 U/ml lichenase (Megazyme International, Ireland) digestion of known quantities of medium viscosity (1,3;1,4)-β-glucans (Megazyme International, Ireland) in 20 mM NaHPO4 pH 6.5 assuming an equal molar PAD response ratio between DP3 and DP4. The total (1,3;1,4)-β-glucan content was considered to be the sum of the content of DP3 and DP4 oligomers.

Figure 2:
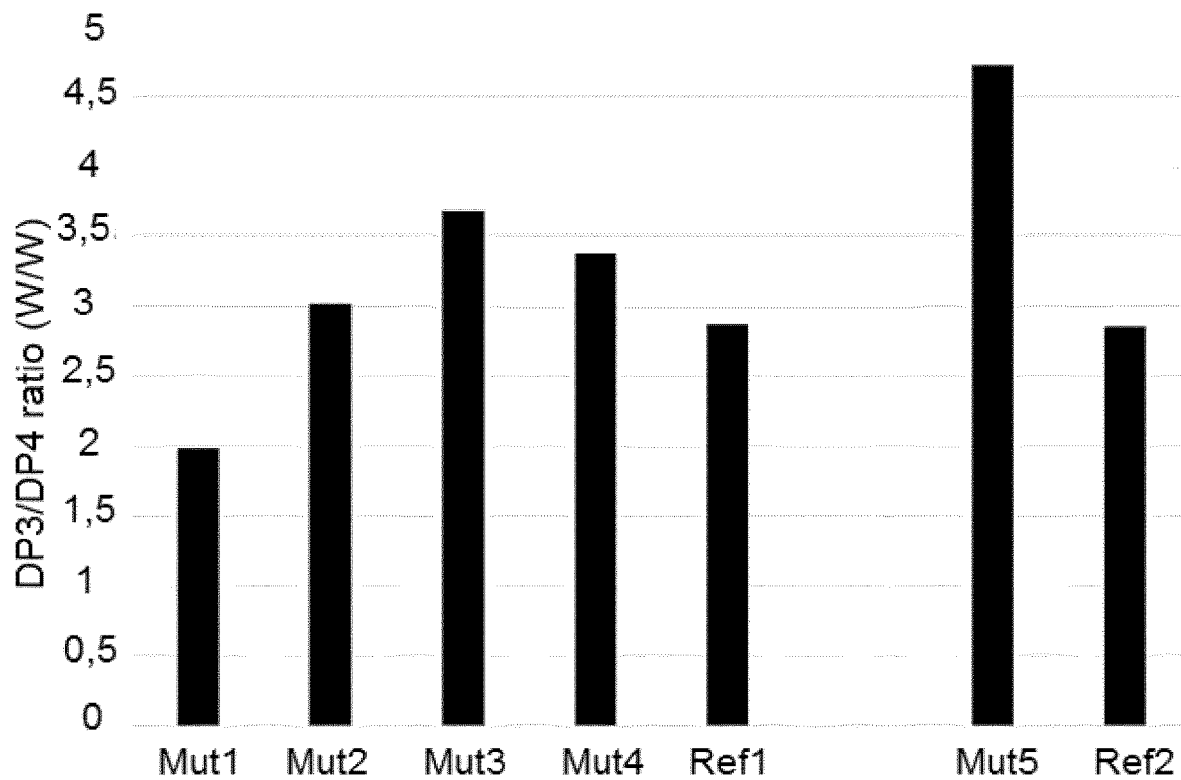

Results. The (1-3;1-4)-β-glucan content of mutants 1, 2 and 5 were all in the range of 1.4 to 2%, whereas mutant 3 had almost no (1-3;1-4)-β-glucan (FIG. 1 and Table 6). Examining the DP3:DP4 ratios mutant 1 showed a lower ratio than references, mutant 2 was similar to the references, mutants 3 and 4 slightly higher than reference and mutant 5 showed a much higher DP3:DP4 ratio (FIG. 2 and Table 6).

Example 4

(1,3;1,4)-β-Glucans Content of Mutant Grains During Accelerated Germination

Grains of mutants 1, 2 and 4 as well as of the reference (the reference was cv. Paustian for mutants 1, 2, 3 and 4, and cv. Quench for mutant 5) were subjected to a single-step steeping and germination in a tank essentially as described in Example 1 of international patent application PCT/EP2017/065498. Samples of germinating grains were taken after 24 h and 48 h.

All samples were analysed using Comprehensive Microarray Polymer Profiling (CoMPP) (Moller et al., 2007). Each sample was analysed in triplicates of 20 mg sequentially extracted with 1 ml H$_2$O at 85° C. for 1 hour at 1000 rpm and 1 ml 4 M NaOH with 0.1% v/v NaBH$_4$ at 20° C. for 2 hours at 1000 rpm. Each extraction was carried out in 2 ml Eppendorf tubes with a 3 mm glass ball followed by 10 min centrifugation at 10.000 g and the supernatant collected.

Extractions were mixed 50/50 with arrayjet printing buffer (55.2% glycerol, 44% water, 0.8% Triton X-100) and spotted unto a nitrocellulose membrane, pore size of 0.45 µm (Whatman, Maidstone, UK) using an Arrayjet Sprint (Arrayjey, Roslin, UK). Each sample was printed with four technical replicates and 3 five-fold dilutions, and probed as described in (Pedersen et al., 2012). The arrays were scanned using a flatbed scanner (CanoScan 9000 MarkII, Canon, Søborg, Denmark) at 2400 dpi and quantified using Array-Pro Analyzer 6.3 (Media Cybernetics, Rockville, Md., USA). For each sample, an average was calculated based on the four dilutions and four technical replicates resulting in 16 measurements per sample replicate signal value. The highest value in the dataset was set to a 100 and the rest adjusted accordingly. The data are presented in table 5 showing the average of the three sample replicates.

TABLE 5

(1,3;1,4)-β-glucan content of barley mutants and references. The highest value at 24 h was set to 100 and the rest adjusted accordingly

|  | % Glucan - 24 h | % Glucan - 48 h |
|---|---|---|
| Mutant 1 | 59 | 55 |
| Mutant 2 | 84 | 69 |
| Mutant 4 | 100 | 95 |
| Reference 1 | 98 | 85 |

The analysis show that Mutant 1 and 2 have lower (1,3;1,4)-β-glucan content after 24 h and 48 h during germination in a tank supplied with air compared to the reference and Mutant 4 verifying the inherent lower (1,3;1,4)-β-glucan content of mutant 1 and 2.

Example 6

Analysis of Grain Strength

Mutants 1, 2, 3, 4 and 5 as well as reference lines cv. Paustian and cv. Quench were propagated in the field in plots of 7.5 m$^2$. They were harvested with a trial Wintersteiger Classic (Wintersteiger (WINTERSTEIGER AG, Johann-Michael-Dimmelstrasse 94910 Ried im Innkreis, Austria). Further cleaning of the grains was performed on a Pfeuffer sample Cleaner, model SLN4 (Pfeuffer GmbH, Flugplatzstralle 70, 97318 Kitzingen, Germany) using a 2.5 mm screen. Broken grains were counted in four randomly selected samples of approximately 10 g and the amount of broken grains was calculated on weight basis. The number of broken grains after threshing (Wintersteiger test) and prior to screening is an indication of grain strength. The rate of broken grains after threshing was calculated as fold increase in broken grains in mutant plants relative to the reference wildtype plants (reference plants indicated in Table 6a).

TABLE 6a

Summary of mutant grain characteristics

| Patent notation | Beta-glucan in flour (%) | w/w DP3/DP4 ratio | % beta-glucan of reference | Broken grains (%) |
|---|---|---|---|---|
| Mut 1 | 1.7 | 2.0 | 50 | 4.4 |
| Mut 2 | 1.9 | 3.0 | 54 | 2.7 |
| Mut 3 | 0.1 | 3.7 | 2 | ND |
| Mut 4 | 3.3 | 3.4 | 94 | 1.2 |
| Ref 1 - Cv. Paustian | 3.5 | 2.9 | 100 | 1.6 |
| Mut 5 | 1.4 | 4.7 | 44 | 3.2 |
| Ref 2 - Cv. Quench | 3.2 | 2.8 | 100 | 2.1 |

A similar determination of the percentage of broken grains (the threshing broken rate) was performed on 50 g samples from barley plants grown in New Zealand 2016-2017 (Mut 1; Mut 2; Mut 4; Mut 5) and in Denmark 2018 (Mut 2). The frequency of broken grains after threshing (threshing broken rate) was determined as described above and the compared to the frequency of the wild type reference barley plants (cv. Paustian for Mut 1, Mut 2 and Mut 4 and cv. Quench for Mut. 5). The fold increase compared to the wild type reference barley plants is indicated in Table 6b below.

TABLE 6b

| Barley line | Mutation compared to SEQ ID NO: 1 | Fold increase in broken grains 2017 | Fold increase in broken grains 2018 |
|---|---|---|---|
| Mut 1 | G847E | 2.7 | |
| Mut 2 | G748D | 1.7 | 1.9 |
| Mut 4 | G732D | 0.8 | |
| Mut 5 | T709I | 1.5 | |

Interesting, Hu et al., 2014 discloses a barley line (m351) carrying a mutation in the CslF6 gene resulting in a A849T mutation of the CslF6 protein. Said barley line has a 4.2 fold increase of the rate of broken grains compared to the wild type control.

Example 7

Hydrolytic Enzyme Activity in Malt Samples

Barley kernels of mutant 2 and of the reference (cv. Paustian) were processed in triplicates, 50 g each sample. Mutant 2 was as described in Example 2 above). Dry barley kernels placed in stainless steel beakers were micromalted according to standard methods. Briefly, the barley kernels were as a forced submission in 15° C. fresh water for about 7 hours on the first day, 3 hours on the second day and one hour on the third day, as to reach a water content of 35%, 40% and 45%, respectively, at the end of each steeping. After each steeping, the stainless steel beakers containing the samples were moved to a germination box at 15° C. and kept there until the following step in the process. At the end of the last drainage of steeping water, samples were kept for 120 hours (Days 3-7) in germination boxes equilibrated to 45% water and sprayed to overcome respiration water loss.

At the end of the germination process (Day 7), samples were kiln dried in the stainless steel boxes into a Termaks incubator for 21 hours using the following temperature ramp program:
25° C.-55° C. (2° C./hrs)
55° C.-85° C. (4° C./hrs)
85° C. for 1.5 hours The steps of germination and kiln-drying were performed with a recirculating airflow of 80% fresh air.

At the end of each micromalting day, samples were collected for analyses, in triplicate, and freeze dried for 48 hours.

Figure 5:
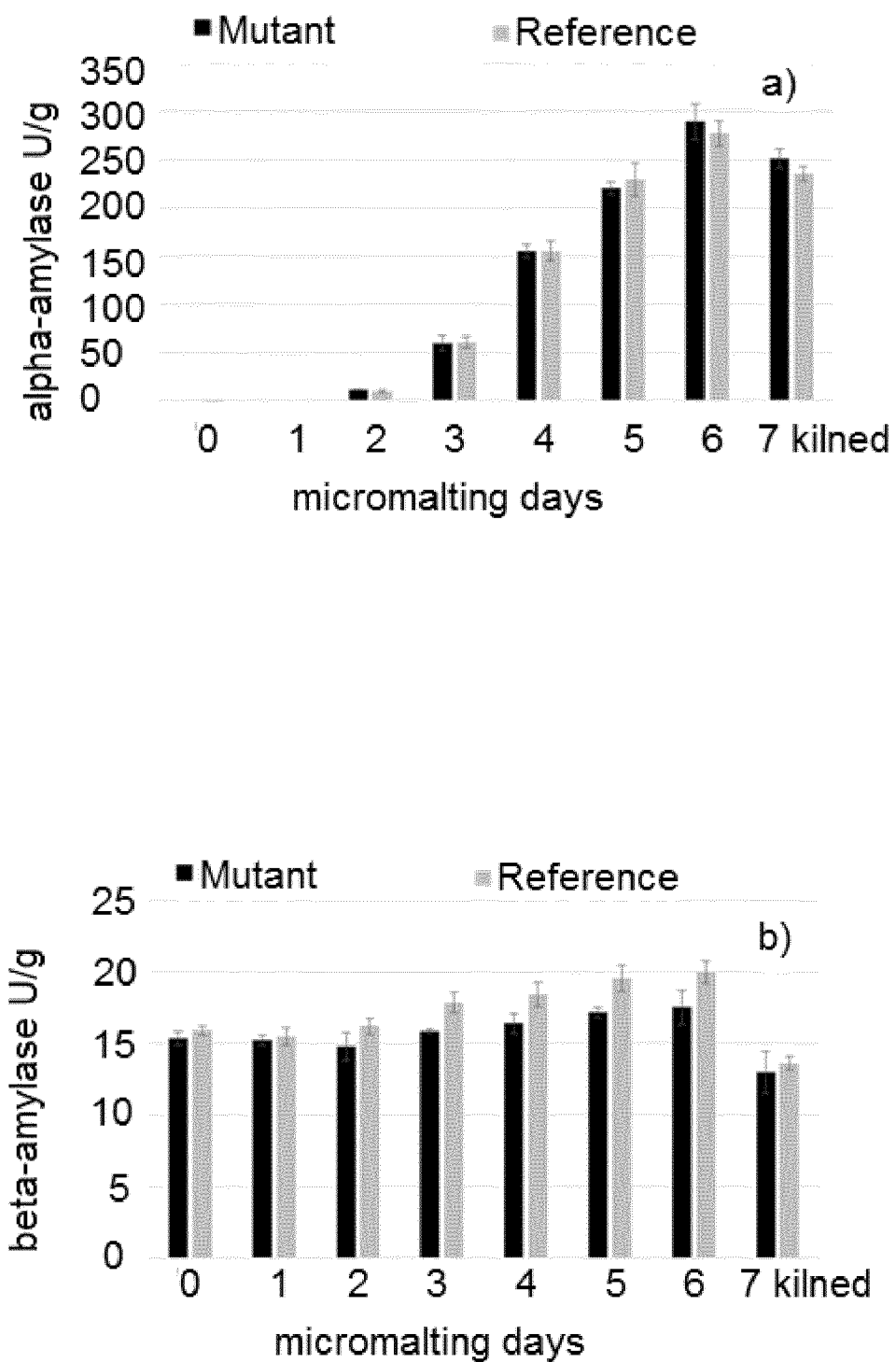
FIG. 5 shows α-amylase (a), β-amylase (b) and free limit dextrinase (c) activities measured in Mutant 2 (Mutant) and in cv. Paustian (Reference) grains during malting.

Prior to enzyme activity analysis the malt samples were milled using a standard Foss Cyclotech mill equipped with a tungsten carbide grinding ring (Foss 10004463), nickel plated impeller (Foss 1000 2666) and a 1 mm outlet screen (Foss 10001989). All enzyme activity measurements of barley malt were made within 48 h after milling of the dry sample. Alpha-amylase activity assays were measured using a Ceralpha kit (K-CERA) from Megazyme using standard laboratory equipment. The amylase assays were made according to manufacturer's protocol (K-CERA 01/12). Calculation of amylase activity was based on the formula in the Megazyme protocol (K-CERA 01/12). Beta-amylase activity assays were measured using Betamyl kit (K-BETA3) from Megazyme using standard laboratory equipment. The amylase assays were made according to the manufacturer's protocol (K-BETA3 10/10). Calculation of beta-amylase activity was based on the formula in the Megazyme protocol (K-BETA3 10/10). Limit dextrinase activity assays were measured using a Pullulanase/Limit Dextrinase Assay kit (PullG6 Method) kit (K-PullG6) from Megazyme using standard laboratory equipment. The limit dextrinase assays were made according to manufacturer's protocol (K-PullG6 05/17). Calculation of limit dextrinase activity was based on the formula in the Megazyme protocol (K-PullG6 05/17).
Results:

The total enzymatic activities measured for α-amylase, β-amylase and free limit dextrinase follow the same pattern in Mutant 2 and reference barley line (FIG. 5). Surprisingly, the limit dextrinase activity appear to be slightly higher in the mutant starting as early as day 3, although the limit dextrinase gene expression was slightly lower.

Example 8

(1-3;1-4)-β-Glucan Content

Figure 6:
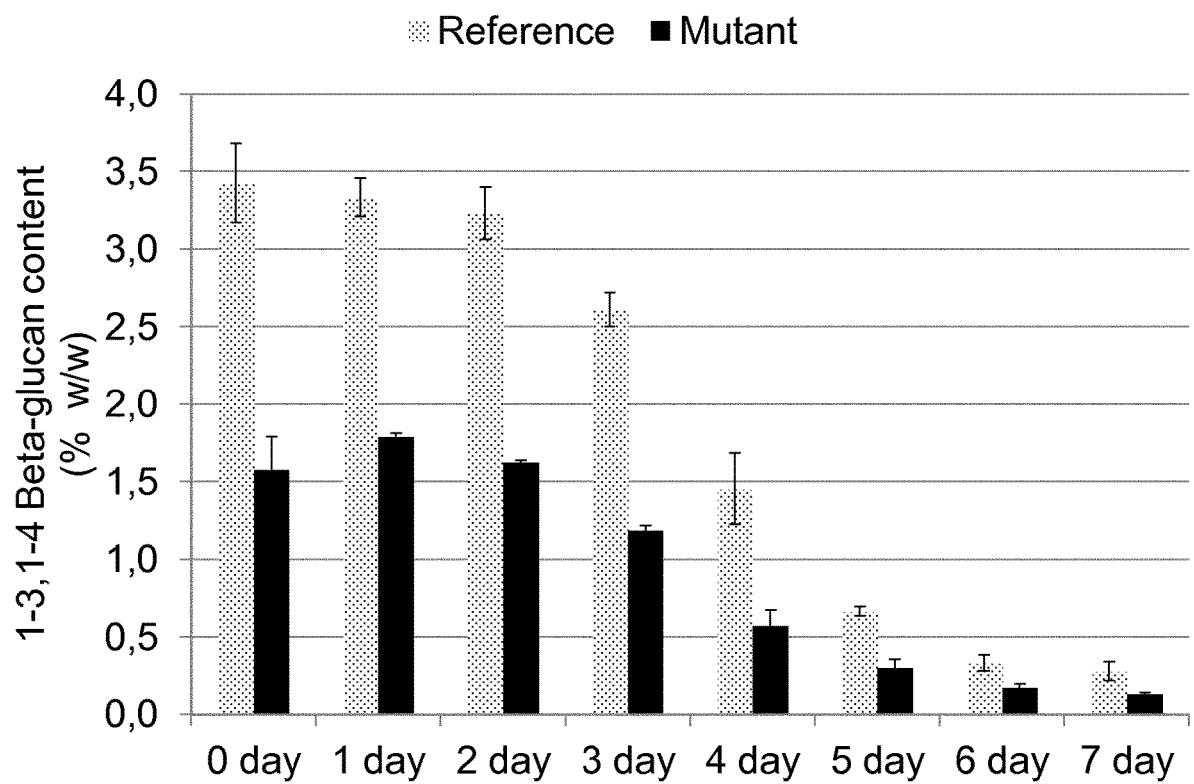
FIG. 6 shows (1-3;1-4)-β-glucan content in Mutant 2 (Mutant) and in cv. Paustian (Reference) grains mature barley grains (0 day) and in green malt at 1,2,3,4,5,6 days as well as in the kilned malts. (7 day).

The germinated grains prepared as described in Example 7 were analysed for total (1,3;1,4)-β-glucan content. Ten mL barley grains were milled on a Retch cyclone mill. All samples were analysed in triplicates. Twenty mg of flour was weight out in 2 mL Eppendorf tubes, heated for 2 hours at 100° C. in an oven followed by cooling to room temperature. In total, 500 µL 50% aqueous methanol was added and the samples were shaken at 1400 rpm for 1 hour. Following centrifugation at 16000×g for 10 minutes, the supernatant was discarded and the samples dried overnight. Then 400 µL of 20 mM $NaHPO_4$ at pH 6.5 with 1 U/mL lichenase (Megazyme, International, Ireland) was added per 10 mg flour and incubated at 50° C. for 2.5 hours. The sample was centrifuged at 16000×g for 10 minutes and the supernatant was filtered through 0.45 µm filters and the released Glc-β-(1→4)-Glc-β-(1→3)-Glc (DP3) and Glc-β-(1→4)-Glc-β-(1→4)-Glc-β-(1→3)-Glc (DP4) oligomers were quantified by High-performance anion exchange chromatography with pulsed amperometric detection (HPAEC-PAD). The Glc-β-(1→4)-Glc-β-(1→3)-Glc (DP3) and Glc-β-(1→4)-Glc-β-(1→4)-Glc-β-(1→3)-Glc (DP4) oligomers were quantified with HPAEC-PAD using a Dionex ICS 5000+DC system equipped with a 4 µm SA-10 column with 2×250 mm dimensions and a pre-column. Run conditions were 0.4 mL/min, column temperature 40° C., isocratic 100 mM NaOH eluent for 15 min. A standard for quantification was produced by 1 U/mL lichenase (Megazyme International, Ireland) digestion of known quantities of medium viscosity (1,3;1,4)-β-glucans (Megazyme International, Ireland) in 20 mM $NaHPO_4$ pH 6.5 assuming an equal molar PAD response ratio between DP3 and DP4. The total (1,3;1,4)-β-glucan content was calculated as the sum of the DP3 and DP4 oligomers.
Results:

The (1-3;1-4)-β-glucan content of Mutant 2 (Mutant) and cv. Paustian (Reference) was monitored in barley and in green malt at days 1,2,3,4,5,6 of the malting procedure (FIG. 6) as well as in the kilned malts (day 7 in FIG. 6). During the entire malting process, the (1-3;1-4)-β-glucan content of the Mutant 2 was only 50% of the reference and at day 5 the mutant (1-3;1-4)-β-glucan content was similar to reference kilned malt.

Example 9

Viscosity
Malting:

The barley samples were malted in duplicates using 50 g of barley per sample cup. The barley samples were steeped as a forced submission into 15° C. water in a closed sample grid chamber. The steeping procedure was performed for the first three days as to reach respectively 35%, 40% and 45% in water content at the end of each steeping. Samples were kept for the following three days at 15° C. in germination boxes and equilibrated to 45% water and adjusted by spraying with water to overcome respiration water loss. After these six days samples were kilned for 21 hours in a Termaks incubator and cured using a manual root removal system. For the three days green malt, after the third day of malting samples were freeze dried to 4% water content.

Mashing:

Before mashing samples were milled to fine powder. 70 g of dry matter were mixed in a water:grist ratio 5:1 and mashed in a Lochner mashing equipment according to the following mashing program: 10 minutes at 52° C., 50 minutes at 65° C. and 5 minutes at 78° C., spaced-out by a temperature ramping of 1 degree/min. Samples were collected along the mashing program.

After mashing, wort is filtered through MN 614 ¼, Ø 320 mm (Macherey-Nagel) paper filter. The rheological behavior of the filtered wort is measured in a RheolabQC rotational rheometer (Anton Paar GmbH), supporting a Peltier temperature system (C-PTD 180/AIR/QC) and a double-gap measuring systems (C-DG42/SS, Anton Paar GmbH).

Figure 7:
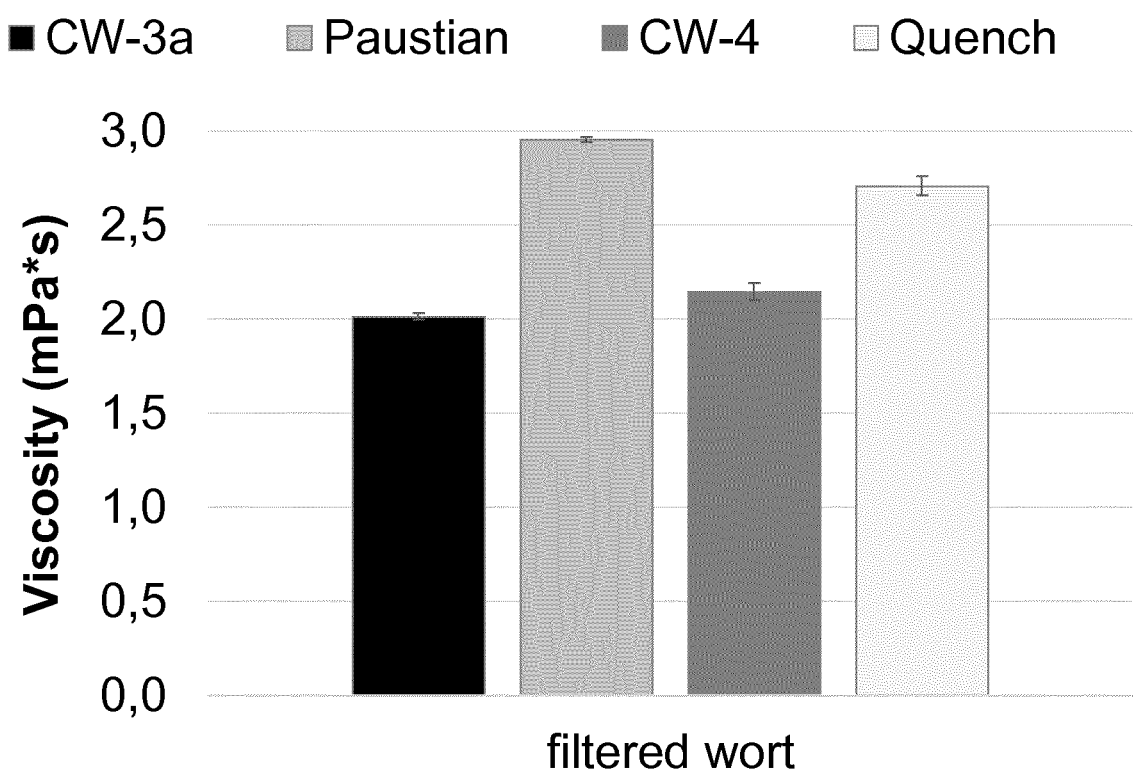
FIG. 7 shows the viscosity of 3-days wort of micro malted Mut 2 (CW-3a) and Mut 5 (CW-4) compared to control (3-days of wort micro malted wild type grains of cv. Paustian and cv. Quench).

Results:

The viscosity of 3-days wort (barley after 3 days of malting) of micro malted Mut 2 and Mut 5 mutants was determined and compared to control (3-days wort of micro malted wild type grains of cv. Paustian and cv. Quench). Viscosity is significantly lower in wort prepared from either mutant compared to the controls, as shown in Table 7 and FIG. 7. The ° Plato was comparable in worts prepared from mutants or references.

The viscosity of a wort prepared from standard malt prepared by steeping for 1-2 days and germination for 5-7 days followed by kiln drying is of about 2 mPa*s.

TABLE 7

| Plato | Mut 2 13.1 | Paustian 13.3 | Mut 5 13.3 | Quench 13.3 |
|---|---|---|---|---|
| (1-3;1-4)-β-glucan (BTG) (mg/l) | 2.44 ± 0.02 | 5.50 ± 0.02 | 2.78 ± 0.01 | 4.91 ± 0.22 |
| Viscosity (mPa*s) | 2.01 ± 0.02 | 2.95 ± 0.01 | 2.15 ± 0.05 | 2.71 ± 0.05 |

REFERENCES

Burton R A and Fincher G B (2014). Evolution and development of cell walls in cereal grains. Front Plant Sci. 5: 456.

Jobling S A (2015). Membrane pore architecture of the CslF6 protein controls (1-3,1-4)-b-glucan structure. Sci. Adv. 1:e1500069.

Holme I B, Wendt T, Gil-Humanes J, Deleuran L C, Staker C G, Voytas D F and Brinch-Pedersen H, (2017). Evaluation of the mature grain phytase candidate HvPAPhy_a gene in barley (*Hordeum vulgare* L.) using CRISPR/Cas9 and TALENs. Plant Mol Biol 95:111-121; (DOI: 10.1007/s11103-017-0640-6).

Hu G, Burton C, Hong Z and Jackson E (2014). A mutation of the cellulose-synthase-like (CslF6) gene in barley (*Hordeum vulgare* L.) partially affects the b-glucan content in grains. Journal of Cereal Science 59, 189-195.

Lawrenson T, Shorinola O, Stacey N, Li C, Østergaard L, Patron N, Uauy C, Harwood W. Induction of targeted, heritable mutations in barley and *Brassica oleracea* using RNA-guided Cas9 nuclease. Genome Biol. 2015 Nov. 30; 16:258. doi:10.1186/s13059-015-0826-7.

Taketa S, Yuo T, Tonooka T, Tsumuraya Y, Inagaki Y, Haruyama N, Larroque O and Jobling S A (2012). Functional characterization of barley betaglucanless mutants demonstrates a unique role for CslF6 in (1,3;1,4)-β-D-glucan biosynthesis. J Exp Bot. 63(1):381-92.

The invention claimed is:

1. A barley plant or a part thereof, wherein the kernels of said barley plant have a reduced (1,3;1,4)-β-glucan content, and wherein said barley plant carries an induced mutation in the CslF6 gene, wherein said mutated CslF6 gene encodes a mutant CslF6 polypeptide comprising the amino acid sequence according to SEQ ID NO:1 or SEQ ID NO: 3 except that said mutant CslF6 comprises a substitution of amino acid 748 of SEQ ID NO:1 or SEQ ID NO:3 to a charged amino acid, wherein the charged amino acid is selected from the group consisting of Arg, His, Lys, Asp and Glu.

2. The barley plant according to claim 1, wherein said barley plant has a (1,3;1,4)-β-glucan content in the range of 1 to 5% dry weight of total kernels.

3. The barley plant according to claim 1, wherein kernels of said barley plant have a (1,3;1,4)-β-glucan content of at least 30% and at most 60% of the (1,3;1,4)-β-glucan content of a barley plant carrying a wild type CslF6 gene, but otherwise of the same genotype.

4. The barley plant according to claim 1, wherein the barley plant comprises grains having a frequency of broken grains after threshing, which is at the most 2 times higher than the frequency of a broken grains after threshing of grains of a barley plant not carrying the mutation in the CslF6 gene, but otherwise of the same genotype.

5. The barley plant according to claim 1, wherein said mutant CslF6 comprises the amino acid sequence according to SEQ ID NO:1 or SEQ ID NO:3 except that mutant CslF6 comprises a substitution of amino acid 748, wherein said substitution is substitution of a glycine (G) to an aspartic acid (D).

6. The barley plant according to claim 1, wherein the kernels of said barley plant have a DP3:DP4 ratio in the range of 2.5 to 4.

7. The barley plant according to claim 1, wherein the barley plant comprises a mutation in one or more additional genes.

8. A plant product selected from the group consisting of green malt, kiln dried malt, wort and beverages, wherein the plant product is prepared from the barley plant according to claim 1 or a part thereof.

9. A method of producing an aqueous extract, said method comprising the steps of:
a) providing kernels of a barley plant according to claim 1;
b) subjecting the barley kernels to a step of germination thereby obtaining germinated kernels, wherein said step of germination comprises incubating said kernels in an aqueous solution for at the most 72 h;
c) finely dividing said germinated kernels, while said germinated kernels have a water content of at least 20%, with the proviso that said barley kernels do not have a water content below 20% at any time following germination and until finely dividing the germinated kernels;
d) preparing an aqueous extract of said finely divided germinated kernels, thereby producing an aqueous extract of the barley.

10. A method of producing a beverage, said method comprising the steps of:
a) Preparing an aqueous extract of kernels of a barley plant and/or malt prepared from a barley plant, wherein the barley plant is the barley plant according to claim 1; and
b) processing said aqueous extract into a beverage.

11. The method according to claim 10, wherein the aqueous extract is prepared by a method comprising the steps of:
a) providing kernels of said barley plant;
b) subjecting the barley kernels to a step of germination thereby obtaining germinated kernels, wherein said step of germination comprises incubating said kernels in an aqueous solution for at the most 72 h;
c) finely dividing said germinated kernels, while said germinated kernels have a water content of at least 20%, with the proviso that said barley kernels do not have a water content below 20% at any time following germination and until finely dividing the germinated kernels; and
d) preparing an aqueous extract of said finely divided germinated kernels, thereby producing an aqueous extract of the barley.

12. The barley plant according to claim 1, wherein said barley plant has a (1,3;1,4)-β-glucan content in the range of 1.3 to 3% dry weight of total kernels.

13. The barley plant according to claim 1, wherein said barley plant has a (1,3;1,4)-β-glucan content in the range of 1.3 to 2% dry weight of total kernels.

14. The barley plant according to claim 7, wherein said mutation in one or more additional genes is selected from the group consisting of:
a. a mutation in the gene encoding LOX-1 resulting in a total loss of functional LOX-1;
b. a mutation in the gene encoding LOX-2 resulting in a total loss of functional LOX-2; and
c. a mutation in the gene encoding MMT resulting in a total loss of functional MMT.

* * * * *

SEQUENCE LISTING

```
<160> NUMBER OF SEQ ID NOS: 27

<210> SEQ ID NO 1
<211> LENGTH: 947
<212> TYPE: PRT
<213> ORGANISM: Hordeum vulgare

<400> SEQUENCE: 1

Met Ala Pro Ala Val Ala Gly Gly Gly Arg Val Arg Ser Asn Glu Pro
1               5                   10                  15

Val Ala Ala Ala Ala Ala Pro Ala Ala Ser Gly Lys Pro Cys Val
            20                  25                  30

Cys Gly Phe Gln Val Cys Ala Cys Thr Gly Ser Ala Ala Val Ala Ser
        35                  40                  45

Ala Ala Ser Ser Leu Asp Met Asp Ile Val Ala Met Gly Gln Ile Gly
    50                  55                  60

Ala Val Asn Asp Glu Ser Trp Val Gly Val Glu Leu Gly Glu Asp Gly
65                  70                  75                  80

Glu Thr Asp Glu Ser Gly Ala Ala Val Asp Asp Arg Pro Val Phe Arg
                85                  90                  95

Thr Glu Lys Ile Lys Gly Val Leu Leu His Pro Tyr Arg Val Leu Ile
                100                 105                 110
```

```
Phe Val Arg Leu Ile Ala Phe Thr Leu Phe Val Ile Trp Arg Ile Ser
        115                 120                 125

His Lys Asn Pro Asp Ala Met Trp Leu Trp Val Thr Ser Ile Cys Gly
130                 135                 140

Glu Phe Trp Phe Gly Phe Ser Trp Leu Leu Asp Gln Leu Pro Lys Leu
145                 150                 155                 160

Asn Pro Ile Asn Arg Val Pro Asp Leu Ala Val Leu Arg Gln Arg Phe
                165                 170                 175

Asp Arg Pro Asp Gly Thr Ser Thr Leu Pro Gly Leu Asp Ile Phe Val
            180                 185                 190

Thr Thr Ala Asp Pro Ile Lys Glu Pro Ile Leu Ser Thr Ala Asn Ser
        195                 200                 205

Val Leu Ser Ile Leu Ala Ala Asp Tyr Pro Val Asp Arg Asn Thr Cys
    210                 215                 220

Tyr Val Ser Asp Asp Ser Gly Met Leu Leu Thr Tyr Glu Ala Leu Ala
225                 230                 235                 240

Glu Ser Ser Lys Phe Ala Thr Leu Trp Val Pro Phe Cys Arg Lys His
                245                 250                 255

Gly Ile Glu Pro Arg Gly Pro Glu Ser Tyr Phe Glu Leu Lys Ser His
            260                 265                 270

Pro Tyr Met Gly Arg Ala Gln Asp Glu Phe Val Asn Asp Arg Arg Arg
        275                 280                 285

Val Arg Lys Glu Tyr Asp Glu Phe Lys Ala Arg Ile Asn Ser Leu Glu
    290                 295                 300

His Asp Ile Lys Gln Arg Asn Asp Gly Tyr Asn Ala Ala Ile Ala His
305                 310                 315                 320

Ser Gln Gly Val Pro Arg Pro Thr Trp Met Ala Asp Gly Thr Gln Trp
                325                 330                 335

Glu Gly Thr Trp Val Asp Ala Ser Glu Asn His Arg Arg Gly Asp His
            340                 345                 350

Ala Gly Ile Val Leu Val Leu Asn His Pro Ser His Arg Arg Gln
        355                 360                 365

Thr Gly Pro Pro Ala Ser Ala Asp Asn Pro Leu Asp Leu Ser Gly Val
    370                 375                 380

Asp Val Arg Leu Pro Met Leu Val Tyr Val Ser Arg Glu Lys Arg Pro
385                 390                 395                 400

Gly His Asp His Gln Lys Lys Ala Gly Ala Met Asn Ala Leu Thr Arg
                405                 410                 415

Ala Ser Ala Leu Leu Ser Asn Ser Pro Phe Ile Leu Asn Leu Asp Cys
            420                 425                 430

Asp His Tyr Ile Asn Asn Ser Gln Ala Leu Arg Ala Gly Ile Cys Phe
        435                 440                 445

Met Val Gly Arg Asp Ser Asp Thr Val Ala Phe Val Gln Phe Pro Gln
    450                 455                 460

Arg Phe Glu Gly Val Asp Pro Thr Asp Leu Tyr Ala Asn His Asn Arg
465                 470                 475                 480

Ile Phe Phe Asp Gly Thr Leu Arg Ala Leu Asp Gly Met Gln Gly Pro
                485                 490                 495

Ile Tyr Val Gly Thr Gly Cys Leu Phe Arg Arg Ile Thr Val Tyr Gly
            500                 505                 510

Phe Asp Pro Pro Arg Ile Asn Val Gly Gly Pro Cys Phe Pro Arg Leu
        515                 520                 525
```

Ala Gly Leu Phe Ala Lys Thr Lys Tyr Glu Lys Pro Gly Leu Glu Met
530                 535                 540

Thr Thr Ala Lys Ala Lys Ala Ala Pro Val Pro Ala Lys Gly Lys His
545                 550                 555                 560

Gly Phe Leu Pro Leu Pro Lys Lys Thr Tyr Gly Lys Ser Asp Ala Phe
                565                 570                 575

Val Asp Thr Ile Pro Arg Ala Ser His Pro Ser Pro Tyr Ala Ala Ala
            580                 585                 590

Ala Glu Gly Ile Val Ala Asp Glu Ala Thr Ile Val Glu Ala Val Asn
        595                 600                 605

Val Thr Ala Ala Ala Phe Glu Lys Lys Thr Gly Trp Gly Lys Glu Ile
610                 615                 620

Gly Trp Val Tyr Asp Thr Val Thr Glu Asp Val Val Thr Gly Tyr Arg
625                 630                 635                 640

Met His Ile Lys Gly Trp Arg Ser Arg Tyr Cys Ser Ile Tyr Pro His
                645                 650                 655

Ala Phe Ile Gly Thr Ala Pro Ile Asn Leu Thr Glu Arg Leu Phe Gln
            660                 665                 670

Val Leu Arg Trp Ser Thr Gly Ser Leu Glu Ile Phe Phe Ser Lys Asn
        675                 680                 685

Asn Pro Leu Phe Gly Ser Thr Tyr Leu His Pro Leu Gln Arg Val Ala
690                 695                 700

Tyr Ile Asn Ile Thr Thr Tyr Pro Phe Thr Ala Ile Phe Leu Ile Phe
705                 710                 715                 720

Tyr Thr Thr Val Pro Ala Leu Ser Phe Val Thr Gly His Phe Ile Val
                725                 730                 735

Gln Arg Pro Thr Thr Met Phe Tyr Val Tyr Leu Gly Ile Val Leu Ser
            740                 745                 750

Thr Leu Leu Val Ile Ala Val Leu Glu Val Lys Trp Ala Gly Val Thr
        755                 760                 765

Val Phe Glu Trp Phe Arg Asn Gly Gln Phe Trp Met Thr Ala Ser Cys
770                 775                 780

Ser Ala Tyr Leu Ala Ala Val Cys Gln Val Leu Thr Lys Val Ile Phe
785                 790                 795                 800

Arg Arg Asp Ile Ser Phe Lys Leu Thr Ser Lys Leu Pro Ser Gly Asp
                805                 810                 815

Glu Lys Lys Asp Pro Tyr Ala Asp Leu Tyr Val Val Arg Trp Thr Pro
            820                 825                 830

Leu Met Ile Thr Pro Ile Ile Ile Phe Val Asn Ile Ile Gly Ser
        835                 840                 845

Ala Val Ala Phe Ala Lys Val Leu Asp Gly Glu Trp Thr His Trp Leu
850                 855                 860

Lys Val Ala Gly Gly Val Phe Phe Asn Phe Trp Val Leu Phe His Leu
865                 870                 875                 880

Tyr Pro Phe Ala Lys Gly Ile Leu Gly Lys His Gly Lys Thr Pro Val
                885                 890                 895

Val Val Leu Val Trp Trp Ala Phe Thr Phe Val Ile Thr Ala Val Leu
            900                 905                 910

Tyr Ile Asn Ile Pro His Met His Thr Ser Gly Gly Lys His Thr Thr
        915                 920                 925

Val His Gly His His Gly Lys Lys Leu Val Asp Thr Gly Leu Tyr Gly
           930                 935                 940

Trp Leu His
945

<210> SEQ ID NO 2
<211> LENGTH: 2844
<212> TYPE: DNA
<213> ORGANISM: Hordeum vulgare

<400> SEQUENCE: 2

| | | | | | |
|---|---|---|---|---|---|
| atggcgccag | cggtggccgg | aggggccgc | gtgcggagca | atgagccggt | tgctgctgct | 60 |
| gccgccgcgc | cggcggccag | cggcaagccc | tgcgtgtgcg | gcttccaggt | ttgcgcctgc | 120 |
| acggggtcgg | ccgcggtggc | ctccgccgcc | tcgtcgctgg | acatggacat | cgtgccatg | 180 |
| gggcagatcg | gcgccgtcaa | cgacgagagc | tgggtgggcg | tggagctcgg | cgaagatggc | 240 |
| gagaccgacg | aaagcggtgc | cgccgttgac | gaccgcccg | tattccgcac | cgagaagatc | 300 |
| aagggtgtcc | tcctccaccc | ctaccgggtg | ctgattttcg | ttcgtctgat | cgccttcacg | 360 |
| ctgttcgtga | tctggcgtat | ctcccacaag | aacccagacg | cgatgtggct | gtgggtgaca | 420 |
| tccatctgcg | gcgagttctg | gttcggtttc | tcgtggctgc | tagatcagct | gcccaagctg | 480 |
| aaccccatca | accgcgtgcc | ggacctggcg | gtgctgcggc | agcgcttcga | ccgcccgac | 540 |
| ggcacctcca | cgctcccggg | gctggacatc | ttcgtcacca | cggccgaccc | catcaaggag | 600 |
| cccatcctct | ccaccgccaa | ctcggtgctc | tccatcctgg | ccgccgacta | ccccgtggac | 660 |
| cgcaacacat | gctacgtctc | cgacgacagt | ggcatgctgc | tcacctacga | ggccctggca | 720 |
| gagtcctcca | gttcgccac | gctctgggtg | cccttctgcc | gcaagcacgg | gatcgagccc | 780 |
| aggggtccgg | agagctactt | cgagctcaag | tcacaccctt | acatggggag | agcccaggac | 840 |
| gagttcgtca | cgaccgccg | ccgcgttcgc | aaggagtacg | acgagttcaa | ggccaggatc | 900 |
| aacagcctgg | agcatgacat | caagcagcgc | aacgacgggt | acaacgccgc | cattgcccac | 960 |
| agccaaggcg | tgccccggcc | cacctggatg | gcggacggca | cccagtggga | gggcacatgg | 1020 |
| gtcgacgcct | ccgagaacca | ccgcaggggc | gaccacgccg | gcatcgtact | ggtgctgctg | 1080 |
| aaccacccga | gccaccgccg | gcagacgggc | ccgccggcga | gcgctgacaa | cccactggac | 1140 |
| ttgagcggcg | tggatgtgcg | tctccccatg | ctggtgtacg | tgtcccgtga | aagcgcccc | 1200 |
| gggcacgacc | accagaagaa | ggccggtgcc | atgaacgcgc | ttacccgcgc | tcggcgctg | 1260 |
| ctctccaact | ccccttcat | cctcaacctc | gactgcgatc | attacatcaa | caactcccag | 1320 |
| gcccttcgcg | ccggcatctg | cttcatggtg | ggacgggaca | gcgacacggt | tgccttcgtc | 1380 |
| cagttcccgc | agcgcttcga | gggcgtcgac | cccaccgacc | tctacgccaa | ccacaaccgc | 1440 |
| atcttcttcg | acggcacct | ccgtgccctg | acggcatgc | agggccccat | ctacgtcggc | 1500 |
| actgggtgtc | tcttccgccg | catcaccgtc | tacggcttcg | acccgccgag | gatcaacgtc | 1560 |
| ggcggtccct | gcttccccag | gctcgccggg | ctcttcgcca | agaccaagta | cgagaagccc | 1620 |
| gggctcgaga | tgaccacggc | caaggccaag | gccgcgcccg | tgcccgccaa | gggtaagcac | 1680 |
| ggcttcttgc | cactgcccaa | gaagacgtac | ggcaagtcgg | acgccttcgt | ggacaccatc | 1740 |
| ccgcgcgcgt | cgcacccgtc | gccctacgcc | gcggcggctg | aggggatcgt | ggccgacgag | 1800 |
| gcgaccatcg | tcgaggcggt | gaacgtgacg | gccgccgcgt | tcgagaagaa | gaccggctgg | 1860 |
| ggcaaagaga | tcggctgggt | gtacgacacc | gtcacggagg | acgtggtcac | cggctaccgg | 1920 |

```
atgcatatca agggtggcg gtcacgctac tgctccatct acccacacgc cttcatcggc    1980
accgccccca tcaacctcac ggagaggctc ttccaggtgc tccgctggtc cacgggatcc    2040
ctcgagatct tcttctccaa gaacaacccg ctcttcggca gcacatacct ccaccgctg     2100 cagcgcgtcg cctacatcaa catcaccact taccccttca ccgccatctt cctcatcttc    2160
tacaccaccg tgccggcgct atccttcgtc accggccact tcatcgtgca gcgcccgacc    2220
accatgttct acgtctacct gggcatcgtg ctatccacgc tgctcgtcat cgccgtgctg    2280
gaggtcaagt gggccggggt cacagtcttc gagtggttca ggaacggcca gttctggatg    2340
acagcaagtt gctccgccta cctcgccgcc gtctgccagg tgctgaccaa ggtgatattc    2400
cggcgggaca tctccttcaa gctcacatcc aagctaccct cgggagacga aagaaggac      2460 ccctacgccg acctctacgt ggtgcgctgg acgccgctca tgattacacc catcatcatc    2520
atcttcgtca acatcatcgg atccgccgtg gccttcgcca aggttctcga cggcgagtgg    2580
acgcactggc tcaaggtcgc cggcggcgtc ttcttcaact tctgggtgct cttccacctc    2640
taccccttcg ccaagggcat cctggggaag cacggaaaga cgccagtcgt ggtgctcgtc    2700
tggtgggcat tcaccttcgt catcaccgcc gtgctctaca tcaacatccc ccacatgcat    2760
acctcgggag gcaagcacac aacggtgcat ggtcaccatg gcaagaagtt ggtcgacaca    2820
gggctctatg gctggctcca ttga                                         2844
```

<210> SEQ ID NO 3
<211> LENGTH: 947
<212> TYPE: PRT
<213> ORGANISM: Hordeum vulgare

<400> SEQUENCE: 3

Met Ala Pro Ala Val Ala Gly Gly Arg Val Arg Ser Asn Glu Pro
1               5                   10                  15

Val Ala Ala Ala Ala Ala Pro Ala Ala Ser Gly Lys Pro Cys Val
            20                  25                  30

Cys Gly Phe Gln Val Cys Ala Cys Thr Gly Ser Ala Ala Val Ala Ser
            35                  40                  45

Ala Ala Ser Ser Leu Asp Met Asp Ile Val Ala Met Gly Gln Ile Gly
        50                  55                  60

Ala Val Asn Asp Glu Ser Trp Val Gly Val Glu Leu Gly Glu Asp Gly
65                  70                  75                  80

Glu Thr Asp Glu Ser Gly Ala Ala Val Asp Asp Arg Pro Val Phe Arg
                85                  90                  95

Thr Glu Lys Ile Lys Gly Val Leu Leu His Pro Tyr Arg Val Leu Ile
            100                 105                 110

Phe Val Arg Leu Ile Ala Phe Thr Leu Phe Val Ile Trp Arg Ile Ser
            115                 120                 125

His Lys Asn Pro Asp Ala Met Trp Leu Trp Val Thr Ser Ile Cys Gly
        130                 135                 140

Glu Phe Trp Phe Gly Phe Ser Trp Leu Leu Asp Gln Leu Pro Lys Leu
145                 150                 155                 160

Asn Pro Ile Asn Arg Val Pro Asp Leu Ala Val Leu Arg Gln Arg Phe
                165                 170                 175

Asp Arg Pro Asp Gly Thr Ser Thr Leu Pro Gly Leu Asp Ile Phe Val
            180                 185                 190

Thr Thr Ala Asp Pro Ile Lys Glu Pro Ile Leu Ser Thr Ala Asn Ser
            195                 200                 205

```
Val Leu Ser Ile Leu Ala Ala Asp Tyr Pro Val Asp Arg Asn Thr Cys
    210                 215                 220

Tyr Val Ser Asp Asp Ser Gly Met Leu Thr Tyr Glu Ala Leu Ala
225                 230                 235                 240

Glu Ser Ser Lys Phe Ala Thr Leu Trp Val Pro Phe Cys Arg Lys His
                245                 250                 255

Gly Ile Glu Pro Arg Gly Pro Glu Ser Tyr Phe Glu Leu Lys Ser His
                260                 265                 270

Pro Tyr Met Gly Arg Ala Gln Asp Glu Phe Val Asn Asp Arg Arg Arg
            275                 280                 285

Val Arg Lys Glu Tyr Asp Glu Phe Lys Ala Arg Ile Asn Ser Leu Glu
290                 295                 300

His Asp Ile Lys Gln Arg Asn Asp Gly Tyr Asn Ala Ala Ile Ala His
305                 310                 315                 320

Ser Gln Gly Val Pro Arg Pro Thr Trp Met Ala Asp Gly Thr Gln Trp
                325                 330                 335

Glu Gly Thr Trp Val Asp Ala Ser Glu Asn His Arg Arg Gly Asp His
                340                 345                 350

Ala Gly Ile Val Leu Val Leu Leu Asn His Pro Ser His Arg Arg Gln
                355                 360                 365

Thr Gly Pro Pro Ala Ser Ala Asp Asn Pro Leu Asp Leu Ser Gly Val
    370                 375                 380

Asp Val Arg Leu Pro Met Leu Val Tyr Val Ser Arg Glu Lys Arg Pro
385                 390                 395                 400

Gly His Asp His Gln Lys Lys Ala Gly Ala Met Asn Ala Leu Thr Arg
                405                 410                 415

Ala Ser Ala Leu Leu Ser Asn Ser Pro Phe Ile Leu Asn Leu Asp Cys
                420                 425                 430

Asp His Tyr Ile Asn Asn Ser Gln Ala Leu Arg Ala Gly Ile Cys Phe
                435                 440                 445

Met Val Gly Arg Asp Ser Asp Thr Val Ala Phe Val Gln Phe Pro Gln
    450                 455                 460

Arg Phe Glu Gly Val Asp Pro Thr Asp Leu Tyr Ala Asn His Asn Arg
465                 470                 475                 480

Ile Phe Phe Asp Gly Thr Leu Arg Ala Leu Asp Gly Met Gln Gly Pro
                485                 490                 495

Ile Tyr Val Gly Thr Gly Cys Leu Phe Arg Arg Ile Thr Val Tyr Gly
                500                 505                 510

Phe Asp Pro Pro Arg Ile Asn Val Gly Gly Pro Cys Phe Pro Arg Leu
            515                 520                 525

Ala Gly Leu Phe Ala Lys Thr Lys Tyr Glu Lys Pro Gly Leu Glu Met
530                 535                 540

Thr Thr Ala Lys Ala Lys Ala Ala Pro Val Pro Ala Lys Gly Lys His
545                 550                 555                 560

Gly Phe Leu Pro Leu Pro Lys Lys Thr Tyr Gly Lys Ser Asp Ala Phe
                565                 570                 575

Val Asp Thr Ile Pro Arg Ala Ser His Pro Ser Pro Tyr Thr Ala Ala
            580                 585                 590

Ala Glu Gly Ile Val Ala Asp Glu Ala Thr Ile Val Glu Ala Val Asn
            595                 600                 605

Val Thr Ala Ala Ala Phe Glu Lys Lys Thr Gly Trp Gly Lys Glu Ile
            610                 615                 620
```

```
Gly Trp Val Tyr Asp Thr Val Thr Glu Asp Val Val Thr Gly Tyr Arg
625                 630                 635                 640

Met His Ile Lys Gly Trp Arg Ser Arg Tyr Cys Ser Ile Tyr Pro His
            645                 650                 655

Ala Phe Ile Gly Thr Ala Pro Ile Asn Leu Thr Glu Arg Leu Phe Gln
        660                 665                 670

Val Leu Arg Trp Ser Thr Gly Ser Leu Glu Ile Phe Phe Ser Lys Asn
    675                 680                 685

Asn Pro Leu Phe Gly Ser Thr Tyr Leu His Pro Leu Gln Arg Val Ala
690                 695                 700

Tyr Ile Asn Ile Thr Thr Tyr Pro Phe Thr Ala Ile Phe Leu Ile Phe
705                 710                 715                 720

Tyr Thr Thr Val Pro Ala Leu Ser Phe Val Thr Gly His Phe Ile Val
            725                 730                 735

Gln Arg Pro Thr Thr Met Phe Tyr Val Tyr Leu Gly Ile Val Leu Ser
        740                 745                 750

Thr Leu Leu Val Ile Ala Val Leu Glu Val Lys Trp Ala Gly Val Thr
    755                 760                 765

Val Phe Glu Trp Phe Arg Asn Gly Gln Phe Trp Met Thr Ala Ser Cys
770                 775                 780

Ser Ala Tyr Leu Ala Ala Val Cys Gln Val Leu Thr Lys Val Ile Phe
785                 790                 795                 800

Arg Arg Asp Ile Ser Phe Lys Leu Thr Ser Lys Leu Pro Ser Gly Asp
            805                 810                 815

Glu Lys Lys Asp Pro Tyr Ala Asp Leu Tyr Val Val Arg Trp Thr Pro
        820                 825                 830

Leu Met Ile Thr Pro Ile Ile Ile Phe Val Asn Ile Ile Gly Ser
    835                 840                 845

Ala Val Ala Phe Ala Lys Val Leu Asp Gly Glu Trp Thr His Trp Leu
850                 855                 860

Lys Val Ala Gly Gly Val Phe Phe Asn Phe Trp Val Leu Phe His Leu
865                 870                 875                 880

Tyr Pro Phe Ala Lys Gly Ile Leu Gly Lys His Gly Lys Thr Pro Val
            885                 890                 895

Val Val Leu Val Trp Trp Ala Phe Thr Phe Val Ile Thr Ala Val Leu
        900                 905                 910

Tyr Ile Asn Ile Pro His Met His Thr Ser Gly Gly Lys His Thr Thr
    915                 920                 925

Val His Gly His His Gly Lys Lys Leu Val Asp Thr Gly Leu Tyr Gly
930                 935                 940

Trp Leu His
945

<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4
tacacccatc atcatcatct                                              20

<210> SEQ ID NO 5
<211> LENGTH: 15
```

```
<212> TYPE: DNA
<213> ORGANISM: Artificial sequence
<220> FEATURE:
<223> OTHER INFORMATION: Primer

<400> SEQUENCE: 5
cgagaacctt ggcga                                                15

<210> SEQ ID NO 6
<211> LENGTH: 16
<212> TYPE: DNA
<213> ORGANISM: Artificial sequence
<220> FEATURE:
<223> OTHER INFORMATION: Probe

<400> SEQUENCE: 6
atcatcgaat ccgccg                                               16

<210> SEQ ID NO 7
<211> LENGTH: 16
<212> TYPE: DNA
<213> ORGANISM: Artificial sequence
<220> FEATURE:
<223> OTHER INFORMATION: Probe

<400> SEQUENCE: 7
catcatcgga tccgcc                                               16

<210> SEQ ID NO 8
<211> LENGTH: 16
<212> TYPE: DNA
<213> ORGANISM: Artificial sequence
<220> FEATURE:
<223> OTHER INFORMATION: Primer

<400> SEQUENCE: 8
ccgaccacca tgttct                                               16

<210> SEQ ID NO 9
<211> LENGTH: 15
<212> TYPE: DNA
<213> ORGANISM: Artificial sequence
<220> FEATURE:
<223> OTHER INFORMATION: Primer

<400> SEQUENCE: 9
ggcgatgacg agcag                                                15

<210> SEQ ID NO 10
<211> LENGTH: 17
<212> TYPE: DNA
<213> ORGANISM: Artificial sequence
<220> FEATURE:
<223> OTHER INFORMATION: Probe

<400> SEQUENCE: 10
ctacctggac atcgtgc                                              17

<210> SEQ ID NO 11
<211> LENGTH: 16
<212> TYPE: DNA
<213> ORGANISM: Artificial sequence
<220> FEATURE:
<223> OTHER INFORMATION: Probe
```

```
<400> SEQUENCE: 11
ctacctgggc atcgtg                                                    16

<210> SEQ ID NO 12
<211> LENGTH: 18
<212> TYPE: DNA
<213> ORGANISM: Artificial sequence
<220> FEATURE:
<223> OTHER INFORMATION: Primer

<400> SEQUENCE: 12
actgctccat ctacccac                                                  18

<210> SEQ ID NO 13
<211> LENGTH: 18
<212> TYPE: DNA
<213> ORGANISM: Artificial sequence
<220> FEATURE:
<223> OTHER INFORMATION: Primer

<400> SEQUENCE: 13
gtatgtgctg ccgaagag                                                  18

<210> SEQ ID NO 14
<211> LENGTH: 15
<212> TYPE: DNA
<213> ORGANISM: Artificial sequence
<220> FEATURE:
<223> OTHER INFORMATION: Probe

<400> SEQUENCE: 14
tgctccgctg atcca                                                     15

<210> SEQ ID NO 15
<211> LENGTH: 14
<212> TYPE: DNA
<213> ORGANISM: Artificial sequence
<220> FEATURE:
<223> OTHER INFORMATION: Probe

<400> SEQUENCE: 15
tccgctggtc cacg                                                      14

<210> SEQ ID NO 16
<211> LENGTH: 13
<212> TYPE: DNA
<213> ORGANISM: Artificial sequence
<220> FEATURE:
<223> OTHER INFORMATION: Primer

<400> SEQUENCE: 16
caccaccgtg ccg                                                       13

<210> SEQ ID NO 17
<211> LENGTH: 14
<212> TYPE: DNA
<213> ORGANISM: Artificial sequence
<220> FEATURE:
<223> OTHER INFORMATION: Primer

<400> SEQUENCE: 17
catggtggtc gggc                                                      14

<210> SEQ ID NO 18
```

```
<211> LENGTH: 16
<212> TYPE: DNA
<213> ORGANISM: Artificial sequence
<220> FEATURE:
<223> OTHER INFORMATION: Probe

<400> SEQUENCE: 18
cgtcaccgac cacttc                                                    16

<210> SEQ ID NO 19
<211> LENGTH: 15
<212> TYPE: DNA
<213> ORGANISM: Artificial sequence
<220> FEATURE:
<223> OTHER INFORMATION: Probe

<400> SEQUENCE: 19
tcaccggcca cttca                                                     15

<210> SEQ ID NO 20
<211> LENGTH: 20
<212> TYPE: PRT
<213> ORGANISM: Artificial sequence
<220> FEATURE:
<223> OTHER INFORMATION: Oligopeptide fragment

<400> SEQUENCE: 20

Arg Val Leu Ile Phe Val Arg Leu Ile Ala Phe Thr Leu Phe Val Ile
1               5                   10                  15

Trp Arg Ile Ser
            20

<210> SEQ ID NO 21
<211> LENGTH: 22
<212> TYPE: PRT
<213> ORGANISM: Artificial sequence
<220> FEATURE:
<223> OTHER INFORMATION: Oligopeptide fragment

<400> SEQUENCE: 21

Leu Trp Val Thr Ser Ile Cys Gly Glu Phe Trp Phe Gly Phe Ser Trp
1               5                   10                  15

Leu Leu Asp Gln Leu Pro
            20

<210> SEQ ID NO 22
<211> LENGTH: 12
<212> TYPE: PRT
<213> ORGANISM: Artificial sequence
<220> FEATURE:
<223> OTHER INFORMATION: Oligopeptide fragment

<400> SEQUENCE: 22

Leu Gln Arg Val Ala Tyr Ile Asn Ile Thr Thr Tyr
1               5                   10

<210> SEQ ID NO 23
<211> LENGTH: 17
<212> TYPE: PRT
<213> ORGANISM: Artificial sequence
<220> FEATURE:
<223> OTHER INFORMATION: Oligopeptide fragment
```

<400> SEQUENCE: 23

Ala Ile Phe Leu Ile Phe Tyr Thr Thr Val Pro Ala Leu Ser Phe Val
1               5                   10                  15

Thr

<210> SEQ ID NO 24
<211> LENGTH: 18
<212> TYPE: PRT
<213> ORGANISM: Artificial sequence
<220> FEATURE:
<223> OTHER INFORMATION: Oligopeptide fragment

<400> SEQUENCE: 24

Thr Met Phe Tyr Val Tyr Leu Gly Ile Val Leu Ser Thr Leu Leu Val
1               5                   10                  15

Ile Ala

<210> SEQ ID NO 25
<211> LENGTH: 23
<212> TYPE: PRT
<213> ORGANISM: Artificial sequence
<220> FEATURE:
<223> OTHER INFORMATION: Oligopeptide fragment

<400> SEQUENCE: 25

Ile Thr Pro Ile Ile Ile Phe Val Asn Ile Gly Ser Ala Val
1               5                   10                  15

Ala Phe Ala Lys Val Leu Asp
            20

<210> SEQ ID NO 26
<211> LENGTH: 20
<212> TYPE: PRT
<213> ORGANISM: Artificial sequence
<220> FEATURE:
<223> OTHER INFORMATION: Oligopeptide fragment

<400> SEQUENCE: 26

Leu Lys Val Ala Gly Gly Val Phe Phe Asn Phe Trp Val Leu Phe His
1               5                   10                  15

Leu Tyr Pro Phe
            20

<210> SEQ ID NO 27
<211> LENGTH: 947
<212> TYPE: PRT
<213> ORGANISM: Hordeum vulgare

<400> SEQUENCE: 27

Met Ala Pro Ala Val Ala Gly Gly Gly Arg Val Arg Ser Asn Glu Pro
1               5                   10                  15

Val Ala Ala Ala Ala Ala Pro Ala Ala Ser Gly Lys Pro Cys Val
                20                  25                  30

Cys Gly Phe Gln Val Cys Ala Cys Thr Gly Ser Ala Ala Val Ala Ser
            35                  40                  45

Ala Ala Ser Ser Leu Asp Met Asp Ile Val Ala Met Gly Gln Ile Gly
        50                  55                  60

Ala Val Asn Asp Glu Ser Trp Val Gly Val Glu Leu Gly Glu Asp Gly
65                  70                  75                  80

-continued

```
Glu Thr Asp Glu Ser Gly Ala Ala Val Asp Asp Arg Pro Val Phe Arg
                85                  90                  95
Thr Glu Lys Ile Lys Gly Val Leu Leu His Pro Tyr Arg Val Leu Ile
            100                 105                 110
Phe Val Arg Leu Ile Ala Phe Thr Leu Phe Val Ile Trp Arg Ile Ser
        115                 120                 125
His Lys Asn Pro Asp Ala Met Trp Leu Trp Val Thr Ser Ile Cys Gly
130                 135                 140
Glu Phe Trp Phe Gly Phe Ser Trp Leu Leu Asp Gln Leu Pro Lys Leu
145                 150                 155                 160
Asn Pro Ile Asn Arg Val Pro Asp Leu Ala Val Leu Arg Gln Arg Phe
                165                 170                 175
Asp Arg Pro Asp Gly Thr Ser Thr Leu Pro Gly Leu Asp Ile Phe Val
            180                 185                 190
Thr Thr Ala Asp Pro Ile Lys Glu Pro Ile Leu Ser Thr Ala Asn Ser
        195                 200                 205
Val Leu Ser Ile Leu Ala Ala Asp Tyr Pro Val Asp Arg Asn Thr Cys
        210                 215                 220
Tyr Val Ser Asp Asp Ser Gly Met Leu Leu Thr Tyr Glu Ala Leu Ala
225                 230                 235                 240
Glu Ser Ser Lys Phe Ala Thr Leu Trp Val Pro Phe Cys Arg Lys His
                245                 250                 255
Gly Ile Glu Pro Arg Gly Pro Glu Ser Tyr Phe Glu Leu Lys Ser His
            260                 265                 270
Pro Tyr Met Gly Arg Ala Gln Asp Glu Phe Val Asn Asp Arg Arg Arg
        275                 280                 285
Val Arg Lys Glu Tyr Asp Glu Phe Lys Ala Arg Ile Asn Ser Leu Glu
        290                 295                 300
His Asp Ile Lys Gln Arg Asn Asp Gly Tyr Asn Ala Ala Ile Ala His
305                 310                 315                 320
Ser Gln Gly Val Pro Arg Pro Thr Trp Met Ala Asp Gly Thr Gln Trp
                325                 330                 335
Glu Gly Thr Trp Val Asp Ala Ser Glu Asn His Arg Arg Gly Asp His
            340                 345                 350
Ala Gly Ile Val Leu Val Leu Leu Asn His Pro Ser His Arg Arg Gln
        355                 360                 365
Thr Gly Pro Pro Ala Ser Ala Asp Asn Pro Leu Asp Leu Ser Gly Val
        370                 375                 380
Asp Val Arg Leu Pro Met Leu Val Tyr Val Ser Arg Glu Lys Arg Pro
385                 390                 395                 400
Gly His Asp His Gln Lys Lys Ala Gly Ala Met Asn Ala Leu Thr Arg
                405                 410                 415
Ala Ser Ala Leu Leu Ser Asn Ser Pro Phe Ile Leu Asn Leu Asp Cys
            420                 425                 430
Asp His Tyr Ile Asn Asn Ser Gln Ala Leu Arg Ala Gly Ile Cys Phe
        435                 440                 445
Met Val Gly Arg Asp Ser Asp Thr Val Ala Phe Val Gln Phe Pro Gln
        450                 455                 460
Arg Phe Glu Gly Val Asp Pro Thr Asp Leu Tyr Ala Asn His Asn Arg
465                 470                 475                 480
Ile Phe Phe Asp Gly Thr Leu Arg Ala Leu Asp Gly Met Gln Gly Pro
                485                 490                 495
```

```
Ile Tyr Val Gly Thr Gly Cys Leu Phe Arg Arg Ile Thr Val Tyr Gly
            500                 505                 510

Phe Asp Pro Pro Arg Ile Asn Val Gly Gly Pro Cys Phe Pro Arg Leu
        515                 520                 525

Ala Gly Leu Phe Ala Lys Thr Lys Tyr Glu Lys Pro Gly Leu Glu Met
    530                 535                 540

Thr Thr Ala Lys Ala Lys Ala Ala Pro Val Pro Ala Lys Gly Lys His
545                 550                 555                 560

Gly Phe Leu Pro Leu Pro Lys Lys Thr Tyr Gly Lys Ser Asp Ala Phe
                565                 570                 575

Val Asp Thr Ile Pro Arg Ala Ser His Pro Ser Pro Tyr Ala Ala Ala
            580                 585                 590

Ala Glu Gly Ile Val Ala Asp Glu Ala Thr Ile Val Glu Ala Val Asn
        595                 600                 605

Val Thr Ala Ala Ala Phe Glu Lys Lys Thr Gly Trp Gly Lys Glu Ile
    610                 615                 620

Gly Trp Val Tyr Asp Thr Val Thr Glu Asp Val Val Thr Gly Tyr Arg
625                 630                 635                 640

Met His Ile Lys Gly Trp Arg Ser Arg Tyr Cys Ser Ile Tyr Pro His
                645                 650                 655

Ala Phe Ile Gly Thr Ala Pro Ile Asn Leu Thr Glu Arg Leu Phe Gln
            660                 665                 670

Val Leu Arg Trp Ser Thr Gly Ser Leu Glu Ile Phe Phe Ser Lys Asn
        675                 680                 685

Asn Pro Leu Phe Gly Ser Thr Tyr Leu His Pro Leu Gln Arg Val Ala
    690                 695                 700

Tyr Ile Asn Ile Thr Thr Tyr Pro Phe Thr Ala Ile Phe Leu Ile Phe
705                 710                 715                 720

Tyr Thr Thr Val Pro Ala Leu Ser Phe Val Thr Gly His Phe Ile Val
                725                 730                 735

Gln Arg Pro Thr Thr Met Phe Tyr Val Tyr Leu Asp Ile Val Leu Ser
            740                 745                 750

Thr Leu Leu Val Ile Ala Val Leu Glu Val Lys Trp Ala Gly Val Thr
        755                 760                 765

Val Phe Glu Trp Phe Arg Asn Gly Gln Phe Trp Met Thr Ala Ser Cys
    770                 775                 780

Ser Ala Tyr Leu Ala Ala Val Cys Gln Val Leu Thr Lys Val Ile Phe
785                 790                 795                 800

Arg Arg Asp Ile Ser Phe Lys Leu Thr Ser Lys Leu Pro Ser Gly Asp
                805                 810                 815

Glu Lys Lys Asp Pro Tyr Ala Asp Leu Tyr Val Val Arg Trp Thr Pro
            820                 825                 830

Leu Met Ile Thr Pro Ile Ile Ile Phe Val Asn Ile Ile Gly Ser
        835                 840                 845

Ala Val Ala Phe Ala Lys Val Leu Asp Gly Glu Trp Thr His Trp Leu
    850                 855                 860

Lys Val Ala Gly Gly Val Phe Asn Phe Trp Val Leu Phe His Leu
865                 870                 875                 880

Tyr Pro Phe Ala Lys Gly Ile Leu Gly Lys His Gly Lys Thr Pro Val
                885                 890                 895

Val Val Leu Val Trp Trp Ala Phe Thr Phe Val Ile Thr Ala Val Leu
            900                 905                 910
```

```
Tyr Ile Asn Ile Pro His Met His Thr Ser Gly Gly Lys His Thr Thr
        915                 920                 925

Val His Gly His His Gly Lys Lys Leu Val Asp Thr Gly Leu Tyr Gly
    930                 935                 940

Trp Leu His
945
```